US007527793B2

(12) United States Patent
Bae et al.

(10) Patent No.: US 7,527,793 B2
(45) Date of Patent: May 5, 2009

(54) IMMUNOGENIC PEPTIDES

(75) Inventors: Joo-eun Bae, Oak Park, IL (US); Hans-G. Klingemann, Winnetka, IL (US)

(73) Assignee: Rush University Medical Center, Chicago, IL (US)

(*) Notice: Subject to any disclaimer, the term of this patent is extended or adjusted under 35 U.S.C. 154(b) by 594 days.

(21) Appl. No.: 10/428,335

(22) Filed: May 2, 2003

(65) Prior Publication Data

US 2004/0009186 A1    Jan. 15, 2004

Related U.S. Application Data

(60) Provisional application No. 60/509,051, filed on May 3, 2002.

(51) Int. Cl.
*A61K 39/00* (2006.01)
*A61K 38/08* (2006.01)
(52) U.S. Cl. .............. 424/184.1; 424/185.1; 424/277.1
(58) Field of Classification Search .................. None
See application file for complete search history.

(56) References Cited

U.S. PATENT DOCUMENTS

| | | | |
|---|---|---|---|
| 4,603,112 A | 7/1986 | Paoletti et al. | |
| 4,769,330 A | 9/1988 | Paoletti et al. | |
| 4,777,127 A | 10/1988 | Suni et al. | |
| 5,017,487 A | 5/1991 | Stunnenberg et al. | |
| 5,108,921 A | 4/1992 | Low et al. | |
| 5,478,556 A | 12/1995 | Elliott et al. | |
| 5,587,402 A | 12/1996 | Gould et al. | |
| 5,593,972 A | 1/1997 | Weiner et al. | |
| 5,738,867 A | 4/1998 | Spitler | |
| 5,837,248 A | 11/1998 | Kikuchi et al. | |
| 5,879,892 A | 3/1999 | Van Baren et al. | |
| 5,925,362 A | 7/1999 | Spitler et al. | |
| 5,939,526 A | 8/1999 | Gaugler et al. | |
| 5,961,978 A | 10/1999 | Gaudenack et al. | |
| 6,013,268 A | 1/2000 | Reed | |
| 6,080,722 A | 6/2000 | Soppet et al. | |
| 6,162,436 A | 12/2000 | Srivastava | |
| 6,270,778 B1 | 8/2001 | Kawakami et al. | |
| 6,271,019 B1 | 8/2001 | Van Baren et al. | |
| 6,291,430 B1 | 9/2001 | Chaux et al. | |
| 6,306,640 B1 | 10/2001 | Nicolette | |
| 6,329,190 B1 | 12/2001 | Wickham et al. | |
| 6,344,203 B1 | 2/2002 | Sandrin et al. | |
| 6,514,942 B1 * | 2/2003 | Ioannides et al. ............. 514/15 |
| 2002/0007173 A1 | 1/2002 | Kundig et al. | |

FOREIGN PATENT DOCUMENTS

| | | |
|---|---|---|
| EP | 0345242 | 12/1989 |
| GB | 2200651 | 8/1988 |
| WO | WO 89/01973 | 3/1989 |
| WO | WO 90/11092 | 10/1990 |
| WO | WO 91/02805 | 3/1991 |
| WO | WO 94/10308 | 5/1994 |
| WO | WO 0034467 | 6/2000 |
| WO | WO 0142460 | 6/2001 |
| WO | WO 0162286 | 8/2001 |
| WO | WO03/084467 | * 10/2003 |
| WO | WO 03/084467 | * 10/2004 |

OTHER PUBLICATIONS

Brinkman-Van der Linden et al, Molecular and Cellular Biology, Jun. 2003, vol. 23, pp. 4199-4206.*
Bae et al (Cellular Immunology, 2004, vol. 227, pp. 38-50).*
van Elsas et al (European Journal of Immunology, 1996, vol. 26, pp. 1683-1689).*
Parisi et al (Oral Surg Oral Med Oral Pathol Oral Radiol Endod, 2002, vol. 93, pp. 257-263).*
Boyer et al (Blood, 1995, vol. 85, pp. 2498-2506).*
Hunt et al (Science, 1992, vol. 255, pp. 1261-1263).*
Falk et al (Nature, 1991, vol. 351, pp. 290-296).*
A. Raptis, et al., "Polymorphism in CD33 and CD34 Genes: A Source of Minor Histocompatibility Antigens on Haemopoietic Progenitor Cells?" British Journal of Haematology, vol. 102, 1998, pp. 1354-1358.
International Search Report issued Dec. 10, 2005 for PCT/US2003/013998.
Andrews et al., "Myeloid-Associated Differentiation Antigens on Stem Cells and their Progeny Identified by Monoclonal Antibodies," *Blood*, vol. 62, pp. 124-132, 1983. Published by Grune & Stratton.
Spira et al., "The Identification of Monoclonal Class Switch Variants by Sib Selection and an ELISA Assay," *J. Immunol. Methods*, vol. 74, p. 307, 1984. Published by Elsevier Science Publishers B.V.
Griffin et al., "A Monoclonal Antibody Reactive with Normal and Leukemic Human Myeloid Progenitor Cells," *Leuk. Res.*, vol. 8, pp. 521-534, 1984. Published by Pergamon Press, Ltd., Great Britain.
Steplewski et al., "Isolation and Characterization of Anti-Monosialoganglioside Monoclonal Antibody 19-9 Class-Switch Variants," *Proc. Natl. Acad. Sci.*, vol. 82, p. 8653, 1985. Published by National Academy of Sciences, Washington, D.C.
Herlyn et al., "Anti-Idiotypic Antibodies Bear the Internal Image of a Human Tumor Antigen," *Science*, vol. 232, p. 100, 1986. Published by American Association for the Advancement of Science, Washington, D.C.
Sobol et al., Clinical Importance of Myeloid Antigen Expression in Adult Acute Lymphoblastic Leukemia, *N. Engl. J. Med.*, vol. 316, No. 18, pp. 1111-1117, 1987. Published by Massachusetts Medical Society, Boston, M.A.

(Continued)

*Primary Examiner*—Karen A Canella
(74) *Attorney, Agent, or Firm*—Foley & Lardner LLP

(57) ABSTRACT

The invention provides relatively short immunogenic peptides, and biologically active variants thereof, associated with leukemia which elicit an immune response. Nucleic acids encoding the immunogenic peptides and antibodies specific for the peptides are also provided. The immunogenic peptides can be included in pharmaceutical compositions, such as cancer vaccines, and used for the treatment of cancer.

3 Claims, 7 Drawing Sheets

OTHER PUBLICATIONS

Simmons et al., "Isolation of a cDNA Encoding CD33, a Differentiation Antigen of Myeloid Progenitor Cells," *J. Immunol.*, vol. 141, No. 8, pp. 2797-2800, 1988. Published by The American Association of Immunologists, U.S.A.

Berkner, "Development of Adenovirus Vectors for the Expression of Heterologous Genes," *Biotechniques*, vol. 6, pp. 616-627, 1988. Published by Eaton Publishing Company, Natick, MA.

Hopp et al., "A Short Polypeptide Marker Sequence Useful for Recombinant Protein Identification and Purification," *Bio/Technology*, vol. 6, p. 1204, 1988. Published by Nature Publishing Company, New York, NY.

Peiper et al., "Molecular Cloning, Expression, and Chromosomal Localization of a Human Gene Encoding the CD33 Myeloid Differentiation Antigen," *Blood*, vol. 72, pp. 314-321, 1988. Published by Grune & Stratton, Inc.

Fisher-Hoch et al., "Protection of Rhesus Monkeys from Fatal Lassa Fever by Vaccination with a Recombinant Vaccinia Virus Containing the Lassa Virus Glycoprotein Gene," *PNAS*, vol. 86, pp. 317-321, 1989. Published by National Academy of Sciences, Washington, D.C.

Flexner et al., "Attenuation and Immunogenicity in Primates of Vaccinia Virus Recombinants Expressing Human Interleukin-2," *Vaccine*, vol. 8, pp. 17-21, 1989. Published by Butterworth & Co. Ltd.

Kast et al., "Eradication of Adenovirus E1-Induced Tumors by E1A-Specific Cytotoxic T Lymphocytes," *Cell*, vol. 59, pp. 603-614, 1989. Published by Cell Press.

Moss, et al., "Vaccinia Virus Expression Vectors," *Annals of the New York Academy of Science*, vol. 569, pp. 86-103, 1989. Published by New York Academy of Sciences, New York, NY.

Andrews et al., "Precursors of Colony-Forming Cells in Humans can be Distinguished from Colony-forming Cells by Expression of the CD33 and CD34 Antigens and Light Scatter Properties," *J. Exp. Med.*, vol. 169, pp. 1721-1731, 1989. Published by Appleton Press, New York, NY.

Chen et al., "Human Papillomavirus Type 16 Nucleoprotein E7 is a Tumor Rejection Antigen," *Proc. Natl. Acad. Sci. USA*, vol. 88, pp. 110-114, 1991. Published by National Academy of Sciences, Washington, D.C.

Lynch et al., "Immunotherapeutic Elimination of Syngeneic Tumors in vivo by Cytotoxic T Lymphocytes Generated in vitro from Lymphocytes from the Draining Lymph Nodes of Tumor-Bearing Mice," *Eur. J. Immunol.*, vol. 21, pp. 1403-1410, 1991. Published by Verlagsgesellschaft mbH, D-6940 Weinheim.

Rosenfeld et al., "Adenovirus-Mediated Transfer of a Recombinant α1-Antitrypsin Gene to the Lung Epithelium in Vivo," *Science*, vol. 252, pp. 431-434, 1991. Published by American Association for the Advancement of Science, Washington, D.C.

Co et al., "Chimeric and Humanized Antibodies with Specificity for the CD33 Antigen," *J. Immunol.*, vol. 148, pp. 1149-1154, 1992. Published by The American Association of Immunologists, U.S.A.

Young, J., et al., The B7/BB1 Antigen Provides One of Several Costimulatory Signals for the Activation of CD4+T Lymphocytes by Human Blood Dendritic Cells in Vitro, *J Clin Invest* vol. 90, p. 229, 1992. Published by The American Society for Clinical Investigation, Inc.

Riddel et al., "Restoration of Viral Immunity in Immunodeficient Humans by the Adoptive Transfer of T Cell Clones," *Science*, vol. 257, p. 238, 1992. Published by American Association for the Advancement of Science, Washington, D.C.

Robertson et al., "Human Bone Marrow Depleted of CD33-Positive Cells Mediates Delayed but Durable Reconstitution of Hematopoiesis: Clinical Trial of MY9 Monoclonal Antibody-Purged Autografts for the Treatment of Acute Myeloid Leukemia," *Blood*, vol. 79, pp. 2229-2236, 1992. Published by The American Society of Hematology.

Nabavi, et al., "Signalling Through the MHC Class II Cytoplasmic Domain is Required for Antigen Presentation and Induces B7 Expression," Letters to Nature, vol. 360, pp. 266-268, 1992. Published by Macmillan Journals, London, England.

Freeman et al., "Cloning of B7-2: A CTLAa-4 Counter-Receptor That Costimulates Human T Cell Proliferation," *Science*, vol. 262, pp. 909-911, 1993. Published by American Association for the Advancement of Science, Washington, D.C.

Chen, "Naked DNA Points Way to Vaccines," *Science*, vol. 259, pp. 1691-1692, 1993. Published by American Association for the Advancement of Science, Washington, D.C.

Guzman et al., "Efficient and Selective Adenovirus-Mediated Gene Transfer Into Vascular Neointima," *Circulation*, vol. 88, pp. 2838-2848, 1993. Published by Grune & Stratton, New York, NY.

Guzman et al., "Efficient Gene Transfer Into Myocardium by Direct Injection of Adenovirus Vectors," *Cir. Res.*, vol. 73, pp. 1202-1207, 1993. Published by Publication Office, American Heart Association, Dallas, TX.

Kass-Eisler et al., "Quantitative Determination of Adenovirus-Mediated Gene Delivery to Rat Cardiac Myocytes in vitro and in vivo," *PNAS*, vol. 90, pp. 11498-11502, 1993. Published by National Academy of Sciences, Washington, D.C.

Ulmer et al., "Heterologous Protection Against Influenza by Injection of DNA Encoding a Viral Protein," *Science*, vol. 259, pp. 1745-1749, 1993. Published by American Association for the Advancement of Science, Washington, D.C.

Kolls et al., "Prolonged and Effective Blockade of Tumor Necrosis Factor Activity Through Adenovirus-Mediated Gene Transfer," *PNAS*, vol. 91, pp. 215-219, 1994. Published by National Academy of Sciences, Washington, D.C.

Caron et al., "A Phase 1B Trial of Humanized Monoclonal Antibody M195 (Anti-CD33) in Myeloid Leukemia: specific Targeting Without Immunogenicity," *Blood*, vol. 83, pp. 1760-1768, 1994. Published by The American Society of Hematology.

Tchilian et al., "Molecular Cloning of Two Isoforms of the Murine Homolog of the Myeloid CD33 Antigen," *Blood*, vol. 83, No. 11, pp. 3188-3198, Jun. 1, 1994. Published by The American Society of Hematology.

Thomas et al., "Human Peripheral Blood Dendritic Cell Subsets," *J. Immunol.*, vol. 153, pp. 4016-4028, 1994. Published by The American Association of Immunologists.

Nachman et al., "Pseudodipeptide Analogs of the Pyrokinin/PBAN (FXPRLa) Insect Neuropeptide Family Containing Carbocyclic Promimetic Conformational Components," *Regul. Pept.*, vol. 57, pp. 359-370, 1995. Published by Elsevier Science B.V.

Van den Eynde & Brichard, "New Tumor Antigens Recognized by T Cells," *Curr. Opin. Immunol.*, vol. 7, pp. 674-681, 1995. Published by Current Biology Ltd.

Coulie et al., "Antigens Recognized on Human Tumors by Cytolytic T Lymphocytes: Towards Vaccination?," *Stem Cells*, vol. 13, pp. 393-403, 1995. Published by AlphaMed Press.

Hellemans, "IL-12 at the Crossroads," *Science*, vol. 268, pp. 1432-1434, 1995. Published by American Association for the Advancement of Science, Washington, D.C.

Freeman et al., "Characterization of CD33 as a New Member of the Sialoadhesin Family of Cellular Interaction Molecules," *Blood*, vol. 85, pp. 2005-2012, 1995. Published by The American Society of Hematology.

Kwak, L. W. et al., "Vaccination with Syngeneic, Lymphoma-Derived Immunoglobulin Idiotype Combined with Granulocyte/Macrophage Colony-Stimulating Factor Primes Mice for a Protective T-Cell Response," *Proc. Natl. Acad. Sci. USA*, vol. 93, pp. 10972-10977, Oct. 1996. Published by National Academy of Sciences, Wahington, D.C.

Schmidt, W. et al., "Cell-Free Tumor Antigen Peptide-Base Cancer Vaccines," *Proc. Natl. Acad. Sci. USA*, vol. 94, pp. 3262-3267, Apr. 1997;. Published by The National Academy of Sciences of the USA.

Takei et al., "Molecular Cloning of a Novel Gene Similar to Myeloid Antigen CD33 and its Specific Expression in Placenta," *Cytogenet. Cell Genet.*, vol. 78, Nos. 3-4, pp. 295-300, 1997. Published by S. Karger AG, Basel.

Morse, M. A. et al.,., "A Phase I Study of Active Immunotherapy with Carcinoembryonic Antigen Peptide (CAP-1)-Pulsed, Autologous Human Cultured Dendritic Cells in Patients with Metastatic Malignancies Expressing Carcinoembryonic Antigen," *Clinical Cancer Research*, vol. 5, pp. 1331-1338, Jun. 1999. Published by American Association for Cancer Research, Philadelphia, PA.

Muderspach, L et al., "A Phase I Trial of a Human Papillomavirus (HPV) Peptide Vaccine for Women with High-Grade Cervical and Vulvar Intraepithelial Neoplasia who are HPV 16 Positive," *Clinical Cancer Research*, vol. 6, pp. 3406-3416, Sep. 2000. Published by American Association for Cancer Research, Philadelphia, P.A.

Lodge, P. A. et al., "Dendritic Cell-Based Immunotherapy of Prostate Cancer: Immune Monitoring of a Phase II Clinical Trial," *Cancer Research*, vol. 60, pp. 829-833, Feb. 15, 2000. Published by Waverly Press, Baltimore, M.D.

Tourdot, S., et al., "A General Strategy to Enhance Immunogenicity of Low-Affinity HLA-A2.1-Associated Peptides: Implication in the Identification of Cryptic Tumor Epitopes," Eur J Immunol (30) pp. 3411-3421, 2000. Published by Wiley-VCH Verlag GmbH, D-69451 Weinheim.

Bodey, B. et al., "Failure of Cancer Vaccines: the Significant Limitations of this Approach to Immunotherapy," *Anticancer Res.*, vol. 20, No. 4, pp. 2665-2676, 2000. Published by Potamitis Press, Athens, Greece.

Miconnet, I. et al., "Cancer Vaccine Design: A Novel Bacterial Adjuvant for Peptide-Specific CTL Induction," *J. Immunology*, vol. 166, No. 7, pp. 4612-4619, 2001. Published by The American Association of Immunologists.

Gajewski, T. F. et al., "Immunization of HLA-A2+ Melanoma Patients with MAGE-3 or MelanA Peptide-Pulsed Autologous Peripheral Blood Mononuclear Cells Plus Recombinant Human Interleukin 12," *Clinical Cancer Research*, vol. 7, pp. 895s-901s, Mar. 2001 (Suppl.). Published by American Association for Cancer Research, Philadelphia, P.A.

Lau, A., et al., Host Responses to Plasmodium Yoelii Hepatic Stages: A Paradigm in Host-Parasite Interaction. Journal of Immunology, 166:1945-1950, 2001. Published by The American Association of Immunologists.

Lau, R. et al., "Phase I Trial of Intravenous Peptide-Pulsed Dendritic Cells in Patients with Metastatic Melanoma," *Journal of Immunotherapy*, vol. 24, No. 1, pp. 66-78, 2001. Published by Lippincott Williams & Wilkins, Inc., Philadelphia, PA.

Tanaka, F., et al., "Intratumoral Injection of Dendritic Cells After Treatment of Anticancer Drugs Induces Tumor-Specific Antitumor Effect in vivo," *Int. J. Cancer*, 101, pp. 265-269, 2002. Published by Wiley-Liss, Inc.

Website: http://syfpeithi.bmi-heidelberg.com/.

Website: http://syfpeithi.bmi-heidelberg.com/Scripts/MHCServer.dll/EpPredict.htm.

Gomez-Nunez et al., "Peptide binding motif predictive algorithms correspond with experimental binding of leukemia vaccine candidate peptides to HLA-A*0201 Molecules," *Leuk Res* 30: 1293-1298 (2006).

Mishra, et al., "Prediction and Molecular Modeling of T-cell Epitopes Derived from Placental Alkaline Phosphatase for use in Cancer Immunotherapy," *J Biomol Struct Dyn* 24: 109-21 (2006).

Hassainya et al., "Identification of naturally processed HLA-A2-restricted proinsulin epitopes by reverse immunology." *Diabetes* 54: 2053-2059 (2005).

*Immunobiology: the immune system in health and disease*, Janeway et al., eds. Garland Science Publishing (New York, NY), p. 717 (2005).

Calin, G., et al., The difference between p53 mutation frequency in haematological and non-haematological malignancies: possible explanations. *Medical Hypotheses*, 53(4) 326-328 (1999).

Serakinci, N., et al., Telomerase activity in human leukemic cells with or without monosomy 7 or 7q-.*BMC Medical Genetics*, 3:11 (2002) (accessed via: http://www.biomedcentral.com/1471-2350/3/11 pp. 1-6).

* cited by examiner

Stimulation Cycle

Stimulation Cycle

CTL activities against PBMCs

CTL activities against monocytes

SEQUENCE LISTING

<160> NUMBER OF SEQ ID NOS: 179

<210> SEQ ID NO 1
<211> LENGTH: 9
<212> TYPE: PRT
<213> ORGANISM: Homo sapiens

<400> SEQUENCE: 1

Tyr Leu Ala Leu Cys Leu Cys Leu Ile
1               5

<210> SEQ ID NO 2
<211> LENGTH: 9
<212> TYPE: PRT
<213> ORGANISM: Homo sapiens

<400> SEQUENCE: 2

Ala Ile Ile Ser Gly Asp Ser Pro Val
1               5

<210> SEQ ID NO 3
<211> LENGTH: 9
<212> TYPE: PRT
<213> ORGANISM: Homo sapiens

<400> SEQUENCE: 3

Tyr Ile Ile Ser Gly Asp Ser Pro Val
1               5

<210> SEQ ID NO 4
<211> LENGTH: 364
<212> TYPE: PRT
<213> ORGANISM: Homo sapiens

<400> SEQUENCE: 4

Met Pro Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
                20                  25                  30

Glu Gly Leu Cys Val Leu Val Pro Cys Thr Phe Phe His Pro Ile Pro
            35                  40                  45

Tyr Tyr Asp Lys Asn Ser Pro Val His Gly Tyr Trp Phe Arg Glu Gly
        50                  55                  60

Ala Ile Ile Ser Gly Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
        115                 120                 125

Tyr Lys Ser Pro Gln Leu Ser Val His Val Thr Asp Leu Thr His Arg
    130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr

```
                180               185               190
His Ser Ser Val Leu Ile Ile Thr Pro Arg Pro Gln Asp His Gly Thr
        195                 200                 205
Asn Leu Thr Cys Gln Val Lys Phe Ala Gly Ala Gly Val Thr Thr Glu
        210                 215                 220
Arg Thr Ile Gln Leu Asn Val Thr Tyr Val Pro Gln Asn Pro Thr Thr
225                 230                 235                 240
Gly Ile Phe Pro Gly Asp Gly Ser Gly Lys Gln Glu Thr Arg Ala Gly
                245                 250                 255
Val Val His Gly Ala Ile Gly Gly Ala Gly Val Thr Ala Leu Leu Ala
            260                 265                 270
Leu Cys Leu Cys Leu Ile Phe Phe Ile Val Lys Thr His Arg Arg Lys
        275                 280                 285
Ala Ala Arg Thr Ala Val Gly Arg Asn Asp Thr His Pro Thr Thr Gly
        290                 295                 300
Ser Ala Ser Pro Lys His Gln Lys Lys Ser Lys Leu His Gly Pro Thr
305                 310                 315                 320
Glu Thr Ser Ser Cys Ser Gly Ala Ala Pro Thr Val Glu Met Asp Glu
                325                 330                 335
Glu Leu His Tyr Ala Ser Leu Asn Phe His Gly Met Asn Pro Ser Lys
            340                 345                 350
Asp Thr Ser Thr Glu Tyr Ser Glu Val Arg Thr Gln
        355                 360

<210> SEQ ID NO 5
<211> LENGTH: 1437
<212> TYPE: DNA
<213> ORGANISM: Homo sapiens

<400> SEQUENCE: 5
gcttcctcag acatgccgct gctgctactg ctgcccctgc tgtgggcagg ggccctggct      60
atggatccaa atttctggct gcaagtgcag gagtcagtga cggtacagga gggtttgtgc    120
gtcctcgtgc cctgcacttt cttccatccc atacccta   acgacaagaa ctccccagtt    180
catggttact ggttccggga aggagccatt atatccgggg actctccagt ggccacaaac    240
aagctagatc aagaagtaca ggaggagact cagggcagat ccgcctcct  tgggatccc     300
agtaggaaca actgctccct gagcatcgta gacgccagga ggagggataa tggttcatac    360
ttctttcgga tggagagagg aagtaccaaa tacagttaca atctccccca gctctctgtg    420
catgtgacag acttgaccca caggcccaaa atcctcatcc ctggcactct agaacccggc    480
cactccaaaa accttacctg ctctgtgtcc tgggcctgtg agcagggaac ccccgatc     540
ttctcctggt tgtcagctgc cccaccctcc ctgggcccca ggactactca ctcctcggtg    600
ctcataatca cccacggcc  caggaccac  ggcaccaacc tgacctgtca ggtgaagttc    660
gctggagctg gtgtgactac ggagagaacc atccagctca acgtcaccta tgttccacag    720
aacccaacaa ctggtatctt ccaggagat ggctcaggga acaagagac cagagcagga     780
ctggttcatg gggccattgg aggagctggt gttacagccc tgctcgctct tgtctctgc     840
ctcatcttct tcatagtgaa gacccacagg aggaaagcag ccaggacagc agtgggcagc    900
aatgacaccc accctaccac agggtcagcc tcccgaaac  accagaagaa ctccaagtta   960
catggcccca tgaaacctc  aagctgttca ggtgccgccc ctactgtgga gatggatgag   1020
gagctgcatt atgcttccct caactttcat gggatgaatc cttccaagga cacctccacc   1080
```

-continued

```
gaatactcag aggtcaggac ccagtgagga accctcaaga gcatcaggct cagctagaag    1140
atccacatcc tctacaggtc ggggaccaaa ggctgattct tggagattta actccccaca    1200
ggcaatgggt ttatagacat tatgtgagtt tcctgctata ttaacatcat cttgagactt    1260
tgcaagcaga gagtcgtgga atcaaatctg tgctctttca tttgctaagt gtatgatgtc    1320
acacaagctc cttaaccttc catgtctcca ttttcttctc tgtgaagtag gtataagaag    1380
tcctatctca tagggatgct gtgagcatta aataaaggta cacatggaaa acaccag       1437
```

<210> SEQ ID NO 6
<211> LENGTH: 9
<212> TYPE: PRT
<213> ORGANISM: Homo sapiens

<400> SEQUENCE: 6

Tyr Ile Ile Ser Gly Ile Ser Pro Val
1               5

<210> SEQ ID NO 7
<211> LENGTH: 9
<212> TYPE: PRT
<213> ORGANISM: Homo sapiens

<400> SEQUENCE: 7

Tyr Leu Ile Ser Gly Asp Ser Pro Val
1               5

<210> SEQ ID NO 8
<211> LENGTH: 9
<212> TYPE: PRT
<213> ORGANISM: Homo sapiens

<400> SEQUENCE: 8

Ala Leu Leu Ala Leu Cys Leu Cys Leu
1               5

<210> SEQ ID NO 9
<211> LENGTH: 9
<212> TYPE: PRT
<213> ORGANISM: Homo sapiens

<400> SEQUENCE: 9

Thr Ile Gln Leu Asn Val Thr Tyr Val
1               5

<210> SEQ ID NO 10
<211> LENGTH: 9
<212> TYPE: PRT
<213> ORGANISM: Homo sapiens

<400> SEQUENCE: 10

Tyr Ile Gly Ser Gly Asp Ser Pro Val
1               5

<210> SEQ ID NO 11
<211> LENGTH: 9
<212> TYPE: PRT
<213> ORGANISM: Homo sapiens

<400> SEQUENCE: 11

Tyr Ile Ile Ile Gly Asp Ser Pro Val
1               5

```
<210> SEQ ID NO 12
<211> LENGTH: 9
<212> TYPE: PRT
<213> ORGANISM: Homo sapiens

<400> SEQUENCE: 12

Tyr Ile Ile Leu Gly Asp Ser Pro Val
1               5

<210> SEQ ID NO 13
<211> LENGTH: 9
<212> TYPE: PRT
<213> ORGANISM: Homo sapiens

<400> SEQUENCE: 13

Tyr Ile Ile Ser Gly Asp Leu Pro Val
1               5

<210> SEQ ID NO 14
<211> LENGTH: 9
<212> TYPE: PRT
<213> ORGANISM: Homo sapiens

<400> SEQUENCE: 14

Tyr Ile Ile Ser Gly Asp Ser Trp Val
1               5

<210> SEQ ID NO 15
<211> LENGTH: 9
<212> TYPE: PRT
<213> ORGANISM: Homo sapiens

<400> SEQUENCE: 15

Tyr Ile Ile Ser Gly Asp Ser Pro Leu
1               5

<210> SEQ ID NO 16
<211> LENGTH: 9
<212> TYPE: PRT
<213> ORGANISM: Homo sapiens

<400> SEQUENCE: 16

Ala Leu Ile Ser Gly Asp Ser Pro Val
1               5

<210> SEQ ID NO 17
<211> LENGTH: 8
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X at the first position indicates the presence
      of an anchor amino acid, i.e. a Y
<220> FEATURE:
<221> NAME/KEY: MISC_FEATURE
<222> LOCATION: (2)..(8)
<223> OTHER INFORMATION: X can be any residue

<400> SEQUENCE: 17

Xaa Xaa Xaa Xaa Xaa Xaa Xaa Xaa
1               5

<210> SEQ ID NO 18
<211> LENGTH: 8
<212> TYPE: PRT
<213> ORGANISM: Homo sapiens
```

```
<220> FEATURE:
<221> NAME/KEY: MISC_FEATURE
<222> LOCATION: (1)..(1)
<223> OTHER INFORMATION: X can be any residue
<220> FEATURE:
<221> NAME/KEY: MISC_FEATURE
<222> LOCATION: (2)..(2)
<223> OTHER INFORMATION: X at the second position indicates the presence
      of an anchor amino acid, i.e. a L, M or I
<220> FEATURE:
<221> NAME/KEY: MISC_FEATURE
<222> LOCATION: (3)..(8)
<223> OTHER INFORMATION: X can be any residue

<400> SEQUENCE: 18

Xaa Xaa Xaa Xaa Xaa Xaa Xaa Xaa
1               5

<210> SEQ ID NO 19
<211> LENGTH: 8
<212> TYPE: PRT
<213> ORGANISM: Homo sapiens
<220> FEATURE:
<221> NAME/KEY: MISC_FEATURE
<222> LOCATION: (1)..(3)
<223> OTHER INFORMATION: X can be any residue
<220> FEATURE:
<221> NAME/KEY: MISC_FEATURE
<222> LOCATION: (4)..(4)
<223> OTHER INFORMATION: X at the fourth position indicates the presence
      of an anchor amino acid, i.e. a E, K or S
<220> FEATURE:
<221> NAME/KEY: MISC_FEATURE
<222> LOCATION: (5)..(8)
<223> OTHER INFORMATION: X can be any residue

<400> SEQUENCE: 19

Xaa Xaa Xaa Xaa Xaa Xaa Xaa Xaa
1               5

<210> SEQ ID NO 20
<211> LENGTH: 8
<212> TYPE: PRT
<213> ORGANISM: Homo sapiens
<220> FEATURE:
<221> NAME/KEY: MISC_FEATURE
<222> LOCATION: (1)..(7)
<223> OTHER INFORMATION: X can be any residue
<220> FEATURE:
<221> NAME/KEY: MISC_FEATURE
<222> LOCATION: (8)..(8)
<223> OTHER INFORMATION: X at the eighth position indicates the presence
      of an anchor amino acid, i.e. a K

<400> SEQUENCE: 20

Xaa Xaa Xaa Xaa Xaa Xaa Xaa Xaa
1               5

<210> SEQ ID NO 21
<211> LENGTH: 9
<212> TYPE: PRT
<213> ORGANISM: Homo sapiens
<220> FEATURE:
<221> NAME/KEY: MISC_FEATURE
<222> LOCATION: (1)..(8)
<223> OTHER INFORMATION: X can be any residue
<220> FEATURE:
<221> NAME/KEY: MISC_FEATURE
<222> LOCATION: (9)..(9)
<223> OTHER INFORMATION: X at the ninth position indicates the presence
      of an anchor amino acid, i.e. a V, T, L or I

<400> SEQUENCE: 21
```

-continued

Xaa Xaa Xaa Xaa Xaa Xaa Xaa Xaa Xaa
1               5

<210> SEQ ID NO 22
<211> LENGTH: 8
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X at the first position indicates the presence
      of an anchor amino acid, i.e. a Y
<220> FEATURE:
<221> NAME/KEY: MISC_FEATURE
<222> LOCATION: (2)..(2)
<223> OTHER INFORMATION: X at the second position indicates the presence
      of an anchor amino acid, i.e. a L, M or I
<220> FEATURE:
<221> NAME/KEY: MISC_FEATURE
<222> LOCATION: (3)..(8)
<223> OTHER INFORMATION: X can be any residue

<400> SEQUENCE: 22

Xaa Xaa Xaa Xaa Xaa Xaa Xaa Xaa
1               5

<210> SEQ ID NO 23
<211> LENGTH: 8
<212> TYPE: PRT
<213> ORGANISM: Homo sapiens
<220> FEATURE:
<221> NAME/KEY: MISC_FEATURE
<222> LOCATION: (1)..(3)
<223> OTHER INFORMATION: X can be any residue
<220> FEATURE:
<221> NAME/KEY: MISC_FEATURE
<222> LOCATION: (4)..(4)
<223> OTHER INFORMATION: X at the fourth position indicates the presence
      of an anchor amino acid, i.e. a E, K or S
<220> FEATURE:
<221> NAME/KEY: MISC_FEATURE
<222> LOCATION: (5)..(8)
<223> OTHER INFORMATION: X can be any residue

<400> SEQUENCE: 23

Xaa Xaa Xaa Xaa Xaa Xaa Xaa Xaa
1               5

<210> SEQ ID NO 24
<211> LENGTH: 9
<212> TYPE: PRT
<213> ORGANISM: Homo sapiens
<220> FEATURE:
<221> NAME/KEY: MISC_FEATURE
<222> LOCATION: (1)..(7)
<223> OTHER INFORMATION: X can be any residue
<220> FEATURE:
<221> NAME/KEY: MISC_FEATURE
<222> LOCATION: (8)..(8)
<223> OTHER INFORMATION: X at the eighth position indicates the presence
      of an anchor amino acid, i.e. a K
<220> FEATURE:
<221> NAME/KEY: MISC_FEATURE
<222> LOCATION: (9)..(9)
<223> OTHER INFORMATION: X can be any residue and is optional

<400> SEQUENCE: 24

Xaa Xaa Xaa Xaa Xaa Xaa Xaa Xaa Xaa
1               5

<210> SEQ ID NO 25

```
<211> LENGTH: 9
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X at the first position indicates the presence
      of an anchor amino acid, i.e. a Y
<220> FEATURE:
<221> NAME/KEY: MISC_FEATURE
<222> LOCATION: (2)..(8)
<223> OTHER INFORMATION: X can be any residue
<220> FEATURE:
<221> NAME/KEY: MISC_FEATURE
<222> LOCATION: (9)..(9)
<223> OTHER INFORMATION: X at the eighth position indicates the presence
      of an anchor amino acid, i.e. a V, T, L or I

<400> SEQUENCE: 25

Xaa Xaa Xaa Xaa Xaa Xaa Xaa Xaa Xaa
1               5

<210> SEQ ID NO 26
<211> LENGTH: 8
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X at the first position indicates the presence
      of an anchor amino acid, i.e. a Y
<220> FEATURE:
<221> NAME/KEY: MISC_FEATURE
<222> LOCATION: (2)..(2)
<223> OTHER INFORMATION: X at the second position indicates the presence
      of an anchor amino acid, i.e. a L, M, or I
<220> FEATURE:
<221> NAME/KEY: MISC_FEATURE
<222> LOCATION: (3)..(3)
<223> OTHER INFORMATION: X can be any residue
<220> FEATURE:
<221> NAME/KEY: MISC_FEATURE
<222> LOCATION: (4)..(4)
<223> OTHER INFORMATION: X at the fourth position indicates the presence
      of an anchor amino acid, i.e. a E, K or S
<220> FEATURE:
<221> NAME/KEY: MISC_FEATURE
<222> LOCATION: (5)..(8)
<223> OTHER INFORMATION: X can be any residue

<400> SEQUENCE: 26

Xaa Xaa Xaa Xaa Xaa Xaa Xaa Xaa
1               5

<210> SEQ ID NO 27
<211> LENGTH: 8
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X at the first position indicates the presence
      of an anchor amino acid, i.e. a Y
<220> FEATURE:
<221> NAME/KEY: MISC_FEATURE
<222> LOCATION: (2)..(2)
<223> OTHER INFORMATION: X at the second position indicates the presence
      of an anchor amino acid, i.e. a L, M or I
<220> FEATURE:
<221> NAME/KEY: MISC_FEATURE
<222> LOCATION: (3)..(7)
<223> OTHER INFORMATION: X can be any residue
<220> FEATURE:
<221> NAME/KEY: MISC_FEATURE
<222> LOCATION: (8)..(8)
```

```
<223> OTHER INFORMATION: X at the eighth position indicates the presence
      of an anchor amino acid, i.e. a K

<400> SEQUENCE: 27

Xaa Xaa Xaa Xaa Xaa Xaa Xaa Xaa
1               5

<210> SEQ ID NO 28
<211> LENGTH: 9
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X at the first position indicates the presence
      of an anchor amino acid, i.e. a Y
<220> FEATURE:
<221> NAME/KEY: MISC_FEATURE
<222> LOCATION: (2)..(2)
<223> OTHER INFORMATION: X at the second position indicates the presence
      of an anchor amino acid, i.e. a L, M or I
<220> FEATURE:
<221> NAME/KEY: MISC_FEATURE
<222> LOCATION: (3)..(8)
<223> OTHER INFORMATION: X can be any residue
<220> FEATURE:
<221> NAME/KEY: MISC_FEATURE
<222> LOCATION: (9)..(9)
<223> OTHER INFORMATION: X at the ninth position indicates the presence
      of an anchor amino acid, i.e. a V, T, L or I

<400> SEQUENCE: 28

Xaa Xaa Xaa Xaa Xaa Xaa Xaa Xaa Xaa
1               5

<210> SEQ ID NO 29
<211> LENGTH: 8
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X at the first position indicates the presence
      of an anchor amino acid, i.e. a Y
<220> FEATURE:
<221> NAME/KEY: MISC_FEATURE
<222> LOCATION: (2)..(2)
<223> OTHER INFORMATION: X at the second position indicates the presence
      of an anchor amino acid, i.e. a L, M or I
<220> FEATURE:
<221> NAME/KEY: MISC_FEATURE
<222> LOCATION: (3)..(7)
<223> OTHER INFORMATION: X can be any residue
<220> FEATURE:
<221> NAME/KEY: MISC_FEATURE
<222> LOCATION: (8)..(8)
<223> OTHER INFORMATION: X at the eighth position indicates the presence
      of an anchor amino acid, i.e. a K

<400> SEQUENCE: 29

Xaa Xaa Xaa Xaa Xaa Xaa Xaa Xaa
1               5

<210> SEQ ID NO 30
<211> LENGTH: 9
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X at the first position indicates the presence
      of an anchor amino acid, i.e. a Y
<220> FEATURE:
```

```
<221> NAME/KEY: MISC_FEATURE
<222> LOCATION: (2)..(2)
<223> OTHER INFORMATION: X at the second position indicates the presence
      of an anchor amino acid, i.e. a L, M or I
<220> FEATURE:
<221> NAME/KEY: MISC_FEATURE
<222> LOCATION: (3)..(3)
<223> OTHER INFORMATION: X can be any residue
<220> FEATURE:
<221> NAME/KEY: MISC_FEATURE
<222> LOCATION: (4)..(4)
<223> OTHER INFORMATION: X at the fourth position indicates the presence
      of an anchor amino acid, i.e. a E, K or S
<220> FEATURE:
<221> NAME/KEY: MISC_FEATURE
<222> LOCATION: (5)..(8)
<223> OTHER INFORMATION: X can be any residue
<220> FEATURE:
<221> NAME/KEY: MISC_FEATURE
<222> LOCATION: (9)..(9)
<223> OTHER INFORMATION: X at the ninth position indicates the presence
      of an anchor amino acid, i.e. a V, T, L or I

<400> SEQUENCE: 30

Xaa Xaa Xaa Xaa Xaa Xaa Xaa Xaa Xaa
1               5

<210> SEQ ID NO 31
<211> LENGTH: 9
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X at the first position indicates the presence
      of an anchor amino acid, i.e. a Y
<220> FEATURE:
<221> NAME/KEY: MISC_FEATURE
<222> LOCATION: (2)..(2)
<223> OTHER INFORMATION: X at the second position indicates the presence
      of an anchor amino acid, i.e. a L, M or I
<220> FEATURE:
<221> NAME/KEY: MISC_FEATURE
<222> LOCATION: (3)..(3)
<223> OTHER INFORMATION: X can be any residue
<220> FEATURE:
<221> NAME/KEY: MISC_FEATURE
<222> LOCATION: (4)..(4)
<223> OTHER INFORMATION: X at the fourth position indicates the presence
      of an anchor amino acid, i.e. a E, K or S
<220> FEATURE:
<221> NAME/KEY: MISC_FEATURE
<222> LOCATION: (5)..(7)
<223> OTHER INFORMATION: X can be any residue
<220> FEATURE:
<221> NAME/KEY: MISC_FEATURE
<222> LOCATION: (8)..(8)
<223> OTHER INFORMATION: X at the eighth position indicates the presence
      of an anchor amino acid, i.e. a K
<220> FEATURE:
<221> NAME/KEY: MISC_FEATURE
<222> LOCATION: (9)..(9)
<223> OTHER INFORMATION: X at the ninth position indicates the presence
      of an anchor amino acid, i.e. a V, T, L or I

<400> SEQUENCE: 31

Xaa Xaa Xaa Xaa Xaa Xaa Xaa Xaa Xaa
1               5

<210> SEQ ID NO 32
<211> LENGTH: 8
<212> TYPE: PRT
<213> ORGANISM: Homo sapiens
<220> FEATURE:
<221> NAME/KEY: MISC_FEATURE
```

```
<222> LOCATION: (1)..(1)
<223> OTHER INFORMATION: X can be any residue
<220> FEATURE:
<221> NAME/KEY: MISC_FEATURE
<222> LOCATION: (2)..(2)
<223> OTHER INFORMATION: X at the second position indicates the presence
      of an anchor amino acid, i.e. a L, M or I
<220> FEATURE:
<221> NAME/KEY: MISC_FEATURE
<222> LOCATION: (3)..(3)
<223> OTHER INFORMATION: X can be any residue
<220> FEATURE:
<221> NAME/KEY: MISC_FEATURE
<222> LOCATION: (4)..(4)
<223> OTHER INFORMATION: X at the fourth position indicates the presence
      of an anchor amino acid, i.e. a E, K or S
<220> FEATURE:
<221> NAME/KEY: MISC_FEATURE
<222> LOCATION: (5)..(8)
<223> OTHER INFORMATION: X can be any residue

<400> SEQUENCE: 32

Xaa Xaa Xaa Xaa Xaa Xaa Xaa Xaa
1               5

<210> SEQ ID NO 33
<211> LENGTH: 8
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X can be any residue
<220> FEATURE:
<221> NAME/KEY: MISC_FEATURE
<222> LOCATION: (2)..(2)
<223> OTHER INFORMATION: X at the second position indicates the presence
      of an anchor amino acid, i.e. a L, M or I
<220> FEATURE:
<221> NAME/KEY: MISC_FEATURE
<222> LOCATION: (3)..(7)
<223> OTHER INFORMATION: X can be any residue
<220> FEATURE:
<221> NAME/KEY: MISC_FEATURE
<222> LOCATION: (8)..(8)
<223> OTHER INFORMATION: X at the eighth position indicates the presence
      of an anchor amino acid, i.e. a K

<400> SEQUENCE: 33

Xaa Xaa Xaa Xaa Xaa Xaa Xaa Xaa
1               5

<210> SEQ ID NO 34
<211> LENGTH: 9
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X can be any residue
<220> FEATURE:
<221> NAME/KEY: MISC_FEATURE
<222> LOCATION: (2)..(2)
<223> OTHER INFORMATION: X at the second position indicates the presence
      of an anchor amino acid, i.e. a L, M or I
<220> FEATURE:
<221> NAME/KEY: MISC_FEATURE
<222> LOCATION: (3)..(8)
<223> OTHER INFORMATION: X can be any residue
<220> FEATURE:
<221> NAME/KEY: MISC_FEATURE
<222> LOCATION: (9)..(9)
<223> OTHER INFORMATION: X at the ninth position indicates the presence
      of an anchor amino acid, i.e. a V, T, L or I
```

```
<400> SEQUENCE: 34

Xaa Xaa Xaa Xaa Xaa Xaa Xaa Xaa Xaa
1               5

<210> SEQ ID NO 35
<211> LENGTH: 8
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X can be any residue
<220> FEATURE:
<221> NAME/KEY: MISC_FEATURE
<222> LOCATION: (2)..(2)
<223> OTHER INFORMATION: X at the second position indicates the presence
      of an anchor amino acid, i.e. a L, M or I
<220> FEATURE:
<221> NAME/KEY: MISC_FEATURE
<222> LOCATION: (3)..(3)
<223> OTHER INFORMATION: X can be any residue
<220> FEATURE:
<221> NAME/KEY: MISC_FEATURE
<222> LOCATION: (3)..(7)
<223> OTHER INFORMATION: X can be any residue
<220> FEATURE:
<221> NAME/KEY: MISC_FEATURE
<222> LOCATION: (4)..(4)
<223> OTHER INFORMATION: X at the fourth position indicates the presence
      of an anchor amino acid, i.e. a E, K or S
<220> FEATURE:
<221> NAME/KEY: MISC_FEATURE
<222> LOCATION: (8)..(8)
<223> OTHER INFORMATION: X at the eighth position indicates the presence
      of an anchor amino acid, i.e. a K

<400> SEQUENCE: 35

Xaa Xaa Xaa Xaa Xaa Xaa Xaa Xaa
1               5

<210> SEQ ID NO 36
<211> LENGTH: 9
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X can be any residue
<220> FEATURE:
<221> NAME/KEY: MISC_FEATURE
<222> LOCATION: (2)..(2)
<223> OTHER INFORMATION: X at the second position indicates the presence
      of an anchor amino acid, i.e. a L, M or I
<220> FEATURE:
<221> NAME/KEY: MISC_FEATURE
<222> LOCATION: (3)..(3)
<223> OTHER INFORMATION: X can be any residue
<220> FEATURE:
<221> NAME/KEY: MISC_FEATURE
<222> LOCATION: (4)..(4)
<223> OTHER INFORMATION: X at the eighth position indicates the presence
      of an anchor amino acid, i.e. a E, K or S
<220> FEATURE:
<221> NAME/KEY: MISC_FEATURE
<222> LOCATION: (5)..(8)
<223> OTHER INFORMATION: X can be any residue
<220> FEATURE:
<221> NAME/KEY: MISC_FEATURE
<222> LOCATION: (9)..(9)
<223> OTHER INFORMATION: X at the eighth position indicates the presence
      of an anchor amino acid, i.e. a V, T, L or I

<400> SEQUENCE: 36

Xaa Xaa Xaa Xaa Xaa Xaa Xaa Xaa Xaa
```

```
<210> SEQ ID NO 37
<211> LENGTH: 9
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X can be any residue
<220> FEATURE:
<221> NAME/KEY: MISC_FEATURE
<222> LOCATION: (2)..(2)
<223> OTHER INFORMATION: X at the second position indicates the presence
      of an anchor amino acid, i.e. a L, M or I
<220> FEATURE:
<221> NAME/KEY: MISC_FEATURE
<222> LOCATION: (3)..(3)
<223> OTHER INFORMATION: X can be any residue
<220> FEATURE:
<221> NAME/KEY: MISC_FEATURE
<222> LOCATION: (4)..(4)
<223> OTHER INFORMATION: X at the fourth position indicates the presence
      of an anchor amino acid, i.e. a E, K or S
<220> FEATURE:
<221> NAME/KEY: MISC_FEATURE
<222> LOCATION: (5)..(7)
<223> OTHER INFORMATION: X can be any residue
<220> FEATURE:
<221> NAME/KEY: MISC_FEATURE
<222> LOCATION: (8)..(8)
<223> OTHER INFORMATION: X at the eighth position indicates the presence
      of an anchor amino acid, i.e. a K
<220> FEATURE:
<221> NAME/KEY: MISC_FEATURE
<222> LOCATION: (9)..(9)
<223> OTHER INFORMATION: X at the ninth position indicates the presence
      of an anchor amino acid, i.e. a V, T, L or I

<400> SEQUENCE: 37

Xaa Xaa Xaa Xaa Xaa Xaa Xaa Xaa Xaa
1               5

<210> SEQ ID NO 38
<211> LENGTH: 8
<212> TYPE: PRT
<213> ORGANISM: Homo sapiens
<220> FEATURE:
<221> NAME/KEY: MISC_FEATURE
<222> LOCATION: (1)..(3)
<223> OTHER INFORMATION: X can be any residue
<220> FEATURE:
<221> NAME/KEY: MISC_FEATURE
<222> LOCATION: (4)..(4)
<223> OTHER INFORMATION: X at the fourth position indicates the presence
      of an anchor amino acid, i.e. a E, K or S
<220> FEATURE:
<221> NAME/KEY: MISC_FEATURE
<222> LOCATION: (5)..(7)
<223> OTHER INFORMATION: X can be any residue
<220> FEATURE:
<221> NAME/KEY: MISC_FEATURE
<222> LOCATION: (8)..(8)
<223> OTHER INFORMATION: X at the eighth position indicates the presence
      of an anchor amino acid, i.e. a K

<400> SEQUENCE: 38

Xaa Xaa Xaa Xaa Xaa Xaa Xaa Xaa
1               5

<210> SEQ ID NO 39
<211> LENGTH: 9
<212> TYPE: PRT
<213> ORGANISM: Homo sapiens
```

```
<220> FEATURE:
<221> NAME/KEY: MISC_FEATURE
<222> LOCATION: (1)..(3)
<223> OTHER INFORMATION: X can be any residue
<220> FEATURE:
<221> NAME/KEY: MISC_FEATURE
<222> LOCATION: (4)..(4)
<223> OTHER INFORMATION: X at the fourth position indicates the presence
      of an anchor amino acid, i.e. a E, K or S
<220> FEATURE:
<221> NAME/KEY: MISC_FEATURE
<222> LOCATION: (5)..(8)
<223> OTHER INFORMATION: X can be any residue
<220> FEATURE:
<221> NAME/KEY: MISC_FEATURE
<222> LOCATION: (9)..(9)
<223> OTHER INFORMATION: X at the ninth position indicates the presence
      of an anchor amino acid, i.e. a V, T, L or I

<400> SEQUENCE: 39

Xaa Xaa Xaa Xaa Xaa Xaa Xaa Xaa Xaa
1               5

<210> SEQ ID NO 40
<211> LENGTH: 9
<212> TYPE: PRT
<213> ORGANISM: Homo sapiens
<220> FEATURE:
<221> NAME/KEY: MISC_FEATURE
<222> LOCATION: (1)..(3)
<223> OTHER INFORMATION: X can be any residue
<220> FEATURE:
<221> NAME/KEY: MISC_FEATURE
<222> LOCATION: (4)..(4)
<223> OTHER INFORMATION: X at the fourth position indicates the presence
      of an anchor amino acid, i.e. a E, K or S
<220> FEATURE:
<221> NAME/KEY: MISC_FEATURE
<222> LOCATION: (5)..(7)
<223> OTHER INFORMATION: X can be any residue
<220> FEATURE:
<221> NAME/KEY: MISC_FEATURE
<222> LOCATION: (8)..(8)
<223> OTHER INFORMATION: X at the eighth position indicates the presence
      of an anchor amino acid, i.e. a K
<220> FEATURE:
<221> NAME/KEY: MISC_FEATURE
<222> LOCATION: (9)..(9)
<223> OTHER INFORMATION: X at the ninth position indicates the presence
      of an anchor amino acid, i.e. a V, T, L or I

<400> SEQUENCE: 40

Xaa Xaa Xaa Xaa Xaa Xaa Xaa Xaa Xaa
1               5

<210> SEQ ID NO 41
<211> LENGTH: 9
<212> TYPE: PRT
<213> ORGANISM: Homo sapiens
<220> FEATURE:
<221> NAME/KEY: MISC_FEATURE
<222> LOCATION: (1)..(7)
<223> OTHER INFORMATION: X can be any residue
<220> FEATURE:
<221> NAME/KEY: MISC_FEATURE
<222> LOCATION: (8)..(8)
<223> OTHER INFORMATION: X at the eighth position indicates the presence
      of an anchor amino acid, i.e. a K
<220> FEATURE:
<221> NAME/KEY: MISC_FEATURE
<222> LOCATION: (9)..(9)
<223> OTHER INFORMATION: X at the ninth position indicates the presence
      of an anchor amino acid, i.e. a V, T, L or I

<400> SEQUENCE: 41
```

Xaa Xaa Xaa Xaa Xaa Xaa Xaa Xaa Xaa
1               5

<210> SEQ ID NO 42
<211> LENGTH: 9
<212> TYPE: PRT
<213> ORGANISM: Homo sapiens

<400> SEQUENCE: 42

Leu Leu Ala Leu Cys Leu Cys Leu Ile
1               5

<210> SEQ ID NO 43
<211> LENGTH: 9
<212> TYPE: PRT
<213> ORGANISM: Homo sapiens

<400> SEQUENCE: 43

Pro Leu Leu Leu Leu Leu Pro Leu Leu
1               5

<210> SEQ ID NO 44
<211> LENGTH: 9
<212> TYPE: PRT
<213> ORGANISM: Homo sapiens

<400> SEQUENCE: 44

Leu Leu Leu Leu Pro Leu Leu Trp Ala
1               5

<210> SEQ ID NO 45
<211> LENGTH: 9
<212> TYPE: PRT
<213> ORGANISM: Homo sapiens

<400> SEQUENCE: 45

Gln Leu Ser Val His Val Thr Asp Leu
1               5

<210> SEQ ID NO 46
<211> LENGTH: 9
<212> TYPE: PRT
<213> ORGANISM: Homo sapiens

<400> SEQUENCE: 46

Cys Leu Ile Phe Phe Ile Val Lys Thr
1               5

<210> SEQ ID NO 47
<211> LENGTH: 9
<212> TYPE: PRT
<213> ORGANISM: Homo sapiens

<400> SEQUENCE: 47

Ile Leu Ile Pro Gly Thr Leu Glu Pro
1               5

<210> SEQ ID NO 48
<211> LENGTH: 9
<212> TYPE: PRT
<213> ORGANISM: Homo sapiens

<400> SEQUENCE: 48

Leu Leu Leu Pro Leu Leu Trp Ala Gly 1               5

<210> SEQ ID NO 49
<211> LENGTH: 9
<212> TYPE: PRT
<213> ORGANISM: Homo sapiens

<400> SEQUENCE: 49

Thr Val Gln Glu Gly Leu Cys Val Leu
1               5

<210> SEQ ID NO 50
<211> LENGTH: 9
<212> TYPE: PRT
<213> ORGANISM: Homo sapiens

<400> SEQUENCE: 50

Trp Leu Ser Ala Ala Pro Thr Ser Leu
1               5

<210> SEQ ID NO 51
<211> LENGTH: 9
<212> TYPE: PRT
<213> ORGANISM: Homo sapiens

<400> SEQUENCE: 51

Leu Leu Trp Ala Gly Ala Leu Ala Met
1               5

<210> SEQ ID NO 52
<211> LENGTH: 9
<212> TYPE: PRT
<213> ORGANISM: Homo sapiens

<400> SEQUENCE: 52

Gly Leu Cys Val Leu Val Pro Cys Thr
1               5

<210> SEQ ID NO 53
<211> LENGTH: 9
<212> TYPE: PRT
<213> ORGANISM: Homo sapiens

<400> SEQUENCE: 53

Leu Leu Pro Leu Leu Trp Ala Gly Ala
1               5

<210> SEQ ID NO 54
<211> LENGTH: 9
<212> TYPE: PRT
<213> ORGANISM: Homo sapiens

<400> SEQUENCE: 54

Ala Thr Asn Lys Leu Asp Gln Glu Val
1               5

<210> SEQ ID NO 55
<211> LENGTH: 9
<212> TYPE: PRT
<213> ORGANISM: Homo sapiens

<400> SEQUENCE: 55

Ala Ile Gly Gly Ala Gly Val Thr Ala
1               5

```
<210> SEQ ID NO 56
<211> LENGTH: 9
<212> TYPE: PRT
<213> ORGANISM: Homo sapiens

<400> SEQUENCE: 56

Cys Leu Cys Leu Ile Phe Phe Ile Val
1               5

<210> SEQ ID NO 57
<211> LENGTH: 9
<212> TYPE: PRT
<213> ORGANISM: Homo sapiens

<400> SEQUENCE: 57

Leu Ala Met Asp Pro Asn Phe Trp Leu
1               5

<210> SEQ ID NO 58
<211> LENGTH: 9
<212> TYPE: PRT
<213> ORGANISM: Homo sapiens

<400> SEQUENCE: 58

Ile Gly Gly Ala Gly Val Thr Ala Leu
1               5

<210> SEQ ID NO 59
<211> LENGTH: 9
<212> TYPE: PRT
<213> ORGANISM: Homo sapiens

<400> SEQUENCE: 59

Gly Gly Ala Gly Val Thr Ala Leu Leu
1               5

<210> SEQ ID NO 60
<211> LENGTH: 9
<212> TYPE: PRT
<213> ORGANISM: Homo sapiens

<400> SEQUENCE: 60

Val Thr Ala Leu Leu Ala Leu Cys Leu
1               5

<210> SEQ ID NO 61
<211> LENGTH: 9
<212> TYPE: PRT
<213> ORGANISM: Homo sapiens

<400> SEQUENCE: 61

Met Pro Leu Leu Leu Leu Leu Pro Leu
1               5

<210> SEQ ID NO 62
<211> LENGTH: 9
<212> TYPE: PRT
<213> ORGANISM: Homo sapiens

<400> SEQUENCE: 62

Val Thr Thr Glu Arg Thr Ile Gln Leu
1               5

<210> SEQ ID NO 63
```

```
<211> LENGTH: 9
<212> TYPE: PRT
<213> ORGANISM: Homo sapiens

<400> SEQUENCE: 63

Ala Gly Val Thr Ala Leu Leu Ala Leu
1               5

<210> SEQ ID NO 64
<211> LENGTH: 9
<212> TYPE: PRT
<213> ORGANISM: Homo sapiens

<400> SEQUENCE: 64

Lys Leu His Gly Pro Thr Glu Thr Ser
1               5

<210> SEQ ID NO 65
<211> LENGTH: 9
<212> TYPE: PRT
<213> ORGANISM: Homo sapiens

<400> SEQUENCE: 65

Ile Ile Ser Gly Asp Ser Pro Val Ala
1               5

<210> SEQ ID NO 66
<211> LENGTH: 9
<212> TYPE: PRT
<213> ORGANISM: Homo sapiens

<400> SEQUENCE: 66

Lys Leu Asp Gln Glu Val Gln Glu Glu
1               5

<210> SEQ ID NO 67
<211> LENGTH: 9
<212> TYPE: PRT
<213> ORGANISM: Homo sapiens

<400> SEQUENCE: 67

Asp Leu Thr His Arg Pro Lys Ile Leu
1               5

<210> SEQ ID NO 68
<211> LENGTH: 9
<212> TYPE: PRT
<213> ORGANISM: Homo sapiens

<400> SEQUENCE: 68

Asn Leu Thr Cys Ser Val Ser Trp Ala
1               5

<210> SEQ ID NO 69
<211> LENGTH: 9
<212> TYPE: PRT
<213> ORGANISM: Homo sapiens

<400> SEQUENCE: 69

Gly Thr Pro Pro Ile Phe Ser Trp Leu
1               5

<210> SEQ ID NO 70
<211> LENGTH: 9
<212> TYPE: PRT
```

<213> ORGANISM: Homo sapiens

<400> SEQUENCE: 70

Thr Thr His Ser Ser Val Leu Ile Ile
1               5

<210> SEQ ID NO 71
<211> LENGTH: 9
<212> TYPE: PRT
<213> ORGANISM: Homo sapiens

<400> SEQUENCE: 71

His Gly Ala Ile Gly Gly Ala Gly Val
1               5

<210> SEQ ID NO 72
<211> LENGTH: 9
<212> TYPE: PRT
<213> ORGANISM: Homo sapiens

<400> SEQUENCE: 72

Leu Cys Leu Cys Leu Ile Phe Phe Ile
1               5

<210> SEQ ID NO 73
<211> LENGTH: 9
<212> TYPE: PRT
<213> ORGANISM: Homo sapiens

<400> SEQUENCE: 73

Ser Cys Ser Gly Ala Ala Pro Thr Val
1               5

<210> SEQ ID NO 74
<211> LENGTH: 9
<212> TYPE: PRT
<213> ORGANISM: Homo sapiens

<400> SEQUENCE: 74

Leu Leu Leu Leu Leu Pro Leu Leu Trp
1               5

<210> SEQ ID NO 75
<211> LENGTH: 9
<212> TYPE: PRT
<213> ORGANISM: Homo sapiens

<400> SEQUENCE: 75

Leu Gln Val Gln Glu Ser Val Thr Val
1               5

<210> SEQ ID NO 76
<211> LENGTH: 9
<212> TYPE: PRT
<213> ORGANISM: Homo sapiens

<400> SEQUENCE: 76

Leu Gln Val Gln Glu Ser Val Thr Val
1               5

<210> SEQ ID NO 77
<211> LENGTH: 9
<212> TYPE: PRT
<213> ORGANISM: Homo sapiens

```
<400> SEQUENCE: 77

Leu Ile Pro Gly Thr Leu Glu Pro Gly
1               5

<210> SEQ ID NO 78
<211> LENGTH: 9
<212> TYPE: PRT
<213> ORGANISM: Homo sapiens

<400> SEQUENCE: 78

Ser Leu Gly Pro Arg Thr Thr His Ser
1               5

<210> SEQ ID NO 79
<211> LENGTH: 9
<212> TYPE: PRT
<213> ORGANISM: Homo sapiens

<400> SEQUENCE: 79

Asn Leu Thr Cys Gln Val Lys Phe Ala
1               5

<210> SEQ ID NO 80
<211> LENGTH: 9
<212> TYPE: PRT
<213> ORGANISM: Homo sapiens

<400> SEQUENCE: 80

Gly Ile Phe Pro Gly Asp Gly Ser Gly
1               5

<210> SEQ ID NO 81
<211> LENGTH: 9
<212> TYPE: PRT
<213> ORGANISM: Homo sapiens

<400> SEQUENCE: 81

Gly Lys Gln Glu Thr Arg Ala Gly Val
1               5

<210> SEQ ID NO 82
<211> LENGTH: 9
<212> TYPE: PRT
<213> ORGANISM: Homo sapiens

<400> SEQUENCE: 82

Val Val His Gly Ala Ile Gly Gly Ala
1               5

<210> SEQ ID NO 83
<211> LENGTH: 9
<212> TYPE: PRT
<213> ORGANISM: Homo sapiens

<400> SEQUENCE: 83

Ala Leu Cys Leu Cys Leu Ile Phe Phe
1               5

<210> SEQ ID NO 84
<211> LENGTH: 9
<212> TYPE: PRT
<213> ORGANISM: Homo sapiens

<400> SEQUENCE: 84
```

```
Glu Met Asp Glu Glu Leu His Tyr Ala
1               5

<210> SEQ ID NO 85
<211> LENGTH: 9
<212> TYPE: PRT
<213> ORGANISM: Homo sapiens

<400> SEQUENCE: 85

Leu Pro Leu Leu Trp Ala Gly Ala Leu
1               5

<210> SEQ ID NO 86
<211> LENGTH: 9
<212> TYPE: PRT
<213> ORGANISM: Homo sapiens

<400> SEQUENCE: 86

Pro Leu Leu Trp Ala Gly Ala Leu Ala
1               5

<210> SEQ ID NO 87
<211> LENGTH: 9
<212> TYPE: PRT
<213> ORGANISM: Homo sapiens

<400> SEQUENCE: 87

Ala Leu Ala Met Asp Pro Asn Phe Trp
1               5

<210> SEQ ID NO 88
<211> LENGTH: 9
<212> TYPE: PRT
<213> ORGANISM: Homo sapiens

<400> SEQUENCE: 88

Phe Trp Leu Gln Val Gln Glu Ser Val
1               5

<210> SEQ ID NO 89
<211> LENGTH: 9
<212> TYPE: PRT
<213> ORGANISM: Homo sapiens

<400> SEQUENCE: 89

Val Gln Glu Gly Leu Cys Val Leu Val
1               5

<210> SEQ ID NO 90
<211> LENGTH: 9
<212> TYPE: PRT
<213> ORGANISM: Homo sapiens

<400> SEQUENCE: 90

Val Leu Val Pro Cys Thr Phe Phe His
1               5

<210> SEQ ID NO 91
<211> LENGTH: 9
<212> TYPE: PRT
<213> ORGANISM: Homo sapiens

<400> SEQUENCE: 91

Arg Asn Asn Cys Ser Leu Ser Ile Val
1               5
```

```
<210> SEQ ID NO 92
<211> LENGTH: 9
<212> TYPE: PRT
<213> ORGANISM: Homo sapiens

<400> SEQUENCE: 92

Ser Tyr Lys Ser Pro Gln Leu Ser Val
1               5

<210> SEQ ID NO 93
<211> LENGTH: 9
<212> TYPE: PRT
<213> ORGANISM: Homo sapiens

<400> SEQUENCE: 93

Leu Thr His Arg Pro Lys Ile Leu Ile
1               5

<210> SEQ ID NO 94
<211> LENGTH: 9
<212> TYPE: PRT
<213> ORGANISM: Homo sapiens

<400> SEQUENCE: 94

Thr Leu Glu Pro Gly His Ser Lys Asn
1               5

<210> SEQ ID NO 95
<211> LENGTH: 9
<212> TYPE: PRT
<213> ORGANISM: Homo sapiens

<400> SEQUENCE: 95

Pro Ile Phe Ser Trp Leu Ser Ala Ala
1               5

<210> SEQ ID NO 96
<211> LENGTH: 9
<212> TYPE: PRT
<213> ORGANISM: Homo sapiens

<400> SEQUENCE: 96

Gln Val Lys Phe Ala Gly Ala Gly Val
1               5

<210> SEQ ID NO 97
<211> LENGTH: 9
<212> TYPE: PRT
<213> ORGANISM: Homo sapiens

<400> SEQUENCE: 97

Gly Ala Ile Gly Gly Ala Gly Val Thr
1               5

<210> SEQ ID NO 98
<211> LENGTH: 9
<212> TYPE: PRT
<213> ORGANISM: Homo sapiens

<400> SEQUENCE: 98

Leu Ile Phe Phe Ile Val Lys Thr His
1               5
```

```
<210> SEQ ID NO 99
<211> LENGTH: 9
<212> TYPE: PRT
<213> ORGANISM: Homo sapiens

<400> SEQUENCE: 99

Ser Gly Ala Ala Pro Thr Val Glu Met
1               5

<210> SEQ ID NO 100
<211> LENGTH: 9
<212> TYPE: PRT
<213> ORGANISM: Homo sapiens

<400> SEQUENCE: 100

Pro Thr Val Glu Met Asp Glu Glu Leu
1               5

<210> SEQ ID NO 101
<211> LENGTH: 9
<212> TYPE: PRT
<213> ORGANISM: Homo sapiens

<400> SEQUENCE: 101

Asp Thr Ser Thr Glu Tyr Ser Glu Val
1               5

<210> SEQ ID NO 102
<211> LENGTH: 9
<212> TYPE: PRT
<213> ORGANISM: Homo sapiens

<400> SEQUENCE: 102

Trp Leu Gln Val Gln Glu Ser Val Thr
1               5

<210> SEQ ID NO 103
<211> LENGTH: 9
<212> TYPE: PRT
<213> ORGANISM: Homo sapiens

<400> SEQUENCE: 103

Asp Ser Pro Val Ala Thr Asn Lys Leu
1               5

<210> SEQ ID NO 104
<211> LENGTH: 9
<212> TYPE: PRT
<213> ORGANISM: Homo sapiens

<400> SEQUENCE: 104

Arg Leu Leu Gly Asp Pro Ser Arg Asn
1               5

<210> SEQ ID NO 105
<211> LENGTH: 9
<212> TYPE: PRT
<213> ORGANISM: Homo sapiens

<400> SEQUENCE: 105

Leu Leu Gly Asp Pro Ser Arg Asn Asn
1               5

<210> SEQ ID NO 106
<211> LENGTH: 9
```

```
<212> TYPE: PRT
<213> ORGANISM: Homo sapiens

<400> SEQUENCE: 106

Ser Arg Asn Asn Cys Ser Leu Ser Ile
1               5

<210> SEQ ID NO 107
<211> LENGTH: 9
<212> TYPE: PRT
<213> ORGANISM: Homo sapiens

<400> SEQUENCE: 107

Ser Leu Ser Ile Val Asp Ala Arg Arg
1               5

<210> SEQ ID NO 108
<211> LENGTH: 9
<212> TYPE: PRT
<213> ORGANISM: Homo sapiens

<400> SEQUENCE: 108

Lys Ser Pro Gln Leu Ser Val His Val
1               5

<210> SEQ ID NO 109
<211> LENGTH: 9
<212> TYPE: PRT
<213> ORGANISM: Homo sapiens

<400> SEQUENCE: 109

His Ser Lys Asn Leu Thr Cys Ser Val
1               5

<210> SEQ ID NO 110
<211> LENGTH: 9
<212> TYPE: PRT
<213> ORGANISM: Homo sapiens

<400> SEQUENCE: 110

Ala Cys Glu Gln Gly Thr Pro Pro Ile
1               5

<210> SEQ ID NO 111
<211> LENGTH: 9
<212> TYPE: PRT
<213> ORGANISM: Homo sapiens

<400> SEQUENCE: 111

Leu Ile Ile Thr Pro Arg Pro Gln Asp
1               5

<210> SEQ ID NO 112
<211> LENGTH: 9
<212> TYPE: PRT
<213> ORGANISM: Homo sapiens

<400> SEQUENCE: 112

Thr Arg Ala Gly Val Val His Gly Ala
1               5

<210> SEQ ID NO 113
<211> LENGTH: 9
<212> TYPE: PRT
<213> ORGANISM: Homo sapiens
```

```
<400> SEQUENCE: 113

Gly Met Asn Pro Ser Lys Asp Thr Ser
1               5

<210> SEQ ID NO 114
<211> LENGTH: 9
<212> TYPE: PRT
<213> ORGANISM: Homo sapiens

<400> SEQUENCE: 114

Tyr Trp Phe Arg Glu Gly Ala Ile Ile
1               5

<210> SEQ ID NO 115
<211> LENGTH: 9
<212> TYPE: PRT
<213> ORGANISM: Homo sapiens

<400> SEQUENCE: 115

Glu Thr Gln Gly Arg Phe Arg Leu Leu
1               5

<210> SEQ ID NO 116
<211> LENGTH: 9
<212> TYPE: PRT
<213> ORGANISM: Homo sapiens

<400> SEQUENCE: 116

Thr Asp Leu Thr His Arg Pro Lys Ile
1               5

<210> SEQ ID NO 117
<211> LENGTH: 9
<212> TYPE: PRT
<213> ORGANISM: Homo sapiens

<400> SEQUENCE: 117

Gly Thr Leu Glu Pro Gly His Ser Lys
1               5

<210> SEQ ID NO 118
<211> LENGTH: 9
<212> TYPE: PRT
<213> ORGANISM: Homo sapiens

<400> SEQUENCE: 118

Leu Glu Pro Gly His Ser Lys Asn Leu
1               5

<210> SEQ ID NO 119
<211> LENGTH: 9
<212> TYPE: PRT
<213> ORGANISM: Homo sapiens

<400> SEQUENCE: 119

Gly Pro Arg Thr Thr His Ser Ser Val
1               5

<210> SEQ ID NO 120
<211> LENGTH: 9
<212> TYPE: PRT
<213> ORGANISM: Homo sapiens

<400> SEQUENCE: 120
```

Arg Thr Thr His Ser Ser Val Leu Ile
1               5

<210> SEQ ID NO 121
<211> LENGTH: 9
<212> TYPE: PRT
<213> ORGANISM: Homo sapiens

<400> SEQUENCE: 121

Val Leu Ile Ile Thr Pro Arg Pro Gln
1               5

<210> SEQ ID NO 122
<211> LENGTH: 9
<212> TYPE: PRT
<213> ORGANISM: Homo sapiens

<400> SEQUENCE: 122

Lys Phe Ala Gly Ala Gly Val Thr Thr
1               5

<210> SEQ ID NO 123
<211> LENGTH: 9
<212> TYPE: PRT
<213> ORGANISM: Homo sapiens

<400> SEQUENCE: 123

Phe Ala Gly Ala Gly Val Thr Thr Glu
1               5

<210> SEQ ID NO 124
<211> LENGTH: 9
<212> TYPE: PRT
<213> ORGANISM: Homo sapiens

<400> SEQUENCE: 124

Gln Leu Asn Val Thr Tyr Val Pro Gln
1               5

<210> SEQ ID NO 125
<211> LENGTH: 9
<212> TYPE: PRT
<213> ORGANISM: Homo sapiens

<400> SEQUENCE: 125

Val Pro Gln Asn Pro Thr Thr Gly Ile
1               5

<210> SEQ ID NO 126
<211> LENGTH: 9
<212> TYPE: PRT
<213> ORGANISM: Homo sapiens

<400> SEQUENCE: 126

Arg Ala Gly Val Val His Gly Ala Ile
1               5

<210> SEQ ID NO 127
<211> LENGTH: 9
<212> TYPE: PRT
<213> ORGANISM: Homo sapiens

<400> SEQUENCE: 127

Arg Thr Ala Val Gly Arg Asn Asp Thr

```
<210> SEQ ID NO 128
<211> LENGTH: 9
<212> TYPE: PRT
<213> ORGANISM: Homo sapiens

<400> SEQUENCE: 128

Asp Thr His Pro Thr Thr Gly Ser Ala
1               5

<210> SEQ ID NO 129
<211> LENGTH: 9
<212> TYPE: PRT
<213> ORGANISM: Homo sapiens

<400> SEQUENCE: 129

Gly Ala Ala Pro Thr Val Glu Met Asp
1               5

<210> SEQ ID NO 130
<211> LENGTH: 9
<212> TYPE: PRT
<213> ORGANISM: Homo sapiens

<400> SEQUENCE: 130

Leu Trp Ala Gly Ala Leu Ala Met Asp
1               5

<210> SEQ ID NO 131
<211> LENGTH: 9
<212> TYPE: PRT
<213> ORGANISM: Homo sapiens

<400> SEQUENCE: 131

Ala Met Asp Pro Asn Phe Trp Leu Gln
1               5

<210> SEQ ID NO 132
<211> LENGTH: 9
<212> TYPE: PRT
<213> ORGANISM: Homo sapiens

<400> SEQUENCE: 132

Met Asp Pro Asn Phe Trp Leu Gln Val
1               5

<210> SEQ ID NO 133
<211> LENGTH: 9
<212> TYPE: PRT
<213> ORGANISM: Homo sapiens

<400> SEQUENCE: 133

Lys Tyr Ser Tyr Lys Ser Pro Gln Leu
1               5

<210> SEQ ID NO 134
<211> LENGTH: 9
<212> TYPE: PRT
<213> ORGANISM: Homo sapiens

<400> SEQUENCE: 134

Lys Ile Leu Ile Pro Gly Thr Leu Glu
1               5
```

```
<210> SEQ ID NO 135
<211> LENGTH: 9
<212> TYPE: PRT
<213> ORGANISM: Homo sapiens

<400> SEQUENCE: 135

Ser Ala Ala Pro Thr Ser Leu Gly Pro
1               5

<210> SEQ ID NO 136
<211> LENGTH: 9
<212> TYPE: PRT
<213> ORGANISM: Homo sapiens

<400> SEQUENCE: 136

His Gly Thr Asn Leu Thr Cys Gln Val
1               5

<210> SEQ ID NO 137
<211> LENGTH: 9
<212> TYPE: PRT
<213> ORGANISM: Homo sapiens

<400> SEQUENCE: 137

Ala Gly Val Thr Thr Glu Arg Thr Ile
1               5

<210> SEQ ID NO 138
<211> LENGTH: 9
<212> TYPE: PRT
<213> ORGANISM: Homo sapiens

<400> SEQUENCE: 138

Val Thr Tyr Val Pro Gln Asn Pro Thr
1               5

<210> SEQ ID NO 139
<211> LENGTH: 9
<212> TYPE: PRT
<213> ORGANISM: Homo sapiens

<400> SEQUENCE: 139

Ser Lys Leu His Gly Pro Thr Glu Thr
1               5

<210> SEQ ID NO 140
<211> LENGTH: 9
<212> TYPE: PRT
<213> ORGANISM: Homo sapiens

<400> SEQUENCE: 140

Asp Glu Glu Leu His Tyr Ala Ser Leu
1               5

<210> SEQ ID NO 141
<211> LENGTH: 9
<212> TYPE: PRT
<213> ORGANISM: Homo sapiens

<400> SEQUENCE: 141

Tyr Ala Ser Leu Asn Phe His Gly Met
1               5

<210> SEQ ID NO 142
```

```
<211> LENGTH: 9
<212> TYPE: PRT
<213> ORGANISM: Homo sapiens

<400> SEQUENCE: 142

Ser Leu Asn Phe His Gly Met Asn Pro
1               5

<210> SEQ ID NO 143
<211> LENGTH: 9
<212> TYPE: PRT
<213> ORGANISM: Homo sapiens

<400> SEQUENCE: 143

Val Pro Cys Thr Phe Phe His Pro Ile
1               5

<210> SEQ ID NO 144
<211> LENGTH: 9
<212> TYPE: PRT
<213> ORGANISM: Homo sapiens

<400> SEQUENCE: 144

Ser Gly Asp Ser Pro Val Ala Thr Asn
1               5

<210> SEQ ID NO 145
<211> LENGTH: 9
<212> TYPE: PRT
<213> ORGANISM: Homo sapiens

<400> SEQUENCE: 145

Asp Pro Ser Arg Asn Asn Cys Ser Leu
1               5

<210> SEQ ID NO 146
<211> LENGTH: 9
<212> TYPE: PRT
<213> ORGANISM: Homo sapiens

<400> SEQUENCE: 146

Ser Ile Val Asp Ala Arg Arg Arg Asp
1               5

<210> SEQ ID NO 147
<211> LENGTH: 9
<212> TYPE: PRT
<213> ORGANISM: Homo sapiens

<400> SEQUENCE: 147

Arg Met Glu Arg Gly Ser Thr Lys Tyr
1               5

<210> SEQ ID NO 148
<211> LENGTH: 9
<212> TYPE: PRT
<213> ORGANISM: Homo sapiens

<400> SEQUENCE: 148

Ser Pro Gln Leu Ser Val His Val Thr
1               5

<210> SEQ ID NO 149
<211> LENGTH: 9
<212> TYPE: PRT
```

<213> ORGANISM: Homo sapiens

<400> SEQUENCE: 149

Pro Lys Ile Leu Ile Pro Gly Thr Leu
1               5

<210> SEQ ID NO 150
<211> LENGTH: 9
<212> TYPE: PRT
<213> ORGANISM: Homo sapiens

<400> SEQUENCE: 150

Ser Val Leu Ile Ile Thr Pro Arg Pro
1               5

<210> SEQ ID NO 151
<211> LENGTH: 9
<212> TYPE: PRT
<213> ORGANISM: Homo sapiens

<400> SEQUENCE: 151

Ile Ile Thr Pro Arg Pro Gln Asp His
1               5

<210> SEQ ID NO 152
<211> LENGTH: 9
<212> TYPE: PRT
<213> ORGANISM: Homo sapiens

<400> SEQUENCE: 152

Arg Pro Gln Asp His Gly Thr Asn Leu
1               5

<210> SEQ ID NO 153
<211> LENGTH: 9
<212> TYPE: PRT
<213> ORGANISM: Homo sapiens

<400> SEQUENCE: 153

Gly Ala Gly Val Thr Thr Glu Arg Thr
1               5

<210> SEQ ID NO 154
<211> LENGTH: 9
<212> TYPE: PRT
<213> ORGANISM: Homo sapiens

<400> SEQUENCE: 154

Thr Glu Arg Thr Ile Gln Leu Asn Val
1               5

<210> SEQ ID NO 155
<211> LENGTH: 9
<212> TYPE: PRT
<213> ORGANISM: Homo sapiens

<400> SEQUENCE: 155

Arg Thr Ile Gln Leu Asn Val Thr Tyr
1               5

<210> SEQ ID NO 156
<211> LENGTH: 9
<212> TYPE: PRT
<213> ORGANISM: Homo sapiens

```
<400> SEQUENCE: 156

Gly Val Thr Ala Leu Leu Ala Leu Cys
1               5

<210> SEQ ID NO 157
<211> LENGTH: 9
<212> TYPE: PRT
<213> ORGANISM: Homo sapiens

<400> SEQUENCE: 157

Ile Val Lys Thr His Arg Arg Lys Ala
1               5

<210> SEQ ID NO 158
<211> LENGTH: 9
<212> TYPE: PRT
<213> ORGANISM: Homo sapiens

<400> SEQUENCE: 158

Ser Ala Ser Pro Lys His Gln Lys Lys
1               5

<210> SEQ ID NO 159
<211> LENGTH: 9
<212> TYPE: PRT
<213> ORGANISM: Homo sapiens

<400> SEQUENCE: 159

Gln Val Gln Glu Ser Val Thr Val Gln
1               5

<210> SEQ ID NO 160
<211> LENGTH: 9
<212> TYPE: PRT
<213> ORGANISM: Homo sapiens

<400> SEQUENCE: 160

Pro Tyr Tyr Asp Lys Asn Ser Pro Val
1               5

<210> SEQ ID NO 161
<211> LENGTH: 9
<212> TYPE: PRT
<213> ORGANISM: Homo sapiens

<400> SEQUENCE: 161

Gly Tyr Trp Phe Arg Glu Gly Ala Ile
1               5

<210> SEQ ID NO 162
<211> LENGTH: 9
<212> TYPE: PRT
<213> ORGANISM: Homo sapiens

<400> SEQUENCE: 162

Ile Ser Gly Asp Ser Pro Val Ala Thr
1               5

<210> SEQ ID NO 163
<211> LENGTH: 9
<212> TYPE: PRT
<213> ORGANISM: Homo sapiens

<400> SEQUENCE: 163
```

Leu Asp Gln Glu Val Gln Glu Glu Thr
1               5

<210> SEQ ID NO 164
<211> LENGTH: 9
<212> TYPE: PRT
<213> ORGANISM: Homo sapiens

<400> SEQUENCE: 164

Asn Cys Ser Leu Ser Ile Val Asp Ala
1               5

<210> SEQ ID NO 165
<211> LENGTH: 9
<212> TYPE: PRT
<213> ORGANISM: Homo sapiens

<400> SEQUENCE: 165

Arg Pro Lys Ile Leu Ile Pro Gly Thr
1               5

<210> SEQ ID NO 166
<211> LENGTH: 9
<212> TYPE: PRT
<213> ORGANISM: Homo sapiens

<400> SEQUENCE: 166

Ala Ala Pro Thr Ser Leu Gly Pro Arg
1               5

<210> SEQ ID NO 167
<211> LENGTH: 9
<212> TYPE: PRT
<213> ORGANISM: Homo sapiens

<400> SEQUENCE: 167

Ala Gly Ala Gly Val Thr Thr Glu Arg
1               5

<210> SEQ ID NO 168
<211> LENGTH: 9
<212> TYPE: PRT
<213> ORGANISM: Homo sapiens

<400> SEQUENCE: 168

Lys Gln Glu Thr Arg Ala Gly Val Val
1               5

<210> SEQ ID NO 169
<211> LENGTH: 9
<212> TYPE: PRT
<213> ORGANISM: Homo sapiens

<400> SEQUENCE: 169

Gly Ala Gly Val Thr Ala Leu Leu Ala
1               5

<210> SEQ ID NO 170
<211> LENGTH: 9
<212> TYPE: PRT
<213> ORGANISM: Homo sapiens

<400> SEQUENCE: 170

Thr Ala Leu Leu Ala Leu Cys Leu Cys
1               5

<210> SEQ ID NO 171
<211> LENGTH: 9
<212> TYPE: PRT
<213> ORGANISM: Homo sapiens

<400> SEQUENCE: 171

Leu Ala Leu Cys Leu Cys Leu Ile Phe
1               5

<210> SEQ ID NO 172
<211> LENGTH: 9
<212> TYPE: PRT
<213> ORGANISM: Homo sapiens

<400> SEQUENCE: 172

Arg Arg Lys Ala Ala Arg Thr Ala Val
1               5

<210> SEQ ID NO 173
<211> LENGTH: 9
<212> TYPE: PRT
<213> ORGANISM: Homo sapiens

<400> SEQUENCE: 173

Lys Ala Ala Arg Thr Ala Val Gly Arg
1               5

<210> SEQ ID NO 174
<211> LENGTH: 9
<212> TYPE: PRT
<213> ORGANISM: Homo sapiens

<400> SEQUENCE: 174

Ala Ala Arg Thr Ala Val Gly Arg Asn
1               5

<210> SEQ ID NO 175
<211> LENGTH: 9
<212> TYPE: PRT
<213> ORGANISM: Homo sapiens

<400> SEQUENCE: 175

Gly Arg Asn Asp Thr His Pro Thr Thr
1               5

<210> SEQ ID NO 176
<211> LENGTH: 9
<212> TYPE: PRT
<213> ORGANISM: Homo sapiens

<400> SEQUENCE: 176

Pro Lys His Gln Lys Lys Ser Lys Leu
1               5

<210> SEQ ID NO 177
<211> LENGTH: 9
<212> TYPE: PRT
<213> ORGANISM: Homo sapiens

<400> SEQUENCE: 177

Ser Ser Cys Ser Gly Ala Ala Pro Thr
1               5

```
-continued

<210> SEQ ID NO 178
<211> LENGTH: 9
<212> TYPE: PRT
<213> ORGANISM: Homo sapiens

<400> SEQUENCE: 178

Ser Thr Glu Tyr Ser Glu Val Arg Thr
1               5

<210> SEQ ID NO 179
<211> LENGTH: 9
<212> TYPE: PRT
<213> ORGANISM: Homo sapiens

<400> SEQUENCE: 179

Gly Ile Leu Gly Phe Val Phe Thr Leu
1               5
```

IMMUNOGENIC PEPTIDES

CLAIM FOR PRIORITY

This application claims priority to a provisional application Serial No. 60/509,051 filed May 3, 2002, the entire contents of which are hereby incorporated by reference.

FIELD OF INVENTION

The present invention relates to immunogenic peptides. More particularly the present invention relates to relatively short peptides associated with leukemia that elicit an immune response.

BACKGROUND OF THE INVENTION

Cancers, including leukemia, are the leading cause of death in humans. Roughly 32,000 new cases of, and 22,000 deaths caused by, leukemia occur in the U.S. each year. Most cases occur of leukemia occur in adults. The exact cause of leukemia is not known, but links between certain activities, such as exposure to carcinogens, and the incidence of certain types of carcinomas, lymphomas, e.g., leukemia and tumors, has been shown by a number of researchers. However, such exposures do not explain most cases of leukemia.

Acute myeloid leukemia (AML) is the most common type of acute leukemia in adults, with an annual incidence of 2.7 per 100,000 adults in the U.S. (Murashige et al., 2002). Progress in therapy and supportive care over the past three decades has led to a gradual improvement in the overall results, however, very little progress has been made regarding long-term survival. Newly diagnosed AML patients achieve complete remission (CR) following chemotherapy/radiation treatment, with a median duration of 15 months. A small percentage of patients with relapsed or refractory AML can be induced with chemotherapy/radiation to achieve a second CR and the duration of these responses are often only 4-8 months. Allogeneic stem cell transplantation (AlloSCT) has been conducted as a salvage therapy for those in whom conventional chemotherapy failed to control their disease, but most of them are relapsed.

Many types of chemotherapeutic agents have been shown to be effective against leukemia, but not all types of leukemia cells respond to these agents, and, unfortunately, many of these agents also destroy normal cells. Despite advances in the field of leukemia treatments, the leading therapies to date are radiation, chemotherapy and bone marrow transplants. However, these therapies generally harm normal cells as well as leukemic cells. Ideally cytotoxic agents that have specificity for leukemia cells while only minimally affecting normal healthy cells would be extremely desirable. Unfortunately, none have been found and instead agents which target especially rapidly dividing cells (both diseased and normal) have been used.

Thus there continues to be a strong need for methods of diagnosing and viable treatment regimens for leukemia.

SUMMARY OF THE INVENTION

One aspect of the present invention provides isolated or recombinant leukemic antigens comprising a fragment of CD33 antigen or a variant thereof that is capable of stimulating a cytotoxic T-lymphocyte reaction. The fragment or variant-thereof can be 8, 9, 10, 11 or 12 amino acids in length up to 50 or 80 amino acids in length. In some embodiments, the first position of the fragment is Y and the other positions are variable. In these and other embodiments, the second position of the fragment is L, M or I. In these and other embodiments, the fourth position is E or K. Additionally, the eighth position of the fragment can be K. When the fragment is at least nine residues in length the ninth position of the fragment can be V, T, L or I. In some aspects the isolated leukemic antigen is immunologically recognized by MHC restricted T-Lymphocytes that are HLA-A2.1 restricted. The identified leukemic antigen can have the amino acid sequence YLALCLCLI (SEQ ID NO: 1), AIISGDSPV (SEQ ID NO: 2), YIISGDSPV (SEQ ID NO: 3), YIISGISPV (SEQ ID NO: 6), YLISGDSPV (SEQ ID NO: 7), ALLALCLCL (SEQ ID NO: 8), TIQLNVTYV (SEQ ID NO: 9), YIGSGDSPV (SEQ ID NO: 10), YIIIGDSPV (SEQ ID NO: 11), YIILGDSPV (SEQ ID NO: 12), YIISGDLPV (SEQ ID NO: 13), YIISGDSWV (SEQ ID NO: 14), YIISGDSPL (SEQ ID NO: 15), ALISGDSPV (SEQ ID NO: 16) or LLALCLCLI (SEQ ID NO:42) with or without one or more, such as one, two, two, three, four, five or more conservative or nonconservative amino acid substitutions. The isolated leukemic antigen can also be combined with one or more co-immunostimulatory molecules.

The present invention also provides a method for stimulating an immune effector cell response achieved by contacting the isolated leukemic antigen with an immune effector cell which stimulates the immune effector cell to respond against the isolated leukemic antigen. In some methods the immune effector cell is a naïve T-lymphocyte or a memory T-lymphocyte. The method can be performed by contacting the isolated leukemic antigen with an antigen presenting cell, in vivo or in vitro, such that the antigen presenting cell contacts the isolated leukemic antigen with the immune effector cell. Suitable antigen presenting cells are dendritic cells or T2 cells.

The present invention also pertains to immune effector cells and antigen presenting cells produced by these methods. Nucleic acids encoding the present isolated leukemic antigens also form part of the present invention.

DETAILED DESCRIPTION OF PREFERRED EMBODIMENTS

Figure 1A:
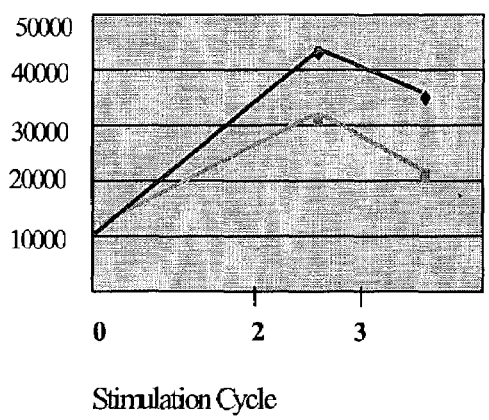
FIG. 1A shows IFN-γ production of cytotoxic T-lymphocytes (CTLs) stimulated by dendritic cells pulsed with the AIISGDSPV (SEQ ID NO: 2) peptide.

The present invention encompasses fragments of the CD33 antigen, variants, isoforms and other mammalian homologs thereof which are immunologically recognized by T lymphocytes of the immune system. CD33 antigen is generally expressed by myeloblasts, promyelocytes, myeolcytes, mast cells, throughout monocyte differentiation and is also highly expressed on a large percentage of leukemic cells. The present invention further encompasses the antigen cancer epitope(s) which are contained in the tumor antigen. The antigenic cancer epitope specifically causes a cellular mediated immune response by interaction with T cells of the immune system. This interaction between the antigenic cancer epitope and the T cells causes the T cells to respond against, and prevent, eliminate or reduce the cancer in a mammal, including humans. The peptides, nucleic acid molecules which code for such peptides, binding agents such as antibodies, antigen presenting cells (APCs) and/or immune system cells (e.g., T cells), antibodies against such peptides and nucleic acids, are useful, inter alia, in diagnostic and therapeutic contexts. Thus, the present invention provides a cancer vaccine.

CD33 is a member of the sialic acid-binding receptor family and is expressed on AML blast cells in greater than 90% of AML cases. This antigen is also expressed on normal myeloid precursor cells resulting in neutropenia and thrombocytopenia associated with anti-CD33 therapy. However, CD33 is not expressed on pluripotent stem cells, which allows hematologic recovery after the treatment period. The CD33 antigen is discussed in Simmons et al., J. Immunol. 141 (8), 2797-2800 (1988). Proteins similar or homologous to CD33 are discussed in Tchilian et al. Blood 83 (11), 3188-3198 (1994); Takei et al. Cytogenet. Cell Genet. 78 (3-4), 295-300 (1997). The sequence for the CD33 antigen) as reported in Simmons et al. and disclosed in the SwissProt annotated protein record P20138 is as follows:

```
  1 mplllllpll wagalamdpn fwlqvqesvt vqeglcvlvp ctffh-
    pipyy dknspvhgyw
 61 fregaiisgd spvatnkldq evqeetqgrf rllgdpsrnn cslsivdarr
    rdngsyfform
121 ergstkysyk spqlsvhvtd lthrpkilip gtlepghskn ltcs-
    vswace qgtppifswl
181 saaptslgpr tthssvliit prpqdhgtnl tcqvkfagag vttertiqln
    vtyvpqnptt
241 gifpgdgsgk qetragvvhg aiggagvtal lalciclifff ivkthrrkaa
    rtavgrndth
301 pttgsaspkh qkksklhgpt etsscsgaap tvemdeelhy aslnfh-
    gmnp skdtsteyse
361 vrtq
```

(SEQ ID NO: 4).

References discussing the CD33 protein, sequence, nucleic acids encoding and antibodies against include: Andrews et al. Blood 62:124-132 (1983); Andrews et al., J Exp Med 169: 1721-1731 (1989); Caron et al. Blood 83:1760-1768 (1994); Freeman et al., Blood 85:2005-2012 (1995); Griffin et al., Leuk Res 8:521-534 (1984); Peiper et al., Leukocyte Typing V. Oxford University Press p837-840 (1995); Peiper et al., Blood 72:314-321 (1988); Robertson et al., Blood 79:2229-2236 (1992); Sobol et al., N Engl J Med 316:1111-1117 (1987); and Thomas et al., J Immunol 153:4016-4028 (1994).

The domains or regions of CD33 are as follows:
(1) Signal peptide (aa 1-17);
(2) Extracellular region of 241 residues that includes and IgV domain (aa 18-121) and an IgC2 type domain (aa 156-219);
(3) Transmembrane spanning domain (aa 260-282); and
(4) Cytoplasmic tail (aa 283-364)

Proteins

The compounds of this invention generally comprise a polypeptide, sometimes in isolated form, that stimulates a Th1 or CTL (cytotoxic T-lymphocyte) immune response in peripheral blood mononuclear cells (PBMCs). In particular, polypeptides 8-12 amino acids in length comprising a stimulatory portion of the CD33 antigen are disclosed, such as a cancer rejection antigen. The peptides of the present invention can also be from 8 to 80 amino acids in length, such as 8, 9, 10, 11, 12, 13, 14, 15, 16, 17, 18, 19 or 20, 25, 30, 32, 35, 40, 45, 50, 55, 60, 65, 70, 75 or 80 residues, or consecutive amino acids of CD33, in length. Preferably, when the peptide is longer in length, then the sequence of the peptide will substantially correspond with the sequence of CD33, for example within about 1, 2, 5, 10 or 20 percent homology or identity. A cancer rejection antigen is an example of a unique fragment of a cancer specific polypeptide which retains the functional capability of HLA binding and interaction with cytotoxic T lymphocytes. Tumor rejection antigens presented by HLA molecules typically are 9 amino acids in length, although peptides of 8, 9, 10, 11 and 12 and more amino acids, up to about 80, can retain the capability to interact with HLA and cytotoxic T lymphocyte to an extent effective to provoke a cytotoxic T lymphocyte response (see, e.g., Van den Eynde & Brichard, Curr. Opin. Immunol. 7:674-681, 1995; Coulie et al., Stem Cells 13:393-403, 1995) and discussed in U.S. Pat. No. 6,271,019. Polypeptides encompass amino acid chains of any length, including full length proteins and portions thereof, wherein amino acid residues are linked by covalent peptide bonds. Although CD33 fragments are described herein for exemplary purposes, portions thereof, variants of the polypeptide (or portions thereof) and homologous proteins in other mammals can also be used. In one preferred embodiment, the polypeptides are substantially free of contaminating endogenous materials. In some embodiments, the peptides are derived from the signalling domain, extracellular domain, transmembrane spanning domain or cytoplasmic tail of CD33.

The term "isolated" means separated from constituents, cellular and otherwise, in which the polynucleotide, peptide, polypeptide, protein, antibody, or fragments thereof, are normally associated with in nature. As is apparent to those of skill in the art, a non-naturally occurring polynucleotide, peptide, polypeptide, protein, antibody, or fragments thereof, does not require "isolation" to distinguish it from its naturally occurring counterpart. In addition, a "concentrated," "separated" or "diluted" polynucleotide, peptide, polypeptide, protein, antibody, or fragment thereof, is distinguishable from its naturally occurring counterpart in that the concentration or number of molecules per volume is greater than "concentrated" or less than "separated" than that of its naturally occurring counterpart. A polynucleotide, peptide, polypeptide, protein, antibody, or fragments thereof, which differs from the naturally occurring counterpart in its primary sequence or for example, by its glycosylation pattern, need not be present in its isolated form since it is distinguishable from its naturally occurring counterpart by its primary sequence, or alternatively, by another characteristic such as glycosylation pattern. Although not explicitly stated for each of the inventions disclosed herein, it is to be understood that all of the above embodiments for each of the compositions disclosed below and under the appropriate conditions, are provided by this invention. Thus, a non-naturally occurring polynucleotide is provided as a separate embodiment from the isolated naturally occurring polynucleotide. A protein produced in a bacterial cell is provided as a separate embodiment from the naturally occurring protein isolated from a eukaryotic cell in which it is produced in nature.

Several peptide fragments of the CD33 antigen and have been discovered which have the ability to stimulate a T-lymphocyte mediated cellular immune response. Peptides of the present invention can include these amino acid sequences in any configuration or location in the peptide. In some embodiments, specific positions in the peptides, referred to hereinafter as anchor positions, have defined amino acids. Examples of such anchor positions can include Y as the first amino acid of the peptide sequence with the other positions being variable. Other anchor positions include the second position of the fragment which can be L, M or I, the fourth position which can be E, K or S. Additionally, the eighth position of the fragment can be an anchor position and can be K. When the fragment is at least nine residues in length, the first, second and ninth positions of the fragment can be anchor positions in which the first position can be Y, the second can be L or M, and/or the ninth position can be V or L. The peptides disclosed herein can have one or more of any of these anchor positions with the recited amino acids. Accordingly, the present peptides cover all possible combinations and subcombinations of these anchor sequences. Preferably, fragments of the CD33 protein having one or more of these anchor positions, such as those shown below, are used in the present methods and compositions. Such peptides can have these following sequences, where a 1 indicates the presence of an anchor amino acid at the first position as recited above, i.e. a Y, a 2 indicates the presence of an anchor amino acid at the second position as recited above, i.e. a L, M or I, a 4 indicates the presence of an anchor amino acid at the fourth position as recited above, i.e. a E, K or S, an 8 indicates the presence of an anchor amino acid at the eighth position as recited above, i.e. a K, and a 9 indicates the presence of an anchor amino acid at the ninth position as recited above, i.e. a V, T, L or I, X indicates the presence of any amino acid residue and Xa indicates an optional amino residue.

| | |
|---|---|
| 1XXXXXXX | (SEQ ID NO: 17) |
| X2XXXXXX | (SEQ ID NO: 18) |
| XXX4XXXX | (SEQ ID NO: 19) |
| XXXXXXX8 | (SEQ ID NO: 20) |
| XXXXXXXX9 | (SEQ ID NO: 21) |
| 12XXXXXX | (SEQ ID NO: 22) |
| 1XX4XXXX | (SEQ ID NO: 23) |
| 1XXXXXX8a | (SEQ ID NO: 24) |
| 1XXXXXXX9 | (SEQ ID NO: 25) |
| 12X4XXXX | (SEQ ID NO: 26) |
| 12XXXXX8 | (SEQ ID NO: 27) |
| 12XXXXXX9 | (SEQ ID NO: 28) |
| 12X4XXX8 | (SEQ ID NO: 29) |
| 12X4XXXX9 | (SEQ ID NO: 30) |
| 12X4XXX89 | (SEQ ID NO: 31) |
| X2X4XXXX | (SEQ ID NO: 32) |
| X2XXXXX8 | (SEQ ID NO: 33) |
| X2XXXXXX9 | (SEQ ID NO: 34) |
| X2X4XXX8 | (SEQ ID NO: 35) |
| X2X4XXXX9 | (SEQ ID NO: 36) |
| X2X4XXX89 | (SEQ ID NO: 37) |
| XXX4XXX8 | (SEQ ID NO: 38) |
| XXX4XXXX9 | (SEQ ID NO: 39) |
| XXX4XXX89 | (SEQ ID NO: 40) |
| XXXXXXX89 | (SEQ ID NO: 41) |

The present peptides should be capable of stimulating a cytotoxic T-lymphocyte reaction. These anchor positions also provide a guide to the skilled artisan for modifying fragments of CD33 to increase the immunogenicity of the peptide. As will be understood by one skilled in the art, generally, the first, second, and ninth amino acids are considered to be important for binding to MHC molecules and the third, fourth, fifth, sixth and seventh amino acids are considered as important for recognition by T-cell receptors. However, the interactions with neighboring amino acids are also important to MHC bindings and recognition by T-cell receptors. As will be understood by the skilled artisan, the anchor positions denoted above are only numbered with respect to one another but can be placed in any relative orientation or appropriate place within a larger immunogenic peptide. For example, SEQ ID NO:30 can be part of 25 amino acid peptide and anchor position 1 can start at position 5, 7, 8, etc. within the peptide. Preferably, peptides having these anchor positions have sequences at the non-anchor positions that correspond to the CD33 sequence. Thus target fragments of CD33 and mammalian homologs thereof can be identified by aligning the desired anchor position or positions with the CD33 or homologous protein sequence and selecting the desired portion of the CD33 sequence or homolog.

Specific examples of peptides include peptides as discussed herein include the amino acid sequence YLALCLCLI (SEQ ID NO: 1), AIISGDSPV (SEQ ID NO: 2), YIISGDSPV (SEQ ID NO: 3), YIISGISPV (SEQ ID NO: 6), YLISGDSPV (SEQ ID NO: 7), ALLALCLCL (SEQ ID NO: 8), TIQLNVTYV (SEQ ID NO: 9), YIGSGDSPV (SEQ ID NO: 10), YIIIGDSPV (SEQ ID NO: 11), YIILGDSPV (SEQ ID NO: 12), YIISGDLPV (SEQ ID NO: 13), YIISGDSWV (SEQ ID NO: 14), YIISGDSPL (SEQ ID NO: 15), ALISGDSPV (SEQ ID NO: 16) or LLALCLCLI (SEQ ID NO:42) with or without one or more conservative or nonconservative amino acid substitutions. Combinations of these peptides are also suitable for use in the present compounds and methods described herein.

Biologically functionally equivalent variants of the present CD33 polypeptide fragments, i.e., variants of polypeptides which retain the function of the natural polypeptide fragment, can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. The skilled artisan will also realize that conservative amino acid substitutions can be made in the present polypeptides to provide such functionally active homologs of the forgoing polypeptides, i.e., the homologs retain the functional capabilities of the polypeptides. As used herein, a "conservative amino acid substitution" refers to an amino acid substitution which does not alter the relative charge or size characteristics of the protein in which the amino acid substitution is made. Conservative substitutions of amino acids generally are understood to include substitutions made amongst amino acids within the following groups: (a) M, I, L, V; (b) F, Y, W; (c) K, R, H; (d) A, G; (e) S, T; (f) Q, N; and (g) E, D. The present invention also encompasses polypeptides with one or more nonconservative amino acid substitutions that retain similar functionality compared to the non-modified peptide. Generally a "nonconservative amino acid substitution" is understood to be an amino acid substituted by an alternative amino acid of differing charge density, hydrophilicity/hydrophobicity, size, and/or configuration (e.g., Val for Phe). The means of making such modifications are well known in the art and can be readily accomplished by means of commercially available kits and vectors (e.g., New England Biolabs, Inc., Beverly, Mass.; Clontech, Palo Alto, Calif.). Moreover, the means of assessing such substitutions (e.g., in terms of effect on ability to bind and enter cells) are known in the art and described for example in U.S. Pat. No. 6,329,190.

The polypeptides of the present invention also include variants of the CD33 fragments that retain the ability to stimulate a Th1 or CTL immune response in PBMCs. Such variants include various structural forms of the primary protein, including related and homologous proteins which can be found in non-human species. Due to the presence of ionizable amino and carboxyl groups, for example, a polypeptide fragment can be in the form of an acidic or basic salt, or can be in neutral form. Individual amino acid residues can also be modified by oxidation or reduction.

Variants within the scope of this invention also include polypeptides in which the primary amino acid structure of the polypeptide fragment is modified by forming covalent or aggregative conjugates with other polypeptides or chemical moieties such as glycosyl groups, lipids, phosphate, acetyl groups and the like. Covalent derivatives can be prepared, for example, by linking particular functional groups to amino acid side chains or at the N- or C-termini. Alternatively, for derivatives in which a polypeptide is joined to a CD33 fragment, a fusion protein can be prepared using recombinant DNA techniques, as described below. As will be understood by the skilled artisan, fusion peptides containing the 8-12 amino acid CD33 fragment of the present invention are not limited to 8-12 amino acids in total size, but instead that the immunogenic fragment of the CD33 antigen is 8-12 residues in size. In one such embodiment, the CD33 polypeptide polypeptide can be conjugated to a signal (or leader) polypeptide sequence at the N-terminal region of the protein which co-translationally or post-translationally directs transfer of the protein from its site of synthesis to its site of function inside or outside of the cell membrane or wall (e.g., the yeast α-factor leader).

The present peptides can also be derived from non-human mammalian peptides that are homologous to CD33. Examples of murine CD33 homologs are disclosed in Tchilian et al. Blood Jun. 1, 1994;83(11):3188-98.

Also provided by this application are the polypeptides and proteins described herein conjugated to a detectable agent for use in the diagnostic methods. For example, detectably labeled proteins and polypeptides can be bound to a column and used for the detection and purification of antibodies. They also are useful as immunogens for the production of antibodies as described below. The proteins and fragments of this invention are useful in an in vitro assay system to screen for agents or drugs, which modulate cellular processes.

Such detectable agents include protein fusions with other proteins and which can facilitate purification or identification of the polypeptides (e.g., poly-His). For example, the peptide described by Hopp et al., Bio/Technology 6:1204 (1988) is a highly antigenic peptide that can be used to facilitate identification. Such a peptide provides an epitope reversibly bound by a specific monoclonal antibody, enabling rapid assay and facile purification of expressed recombinant protein. The sequence of Hopp et al. is also specifically cleaved by bovine mucosal enterokinase, allowing removal of the peptide from the purified protein. Fusion proteins capped with such peptides can also be resistant to intracellular degradation in *E. coli*.

Protein fusions encompassed by this invention further include, for example, the polypeptides linked to an immunoglobulin Fc region. If the fusion proteins are made with both heavy and light chains of an antibody, it is possible to form a protein oligomer with as many as four CD33 protein fragment regions. Also within the scope of the present invention are polypeptides linked to a leucine zipper domain. Leucine zipper domains are described, for example, in published PCT Application WO 94/10308. The present polypeptides comprising leucine zippers may, for example, be oligomeric, dimeric or trimeric. All of the above protein fusions can be prepared by chemical linkage or as fusion proteins, as described in U.S. Pat. No. 6,013,268. Preferred protein fusions include polypeptides that comprise sequences useful for stimulating immunity to infectious pathogens (e.g., antigens). Such sequences can be derived, for example, from viruses, tumor cells, parasites or bacteria.

The proteins and polypeptides of this invention can be obtained by chemical synthesis using a commercially available automated peptide synthesizer such as those manufactured by Perkin Elmer/Applied Biosystems, Inc., Model 430A or 431A, Foster City, Calif., USA. The synthesized protein or polypeptide can be precipitated and further purified, for example by high performance liquid chromatography (HPLC). Accordingly, this invention also provides a process for chemically synthesizing the proteins of this invention by providing the sequence of the protein and reagents, such as amino acids and enzymes and linking together the amino acids in the proper orientation and linear sequence.

Alternatively, the proteins and polypeptides can be obtained by well-known recombinant methods as described above using the host cell and vector systems described above.

Nonpeptide analogs of peptides, e.g., those which provide a stabilized structure or lessened biodegradation, are also contemplated. Peptide mimetic analogs can be prepared based on a selected binding peptide by replacement of one or more residues by nonpeptide moieties. Preferably, the nonpeptide moieties permit the peptide to retain its natural conformation, or stabilize a preferred, e.g., bioactive, confirmation. Such peptides can be tested in molecular or cell-based binding assays to assess the effect of the substitution(s) on conformation and/or activity. One example of methods for preparation of nonpeptide mimetic analogs from peptides is described in Nachman et al., Regul. Pept. 57:359-370 (1995) and disclosed in U.S. Pat. No. 6,291,430.

The proteins of this invention also can be combined with various liquid phase carriers, such as sterile or aqueous solutions, pharmaceutically acceptable carriers, suspensions and emulsions. Examples of non-aqueous solvents include propyl ethylene glycol, polyethylene glycol and vegetable oils. When used to prepare antibodies, the carriers also can include an adjuvant that is useful to non-specifically augment a specific immune response. A skilled artisan can easily determine whether an adjuvant is required and select one. However, for the purpose of illustration only, suitable adjuvants include, but are not limited to Freund's Complete and Incomplete, mineral salts, polynucleotides, GM-CSF and Keyhole Limpet Hemocyanin (KLH). Adjuvant can be used as is known in the art, for example as a carrier or vehicle.

Nucleic Acids

Polynucleotides of the subject invention generally comprise a DNA or RNA sequence that encodes all or a portion of the above CD33 polypeptide fragments, or that is complementary to such a sequence. Nucleic acids encoding proteins related or homologous to CD33 are disclosed in Tchilian et al. Blood 83 (11), 3188-3198 (1994); and Takei et al. Cytogenet. Cell Genet. 78 (3-4), 295-300 (1997). Preferably, the CD33 polypeptide fragment is a leukemia associated nucleic acid or polypeptide is a nucleic acid or polypeptide expressed preferentially in leukemias and solid forms of leukemia cell malignancies, such as lymphomas. Various methods for determining the expression of a nucleic acid and/or a polypeptide in normal and leukemia cells are known to those of skill in the art.

The reported nucleic acid sequence encoding the CD33 protein described above, as reported in Simmons et al., J. Immunol. 141 (8), 2797-2800 (1988), is (SEQ ID NO: 5):

1 gcttcctcag acatgccgct gctgctactg ctgcccctgc tgtgggcagg ggccctggct 61 atggatccaa atttctggct gcaagtgcag gagtcagtga cggtacagga gggtttgtgc 121 gtcctcgtgc cctgcacttt cttccatccc atacccctact acgacaagaa ctcccccagtt 181 catggttact ggttccggga aggagccatt atatccgggg actctccagt ggccacaaac 241 aagctagatc aagaagtaca ggaggagact cagggcagat tccgcctcct tggggatccc 301 agtaggaaca actgctccct gagcatcgta gacgccagga ggagggataa tggttcatac 361 ttctttcgga tggagagagg aagtaccaaa tacagttaca aatctcccca gctctctgtg 421 catgtgacag acttgaccca caggcccaaa atcctcatcc ctgcactct agaacccggc 481 cactccaaaa accttacctg ctctgtgtcc tgggcctgtg agcaggaac accccgatc 541 ttctcctggt tgtcagctgc ccccacctcc ctgggcccca ggactactca ctcctcggtg 601 ctcataatca ccccacggcc ccaggaccac ggcaccaacc tgacctgtca ggtgaagttc 661 gctggagctg gtgtgactac ggagagaacc atccagctca acgtcaccta tgttccacag 721 aacccaacaa ctggtatctt tccaggagat ggctcaggga aacaagagac cagagcagga 781 ctggttcatg gggccattgg aggagctggt gttacagccc tgctcgctct ttgtctctgc 841 ctcatcttct tcatagtgaa gacccacagg aggaaagcag ccaggacagc agtgggcagc 901 aatgacaccc accctaccac agggtcagcc tccccgaaac accagaagaa ctccaagtta 961 catggcccca ctgaaacctc aagctgttca ggtgccgccc ctactgtgga gatggatgag 1021 gagctgcatt atgcttccct caactttcat gggatgaatc cttccaagga cacctccacc 1081 gaatactcag aggtcaggac ccagtgagga accctcaaga gcatcaggct cagctagaag 1141 atccacatcc tctacaggtc ggggaccaaa ggctgattct tggagattta actccccaca 1201 ggcaatgggt ttatagacat tatgtgagtt tcctgctata ttaacatcat cttgagactt 1261 tgcaagcaga gagtcgtgga atcaaatctg tgctctttca tttgctaagt gtatgatgtc 1321 acacaagctc cttaaccttc catgtctcca ttttcttctc tgtgaagtag gtataagaag 1381 tcctatctca tagggatgct gtgagcatta aataaaggta cacatgaaa acaccag The nucleic acids contemplate the degeneracy of the genetic code in which nucleic acids can be coded by alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets can be employed to direct the protein synthesis apparatus, in vitro or in vivo, to incorporate a serine residue. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues can be encoded similarly by multiple nucleotide sequences. Thus, the invention embraces degenerate nucleic acids that differ from the biologically isolated nucleic acids in codon sequence due to the degeneracy of the genetic code.

Further contemplated are antisense oligonucleotides that selectively bind to a leukemia associated gene nucleic acid molecule. Additionally, nucleic acid mimetics, such as peptide nucleic acids are contemplated in the definition of nucleic acids.

The polynucleotides and peptides can be used for comparison to known and unknowns sequences using a computer-based method to match a sample sequence with known sequences. Thus, this invention also provides the polynucleotides or peptides in a computer database or in computer readable form, including applications utilizing the internet.

A linear search through such a database can be used. Alternatively, the polynucleotide sequence can be converted into a unique numeric representation. The comparison aspects can be implemented in hardware or software, or a combination of both. Preferably, these aspects of the invention are implemented in computer programs executing on a programmable computer comprising a processor, a data storage system (including volatile and non-volatile memory and/or storage elements), at least one input device, and at least one output device. Data input through one or more input devices for temporary or permanent storage in the data storage system includes sequences, and can include previously generated polynucleotides and codes for known and/or unknown sequences. Program code is applied to the input data to perform the functions described above and generate output information. The output information is applied to one or more output devices, in known fashion.

Each such computer program is preferably stored on a storage media or device (e.g., ROM or magnetic diskette) readable by a general or special purpose programmable computer, for configuring and operating the computer when the storage media or device is read by the computer to perform the procedures described herein. The inventive system can also be considered to be implemented as a computer-readable storage medium, configured with a computer program, where the storage medium so configured causes a computer to operate in a specific and predefined manner to perform the functions described herein.

The polynucleotides of the present invention also can serve as primers for the detection of genes or gene transcripts that are expressed in APC, for example, to confirm transduction of the polynucleotides into host cells. In this context, amplification means any method employing a primer-dependent polymerase capable of replicating a target sequence with reasonable fidelity. Amplification can be carried out by natural or recombinant DNA-polymerases such as T7 DNA polymerase, Klenow fragment of *E. coli* DNA polymerase, and reverse transcriptase.

The invention further provides the isolated polynucleotide operatively linked to a promoter of RNA transcription, as well as other regulatory sequences for replication and/or transient or stable expression of the DNA or RNA. As used herein, the term "operatively linked" means positioned in such a manner that the promoter will direct transcription of RNA off the DNA molecule. Examples of such promoters are SP6, T4 and T7. In certain embodiments, cell-specific promoters are used for cell-specific expression of the inserted polynucleotide. Vectors which contain a promoter or a promoter/enhancer, with termination codons and selectable marker sequences, as well as a cloning site into which an inserted piece of DNA can be operatively linked to that promoter are well known in the art and commercially available. For general methodology and cloning strategies, see GENE EXPRESSION TECHNOLOGY (Goeddel ed., Academic Press, Inc. (1991)) and references cited therein and VECTORS: ESSENTIAL DATA SERIES (Gacesa and Ramji, eds., John Wiley & Sons, N.Y. (1994)), which contains maps, functional properties, commercial suppliers and a reference to GenEMBL accession numbers for various suitable vectors. Preferable, these vectors are capable of transcribing RNA in vitro or in vivo.

Expression vectors containing these nucleic acids are useful to obtain host vector systems to produce proteins and polypeptides. It is implied that these expression vectors must be replicable in the host organisms either as episomes or as an integral part of the chromosomal DNA. Suitable expression vectors include plasmids, viral vectors, including adenoviruses, adeno-associated viruses, retroviruses, cosmids, etc. Adenoviral vectors are particularly useful for introducing genes into tissues in vivo because of their high levels of expression and efficient transformation of cells both in vitro and in vivo. When a nucleic acid is inserted into a suitable host cell, e.g., a prokaryotic or a eukaryotic cell and the host cell replicates, the protein can be recombinantly produced. Suitable host cells will depend on the vector and can include mammalian cells, animal cells, human cells, simian cells, insect cells, yeast cells, and bacterial cells constructed using well known methods. See Sambrook, et al. (1989) Supra. In addition to the use of viral vector for insertion of exogenous nucleic acid into cells, the nucleic acid can be inserted into the host cell by methods well known in the art such as transformation for bacterial cells; transfection using calcium phosphate precipitation for mammalian cells; or DEAE-dextran; electroporation; or microinjection. See Sambrook et al. (1989) Supra for this methodology. Thus, this invention also provides a host cell, e.g. a mammalian cell, an animal cell (rat or mouse), a human cell, or a prokaryotic cell such as a bacterial cell, containing a polynucleotide encoding a protein or polypeptide or antibody.

When the vectors are used for gene therapy in vivo or ex vivo, a pharmaceutically acceptable vector is preferred, such as a replication-incompetent retroviral or adenoviral vector. Pharmaceutically acceptable vectors containing the nucleic acids of this invention can be further modified for transient or stable expression of the inserted polynucleotide. As used herein, the term "pharmaceutically acceptable vector" includes, but is not limited to, a vector or delivery vehicle having the ability to selectively target and introduce the nucleic acid into dividing cells. An example of such a vector is a "replication-incompetent" vector defined by its inability to produce viral proteins, precluding spread of the vector in the infected host cell. An example of a replication-incompetent retroviral vector is LNL6 (Miller, A. D. et al. (1989) BioTechniques 7:980-990). The methodology of using replication-incompetent retroviruses for retroviral-mediated gene transfer of gene markers is well established (Correll, et al. (1989) PNAS USA 86:8912; Bordignon (1989) PNAS USA 86:8912-52; Culver, K. (1991) PNAS USA 88:3155; and Rill, D. R. (1991) Blood 79(10):2694-700.

These host cells containing the polynucleotides of this invention are useful for the recombinant replication of the polynucleotides and for the recombinant production of peptides. Alternatively, the cells can be used to induce an immune response in a subject in the methods described herein. When the host cells are antigen presenting cells, they can be used to expand a population of immune effector cells such as tumor infiltrating lymphocytes which in turn are useful in adoptive immunotherapies.

Protein Binding Agents (Antibodies)

The invention also involves agents which bind to leukemia associated polypeptides disclosed herein. Such binding partners can be used in screening assays to detect the presence or absence of the present polypeptides and in purification protocols to isolate these polypeptides. Likewise, such binding partners can be used to selectively target drugs, toxins or other molecules to leukemia cells which present the associated polypeptides. In this manner, cells present in solid or non-solid tumors which express the CD33 fragments can be treated with cytotoxic compounds.

The invention, therefore, involves antibodies or fragments of antibodies having the ability to selectively bind to the disclosed polypeptides. Antibodies against the CD33 antigen are discussed in Co et al., Chimeric and Humanized Antibodies with Specificity for the CD33 Antigen, J. Immunol. 148, 1149-1154 (1992). Antibodies include polyclonal and monoclonal antibodies, prepared according to conventional methodology. The antibodies can include, but are not limited to mouse, rat, and rabbit or human antibodies. The antibodies are useful to identify and purify polypeptides and APCs expressing the polypeptides.

The antibodies of the present invention are prepared by any of a variety of methods, including administering protein, fragments of protein, cells expressing the protein or fragments thereof and the like to an animal to induce polyclonal antibodies. Laboratory methods for producing polyclonal antibodies and monoclonal antibodies, as well as deducing their corresponding nucleic acid sequences, are known in the art, see Harlow and Lane (1988) Supra and Sambrook, et al. (1989) Supra. The monoclonal antibodies of this invention can be biologically produced by introducing protein or a fragment thereof into an animal, e.g., a mouse or a rabbit. The antibody producing cells in the animal are isolated and fused with myeloma cells or heteromyeloma cells to produce hybrid cells or hybridomas. Accordingly, the hybridoma cells producing the monoclonal antibodies of this invention also are provided.

The antibodies of this invention can be linked to a detectable agent or label. There are many different labels and methods of labeling known to those of ordinary skill in the art. The coupling of antibodies to low molecular weight haptens can increase the sensitivity of the assay. The haptens can then be specifically detected by means of a second reaction. For example, it is common to use haptens such as biotin, which reacts avidin, or dinitropherryl, pyridoxal, and fluorescein, which can react with specific anti-hapten antibodies. See Harlow and Lane (1988) Supra. Antibodies also can be coupled to specific labeling agents for imaging or to antitumor agents, including, but not limited to, methotrexate, radioiodinated compounds, toxins such as ricin, other cytostatic or cytolytic drugs, and so forth. Antibodies prepared according to the invention also preferably are specific for the CD33 complexes described herein. Variations of antibodies encompasses by the present invention can be found in U.S. Pat. No. 6,303,756.

The monoclonal antibodies of the invention also can be bound to many different carriers. Thus, this invention also provides compositions containing the antibodies and another substance, active or inert. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

Thus, using the protein or fragment thereof, and well known methods, one of skill in the art can produce and screen the hybridoma cells and antibodies of this invention for antibodies having the ability to bind the proteins or polypeptides. As detailed herein, such antibodies can also be used to identify tissues expressing protein or to purify protein.

If a monoclonal antibody being tested binds with the protein or polypeptide, then the antibody being tested and the antibodies provided by the hybridomas of this invention are equivalent. It also is possible to determine without undue experimentation, whether an antibody has the same specificity as the monoclonal antibody of this invention by determining whether the antibody being tested prevents a monoclonal antibody of this invention from binding the protein or polypeptide with which the monoclonal antibody is normally reactive. If the antibody being tested competes with the monoclonal antibody of the invention as shown by a decrease in binding by the monoclonal antibody of this invention, then it is likely that the two antibodies bind to the same or a closely related epitope. Alternatively, one can pre-incubate the monoclonal antibody of this invention with a protein with which it is normally reactive, and determine if the monoclonal antibody being tested is inhibited in its ability to bind the antigen. If the monoclonal antibody being tested is inhibited then, in all likelihood, it has the same, or a closely related, epitopic specificity as the monoclonal antibody of this invention.

The term "antibody" also is intended to include antibodies of all isotypes. Particular isotypes of a monoclonal antibody can be prepared either directly by selecting from the initial fusion, or prepared secondarily, from a parental hybridoma secreting a monoclonal antibody of different isotype by using the sib selection technique to isolate class switch variants using the procedure described in Steplewski, et al. (1985) Proc. Natl. Acad. Sci. 82:8653 or Spira, et al. (1984) J. Immunol. Methods 74:307.

This invention also provides biological active fragments of the polyclonal and monoclonal antibodies described above. These "antibody fragments" retain some ability to selectively bind with its antigen or immunogen. Such antibody fragments can include, but are not limited to: (1) Fab, (2) Fab', (3) F(ab')$_2$, (4) Fv, and (5) SCA. A specific example of "a biologically active antibody fragment" is a CDR region of the antibody. Methods of making these fragments are known in the art, see for example, Harlow and Lane (1988) Supra.

The isolation of other hybridomas secreting monoclonal antibodies with the specificity of the monoclonal antibodies of the invention can also be accomplished by one of ordinary skill in the art by producing anti-idiotypic antibodies (Herlyn, et al. (1986) Science 232: 100). An anti-idiotypic antibody is an antibody which recognizes unique determinants present on the monoclonal antibody produced by the hybridoma of interest.

Idiotypic identity between monoclonal antibodies of two hybridomas demonstrates that the two monoclonal antibodies are the same with respect to their recognition of the same epitopic determinant. Thus, by using antibodies to the epitopic determinants on a monoclonal antibody it is possible to identify other hybridomas expressing monoclonal antibodies of the same epitopic specificity.

Compositions containing the antibodies, fragments thereof or cell lines which produce the antibodies, are encompassed by this invention. When these compositions are to be used pharmaceutically, they can be combined with a pharmaceutically acceptable carrier.

Pulsing Antigen Presenting Cells

The polypeptides of this invention also can be pulsed into antigen presenting cells using the methods described herein either in vivo or in vitro. Various methods of pulsing the antigen presenting cells are disclosed in U.S. Pat. No. 6,306, 640, Lodge et al. (2000), Cancer Res. 60:829, Lau et al. (2001), J Immun. 24(1):66, Gajewski et al. (2001), Clin. Cancer Res. 7:895s, Morse et al. (1999), Clin. Cancer Res. 5:1331 and Schmidt et al. (1997) Proc. Natl. Acad. Sci. 94:3262. Antigen-presenting cells, include, but are not limited to dendritic cells (DCs), monocytes/macrophages, B lymphocytes or other cell type(s) expressing the necessary MHC/co-stimulatory molecules. The methods described below focus primarily on DCs which are the most potent, preferred APCs. These host cells containing the polypeptides or proteins are further provided.

The terms "antigen-presenting cells" or "APCs" includes both intact, whole cells as well as other molecules which are capable of inducing the presentation of one or more antigens, preferably in association with MHC molecules. Examples of suitable APCs are discussed in detail below and include, but are not limited to, whole cells such as macrophages, dendritic cells, B cells, purified MHC class I molecules complexed to beta 2-microglobulin; and foster antigen presenting cells.

Dendritic cells are the most effective type of antigen presenting cells (APC) in the human body expressing significant levels of co-stimulatory (CD86, CD80) and MHC class I and class II molecules on their cell surface. Many different factors and cytokine combinations have been demonstrated to produce mature dendritic cells (mDCs) in vitro. It has been shown that DCs provide all the signals required for T cell activation and proliferation. These signals can be categorized into two types. The first type, which gives specificity to the immune response, is mediated through interaction between the T-cell receptor/CD3 ("TCR/CD3") complex and an antigenic peptide presented by a major histocompatibility complex ("MHC") class I or II protein on the surface of APCs. This interaction is necessary, but not sufficient, for T cell activation to occur. In fact, without the second type of signals, the first type of signals can result in T cell anergy. The second type of signals, called costimulatory signals, is neither antigen-specific nor MHC-restricted, and can lead to a full proliferation response of T cells and induction of T cell effector functions in the presence of the first type of signals. As used herein, "dendritic cell" is to include, but not be limited to a pulsed dendritic cell, a foster cell or a dendritic cell hybrid.

The term "immune effector cells" refers to cells capable of binding an antigen or which mediate an immune response. These cells include, but are not limited to, T cells, B cells, monocytes, macrophages, NK cells and cytotoxic T lymphocytes (CTLs), for example CTL lines, CTL clones, and CTLs from tumor, inflammatory, or other infiltrates. A "naive" cell is a cell that has never been exposed to an antigen. As demonstrated in the Examples, the present methods, peptides and effector cells can induce or provide not only significant levels of cytotoxicity, but levels of cytotoxicity from about 20 percent up to about 64 percent, or more specifically 21, 29, 31, 33, 34, 35, 36, 37 or 39 percent to 42, 43, 55, 56, 63 or 64 percent in various cell types.

Isolated host cells which present the polypeptides of this invention in the context of MHC molecules are further useful to expand and isolate a population of educated, antigen-specific immune effector cells. The immune effector cells, e.g., cytotoxic T lymphocytes, are preferably produced by culturing naive immune effector cells with antigen-presenting cells that present the polypeptides in the context of MHC molecules on the surface of the APCs. The population can be purified using methods known in the art, e.g., FACS analysis or ficoll gradient. The methods to generate and culture the immune effector cells as well as the populations produced thereby also are the inventor's contribution and invention. Pharmaceutical compositions comprising the cells and pharmaceutically acceptable carriers are useful in adoptive immunotherapy. Prior to administration in vivo, the immune effector cells can be screened in vitro for their ability to lyse melanoma tumor cells.

In one embodiment, the immune effector cells and/or the APCs are genetically modified. Using standard gene transfer, genes coding for co-stimulatory molecules and/or stimulatory cytokines can be inserted prior to, concurrent to or subsequent to expansion of the immune effector cells.

Immune Effector Cells

The present invention also encompasses these immune effector cells that have been exposed to polypeptides of the present invention, preferably in an isolated form. Alternative to the above, the immune effector cells can be exposed to the polypeptides, preferably in the presence of one or more stimulatory molecules, without the help of antigen presenting cells.

Immune Response Induction

This invention also provides methods of inducing an immune response in a subject, comprising administering to the subject an effective amount of the polypeptides described above under the conditions that induce an immune response to the polypeptide. The polypeptides can be administered in formulations or as polynucleotides encoding the polypeptides. The polynucleotides can be administered in a gene delivery vehicle or by inserting into a host cell which in turn recombinantly transcribes, translates and processes the encoded polypeptide. Isolated host cells containing the polynucleotides of this invention in a pharmaceutically acceptable carrier can therefore combined with appropriate and effective amount of an adjuvant, cytokine or co-stimulatory molecule for an effective vaccine regimen. The vaccination can either be prophylactic or for treatment of established cancer. In one embodiment, the host cell is an APC such as a dendritic cell. The host cell can be further modified by inserting a polynucleotide coding for an effective amount of either or both of a cytokine a co-stimulatory molecule.

The methods of this invention can be further modified by co-administering an effective amount of a cytokine or co-stimulatory molecule. As used herein, the term "cytokine" refers to any one of the numerous factors that exert a variety of effects on cells, for example, inducing growth or proliferation. Non-limiting examples of cytokines which can be used alone or in combination in the practice of the present invention include, interleukin-2 (IL-2), stem cell factor (SCF), interleukin 3 (IL-3), interleukin 6 (IL-6), interleukin 12 (IL-12), G-CSF, granulocyte macrophage-colony stimulating factor (GM-CSF), interleukin-1 alpha (IL-1.sub.I), interleukin-11 (IL-11), MIP-1ı, leukemia inhibitory factor (LIF), c-kit ligand, thrombopoietin (TPO) and flt3 ligand. The present invention also includes culture conditions in which one or more cytokine is specifically excluded from the medium. Cytokines are commercially available from several vendors such as, for example, Genzyme (Framingham, Mass.), Genentech (South San Francisco, Calif.), Amgen (Thousand Oaks, Calif.), R&D Systems and Immunex (Seattle, Wash.). It is intended, although not always explicitly stated, that molecules having similar biological activity as wild-type or purified cytokines (e.g., recombinantly produced or muteins thereof) are intended to be used within the spirit and scope of the invention.

"Co-stimulatory molecules" are involved in the interaction between receptor-ligand pairs expressed on the surface of antigen presenting cells and T cells. One exemplary receptor-ligand pair is the B7 co-stimulatory molecules on the surface of DCs and its counter-receptor CD28 or CTLA-4 on T cells (Freeman, et al. (1993) Science 262:909-91 1; Young, et al. (1992) J. Clin. Invest. 90: 229; Nabavi, et al. Nature 360:266). Other important co-stimulatory molecules are CD40, CD54, CD80, CD86.

Patient T cell assays can generally be performed by treating patient PBMCs with the reactive antigens and analyzing the cells for a suitable response. For example, the PBMC supernatant can be assayed for the level of secreted cytokines. Preferably, the cytokine assayed is interferon-gamma, interleukin-2, interleukin-12 (either the p40 subunit or biologically active p70), interleukin-1 or tumor necrosis factor-α. The cytokines interleukin-4 and interleukin-10 can also be assayed, since the levels of these representative Th2-type cytokines generally decrease in response to treatment with a polypeptide as described herein. Cytokines can be assayed, for example, using commercially available antibodies specific for the cytokine of interest in an ELISA format, with positive results determined according to the manufacturer's instructions. Suitable antibodies can be obtained, for example, from Chemicon, Temucula, Calif. and PharMingen, San Diego, Calif. Alternatively, the treated PBMCs can be assayed for mRNA encoding one or more of the cytokines interferon-gamma, interleukin-2, interleukin-12 p40 subunit, interleukin-1 or tumor necrosis factor-α, or the PBMCs can be assayed for a proliferative response as described herein. Alternatively, cytokines can be measured by testing PBMC supernatants for cytokine-specific biological activities.

Method of Diagnosis

According to one aspect of the invention, methods for diagnosing a disorder that is characterized by expression of a leukemia associated nucleic acid or polypeptide are provided. The methods involve contacting a biological sample isolated from a subject with an agent specific for the leukemia associated nucleic acid or polypeptide to detect the presence of the leukemia associated nucleic acid or polypeptide in the biological sample. As used herein, "contacting" means placing the biological sample in sufficient proximity to the agent and under the appropriate conditions of, e.g., concentration, temperature, time, ionic strength, to allow the specific interaction between the agent and leukemia associated nucleic acid or polypeptide that are present in the biological sample. In general, the conditions for contacting the agent with the biological sample are conditions known by those of ordinary skill in the art to facilitate a specific interaction between a molecule and its cognate (e.g., a protein and its receptor cognate, an antibody and its protein antigen cognate, a nucleic acid and its complementary sequence cognate) in a biological sample. Exemplary conditions for facilitating a specific interaction between a molecule and its cognate are described in U.S. Pat. No. 5,108,921, issued to Low et al.

The biological sample can be located in vivo or in vitro. For example, the biological sample can be a hematopoietic tissue in vivo and the agent specific for the leukemia associated nucleic acid or polypeptide can be used to detect the presence of such molecules in the hematopoietic tissue (e.g., for imaging portions of the hematopoietic tissue that express the leukemia associated gene products). Alternatively, the biological sample can be located in vitro (e.g., a blood sample, bone marrow biopsy, tissue extract). In a particularly preferred embodiment, the biological sample can be a cell-containing sample, more preferably a sample containing hematopoietic cells.

The skilled artisan can determine which HLA molecule binds to the CD33 fragments by, e.g., experiments utilizing antibodies to block specifically individual HLA class I molecules. For example, antibodies which bind selectively to HLA-A2 will prevent efficient presentation of antigens specifically presented by HLA-A2. Thus, if the present peptides are presented by HLA-A2, then the inclusion of anti-HLA-A2 antibodies in an in vitro assay will block the presentation of these antigens. An assay for determining the nature of the HLA molecule is found in U.S. Pat. No. 5,939,526.

Vaccine

The present invention also provides vaccine compositions comprising the CD33 antigen peptide fragments or nucleic acids encoding these fragments described above. Vaccines can also be prepared from antigen presenting cells that have been pulsed with the peptides or nucleic acids or immune effector cells which have been exposed to the peptides or nucleic acids. The vaccine can contain a single peptide or a range of peptides which cover different or similar epitopes. In addition or alternatively, the vaccine can be a polyvalent vaccine where a single polypeptide can be provided with multiple epitopes.

In one embodiment the peptide is conjugated to a carrier protein, such as for example a polycation (poly-L-Lysine or poly-L-arginine), tetanus toxoid, diphtheria toxoid or oxidised KLH in order to stimulate T cell help as disclosed in U.S. Pat. No. 6,344,203.

Included as part of the vaccine, substances which potentiate the immune response can be administered with nucleic acid or peptide components in a cancer vaccine. Such immune response potentiating compounds can be classified as either adjuvants or cytokines. Adjuvants can enhance the immunological response by providing a reservoir of antigen (extracellularly or within macrophages), activating macrophages and stimulating specific sets of lymphocytes. Adjuvants of many kinds are well known in the art; specific examples include MPL (SmithKline Beecham), a congener obtained after purification and acid hydrolysis of Salmonella minnesota Re 595 lipopolysaccharide, QS21 (SmithKline Beecham), a pure QA-21 saponin purified from Quillija saponaria extract, and various water-in-oil emulsions prepared from biodegradable oils such as squalene and/or tocopherol. Cytokines are also useful in vaccination protocols as a result of lymphocyte stimulatory properties. Many cytokines useful for such purposes will be known to one of ordinary skill in the art, including interleukin-12 (IL-12) which has been shown to enhance the protective effects of vaccines (Science 268: 1432-1434, 1995).

When administered, the therapeutic compositions of the present invention are administered in pharmaceutically acceptable preparations. Such preparations can routinely contain pharmaceutically acceptable concentrations of salt, buffering agents, preservatives, compatible carriers, supplementary immune potentiating agents such as adjuvants and cytokines and optionally other therapeutic agents.

The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

The therapeutics of the invention can be administered by any conventional route, including injection or by gradual infusion over time. Initial doses can also be followed by booster doses, following immunization protocols standard in the art. The administration may, for example, be oral, intravenous, intraperitoneal, intramuscular, intracavity, subcutaneous, or transdermal. When antibodies are used therapeutically, a preferred route of administration is by pulmonary aerosol. Techniques for preparing aerosol delivery systems containing antibodies are well known to those of skill in the art. Generally, such systems should utilize components which will not significantly impair the biological properties of the antibodies, such as the paratope binding capacity (see, for example, Sciarra and Cutie, "Aerosols," in Remington's Pharmaceutical Sciences, 18th edition, 1990, pp 1694-1712). Those of skill in the art can readily determine the various parameters and conditions for producing antibody aerosols without resort to undue experimentation. When using antisense preparations of the invention, slow intravenous administration is preferred.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives can also be present such as, for example, antimicrobials, antioxidants, chelating agents, and inert gases and the like.

In all cases where cells are used as a vaccine, these can be cells transfected with coding sequences for one or both of the components necessary to provoke a CTL response, or be cells which already express both molecules without the need for transfection. Vaccines also encompass naked DNA or RNA, encoding the present peptides, which can be produced in vitro and administered via injection, particle bombardment, nasal aspiration and other methods. Vaccines of the "naked nucleic acid" type have been demonstrated to provoke an immunological response including generation of CTLs specific for the peptide encoded by the naked nucleic acid (Science 259: 1745-1748, 1993). When "disorder" is used herein, it refers to any pathological condition where the tumor rejection antigen precursor is expressed. An example of such a disorder is cancer, leukemias and lymphomas in particular.

The peptides of the present invention can also be used to elicit or enhance an immune response to an antigen encoded by a DNA vaccine. DNA vaccines encode one or more immunostimulating antigens, such that the antigen is generated in situ. For instance, the DNA vaccine can encode a tumor antigen and, optionally, a peptide as described herein. In such vaccines, the DNA can be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter). Bacterial delivery systems involve the administration of a bacterium (such as Bacillus-Calmette-Guerrin) that expresses an epitope of a leukemia cell antigen on its cell surface. The DNA can be introduced using a viral expression system (e.g., vaccinia or other pox virus, retrovirus, or adenovirus), which can involve the use of a non-pathogenic (defective), replication competent virus. Suitable systems are disclosed, for example, in Fisher-Hoch et al., PNAS 86:317-321, 1989; Flexner et al., Ann. N.Y. Acad. Sci. 569:86-103, 1989; Flexner et al., Vaccine 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, Biotechniques 6:616-627, 1988; Rosenfeld et al., Science 252:431-434, 1991; Kolls et al., PNAS 91:215-219, 1994; Kass-Eisler et al., PNAS 90:11498-11502, 1993; Guzman et al., Circulation 88:2838-2848, 1993; and Guzman et al., Cir. Res. 73:1202-1207, 1993. Techniques for incorporating DNA into such expression systems are well known to those of ordinary skill in the art. The DNA can also be "naked," as described, for example, in published PCT application WO 90/11092, and Ulmer et al., Science 259:1745-1749, 1993, reviewed by Cohen, Science 259:1691-1692, 1993. The uptake of naked DNA can be increased by coating the DNA onto biodegradable beads, which are efficiently transported into the cells.

Method of Treatment

The present invention provides a method of treating individuals suffering from leukemia. In such methods, the introduction of peptides, nucleic acids, protein binding agents, antigen presenting cells and/or immune effector cells as described above serves as an immunotherapeutic, directing and promoting the immune system of the individual to combat leukemic cells that display the CD33 antigen fragments. The methods can comprise administering an effective amount of any of the above compounds to a patient in need of such treatment through the means described above. The methods can further comprise a course of chemotherapy, such as with 5-FU or cisplatin, prior to administration of the above compounds. See, e.g. Int. J. Cancer; 101:265 (2002).

Individuals at risk of developing leukemia, such as those having a genetic predisposition, can be treated with the formulations of the present in a prophylactic attempt to delay or eliminate the onset of the leukemic state. Similarly, those individuals who have already developed cancer and who have been treated to remove the cancer or are otherwise in remission are particularly susceptible to relapse and reoccurrence. As part of a treatment regimen, such individuals can be immunized against the cancer that they have been diagnosed as having had in order to combat a recurrence. Thus, once it is known that an individual has had a type of cancer and is at risk of a relapse, they can be immunized in order to prepare their immune system to combat any future appearance of the cancer.

Therapeutic approaches based upon the disclosure are premised on a response by a subject's immune system, potentially leading to lysis of leukemia cells. One such approach is the administration of autologous CTLs specific to the complex to a subject with abnormal cells of the phenotype at issue. It is within the skill of the artisan to develop such CTLs in vitro. Generally, a sample of cells taken from a subject, such as blood cells, are contacted with a cell presenting the complex and capable of provoking CTLs to proliferate. The target cell can be a transfectant. These transfectants present the desired complex of their surface and, when combined with a CTL of interest, stimulate its proliferation. Specific production of a CTL is well known to one of ordinary skill in the art. The clonally expanded autologous CTLs can then be administered to the subject.

In one therapeutic methodology, referred to as adoptive transfer (Greenberg, J. Immunol. 136(5): 1917, 1986; Riddel et al., Science 257: 238, 1992; Lynch et al, Eur. J. Immunol. 21: 1403-1410, 1991; Kast et al., Cell 59: 603-614, 1989), cells presenting the desired complex are combined with CTLs leading to proliferation of the CTLs specific thereto. The proliferated CTLs are then administered to a subject with a cellular abnormality which is characterized by certain of the abnormal cells presenting the particular complex. The CTLs can then lyse the abnormal cells, thereby achieving the desired therapeutic goal.

The foregoing therapy assumes that at least some of the subject's abnormal cells present the relevant HLA complex. This can be determined very easily, as the art is very familiar with methods for identifying cells which present a particular HLA molecule, as well as how to identify cells expressing DNA of the pertinent sequences, in this case a leukemia associated gene sequence. Once cells presenting the relevant complex are identified via the foregoing screening methodology, they can be combined with a sample from a patient, where the sample contains CTLs. If the complex presenting cells are lysed by the mixed CTL sample, then it can be assumed that a leukemia associated gene is being presented, and the subject is an appropriate candidate for the therapeutic approaches set forth herein.

Adoptive transfer is not the only form of therapy that is available in accordance with the invention. CTLs can also be provoked in vivo, using a number of approaches. One approach is the use of non-proliferative cells expressing the complex, such as antigen presenting cells. The cells used in this approach can be those that normally express the complex, such as irradiated tumor cells or cells transfected with one or both of the genes necessary for presentation of the complex. Chen et al., Proc. Natl. Acad. Sci. USA 88: 110-114 (1991) exemplifies this approach, showing the use of transfected cells expressing HPV E7 peptides in a therapeutic regime. Various cell types can be used. Similarly, vectors carrying one or both of the genes of interest can be used. Viral or bacterial vectors are especially preferred. The nucleic acid can be incorporated into an expression vector. Expression vectors can be unmodified extrachromosomal nucleic acids, plasmids or viral genomes constructed or modified to enable insertion of exogenous nucleic acids, such as those encoding the present peptides. Nucleic acids encoding these peptides can also be inserted into a retroviral genome, thereby facilitating integration of the nucleic acid into the genome of the target tissue or cell type. In these systems, the gene of interest is carried by a microorganism, e.g., a Vaccinia virus, retrovirus or the bacteria BCG, and the materials defacto "infect" host cells. The cells which result present the complex of interest, and are recognized by autologous CTLs, which then proliferate.

Kits

The invention also provides isolated proteins and peptides, and antibodies to those proteins and peptides. Kits containing any of the foregoing molecules, alone or in combination, are additionally provided. The foregoing can be used in the diagnosis or treatment of conditions characterized by the expression of the present peptides. The kits can also be used to pulse antigen presenting cells or t-lymphocytes, and, as such, can contain appropriate culture media, culture media supplements such as cytokines, disposable laboratory equipment and the like. Examples of such kit components can be found in the following examples.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions can be employed in conjunction with other therapeutic compounds.

The invention in another aspect involves a kit for detecting the presence of the expression of the present polypeptide. Such kits employ two or more of the above-described nucleic acid molecules isolated in separate containers and packaged in a single package. In one such kit, a pair of isolated nucleic acid molecules is provided. In certain embodiments, the pair of isolated nucleic acid molecules are PCR primers.

The invention also embraces so-called expression kits, which allow the artisan to prepare a desired expression vector or vectors. Such expression kits include at least separate portions of each of the previously discussed coding sequences. Other components can be added, as desired, as long as the previously mentioned sequences, which are required, are included.

This invention is further illustrated by the following non-limiting examples.

EXAMPLES

Example 1

A total of 364 amino acids of CD33 protein, listed above as SEQ ID NO: 4, were retrived from the SWISS-PROT databank and analyzed for HLA-A2.1 binding epitopes as nonamers by the peptide motif search software SYFPEITHI which is supported by DFG-Sonderforschungsbereich 510 and the European Union: EU BIOMED CT95-1627, BIOTECH CT95-0263, and EU QLQ-CT-1999-00713. The algorithms used are based on the book "MHC Ligands and Peptide Motifs" by H. G. Rammensee, J. Bachmann and S. Stevanovic. The prediction of the SYFPEITHI program is based on published motifs (pool sequencing, natural ligands) and the score is calculated by the consideration of specific amino acids of the peptide in a numeric value depending on whether they are carrying anchor, auxiliary anchor, or preferred residue. Ideal anchors are given 10 points, unusual anchors 6-8 points, auxiliary anchors 4-6 points and preferred residues 1-4 points. Amino acids that are regarded as having a negative effect on the binding are given values between −1 and −3. Besides a prediction for binding, the preferred amino acids in the peptide of CD33 antigen were examined for the possible immunogenic epitopes.

Based on high HLA-A2.1 binding scores, several 9 mer fragments of the CD33 peptide SEQ ID NO: 4) were identified using SYFPEITHI software and are listed below. The score means the calculated potential capability for binding to a HLA-A2 molecule.

| Position | 1 | 2 | 3 | 4 | 5 | 6 | 7 | 8 | 9 | Score | SEQ ID NO: |
|---|---|---|---|---|---|---|---|---|---|---|---|
| 269 | A | L | L | A | L | C | L | C | L | 26 | 8 |
| 270 | L | L | A | L | C | L | C | L | I | 26 | 42 |
| 2 | P | L | L | L | L | L | P | L | L | 25 | 43 |
| 4 | L | L | L | L | P | L | L | W | A | 24 | 44 |
| 65 | A | I | I | S | G | D | S | P | V | 24 | 2 |
| 133 | Q | L | S | V | H | V | T | D | L | 24 | 45 |
| 276 | C | L | I | F | F | I | V | K | T | 24 | 46 |
| 147 | I | L | I | P | G | T | L | E | P | 23 | 47 |
| 5 | L | L | L | P | L | L | W | A | G | 22 | 48 |
| 30 | T | V | Q | E | G | L | C | V | L | 22 | 49 |
| 179 | W | L | S | A | A | P | T | S | L | 22 | 50 |
| 226 | T | I | Q | L | N | V | T | Y | V | 22 | 9 |
| 9 | L | L | W | A | G | A | L | A | M | 21 | 51 |
| 34 | G | L | C | V | L | V | P | C | T | 21 | 52 |
| 6 | L | L | P | L | L | W | A | G | A | 20 | 53 |
| 74 | A | T | N | K | L | D | Q | E | V | 20 | 54 |
| 261 | A | I | G | G | A | G | V | T | A | 20 | 55 |
| 274 | C | L | C | L | I | F | F | I | V | 20 | 56 |
| 15 | L | A | M | D | P | N | F | W | L | 19 | 57 |
| 262 | I | G | G | A | G | V | T | A | L | 19 | 58 |
| 263 | G | G | A | G | V | T | A | L | L | 19 | 59 |
| 267 | V | T | A | L | L | A | L | C | L | 19 | 60 |
| 1 | M | P | L | L | L | L | L | P | L | 18 | 61 |
| 221 | V | T | T | E | R | T | I | Q | L | 18 | 62 |
| 265 | A | G | V | T | A | L | L | A | L | 18 | 63 |
| 315 | K | L | H | G | P | T | E | T | S | 18 | 64 |
| 66 | I | I | S | G | D | S | P | V | A | 17 | 65 |
| 77 | K | L | D | Q | E | V | Q | E | E | 17 | 66 |
| 140 | D | L | T | H | R | P | K | I | L | 17 | 67 |
| 160 | N | L | T | C | S | V | S | W | A | 17 | 68 |
| 172 | G | T | P | P | I | F | S | W | L | 17 | 69 |
| 191 | T | T | H | S | S | V | L | I | I | 17 | 70 |
| 259 | H | G | A | I | G | G | A | G | V | 17 | 71 |
| 273 | L | C | L | C | L | I | F | F | I | 17 | 72 |
| 324 | S | C | S | G | A | A | P | T | V | 17 | 73 |
| 3 | L | L | L | L | L | P | L | L | W | 16 | 74 |
| 23 | L | Q | V | Q | E | S | V | T | V | 16 | 75 |
| 29 | V | T | V | Q | E | G | L | C | V | 16 | 76 |
| 148 | L | I | P | G | T | L | E | P | G | 16 | 77 |
| 186 | S | L | G | P | R | T | T | H | S | 16 | 78 |

| Position | 1 | 2 | 3 | 4 | 5 | 6 | 7 | 8 | 9 | Score | SEQ ID NO: |
|---|---|---|---|---|---|---|---|---|---|---|---|
| 209 | N | L | T | C | Q | V | K | F | A | 16 | 79 |
| 241 | G | I | F | P | G | D | G | S | G | 16 | 80 |
| 249 | G | K | Q | E | T | R | A | G | V | 16 | 81 |
| 257 | V | V | H | G | A | I | G | G | A | 16 | 82 |
| 272 | A | L | C | L | C | L | I | F | F | 16 | 83 |
| 333 | E | M | D | E | E | L | H | Y | A | 16 | 84 |
| 7 | L | P | L | L | W | A | G | A | L | 15 | 85 |
| 8 | P | L | L | W | A | G | A | L | A | 15 | 86 |
| 14 | A | L | A | M | D | P | N | F | W | 15 | 87 |
| 21 | F | W | L | Q | V | Q | E | S | V | 15 | 88 |
| 31 | V | Q | E | G | L | C | V | L | V | 15 | 89 |
| 37 | V | L | V | P | C | T | F | F | H | 15 | 90 |
| 98 | R | N | N | C | S | L | S | I | V | 15 | 91 |
| 128 | S | Y | K | S | P | Q | L | S | V | 15 | 92 |
| 141 | L | T | H | R | P | K | I | L | I | 15 | 93 |
| 152 | T | L | E | P | G | H | S | K | N | 15 | 94 |
| 175 | P | I | F | S | W | L | S | A | A | 15 | 95 |
| 213 | Q | V | K | F | A | G | A | G | V | 15 | 96 |
| 260 | G | A | I | G | G | A | G | V | T | 15 | 97 |
| 277 | L | I | F | F | I | V | K | T | H | 15 | 98 |
| 326 | S | G | A | A | P | T | V | E | M | 15 | 99 |
| 330 | P | T | V | E | M | D | E | E | L | 15 | 100 |
| 353 | D | T | S | T | E | Y | S | E | V | 15 | 101 |
| 22 | W | L | Q | V | Q | E | S | V | T | 14 | 102 |
| 70 | D | S | P | V | A | T | N | K | L | 14 | 103 |
| 91 | R | L | L | G | D | P | S | R | N | 14 | 104 |
| 92 | L | L | G | D | P | S | R | N | N | 14 | 105 |
| 97 | S | R | N | N | C | S | L | S | I | 14 | 106 |
| 102 | S | L | S | I | V | D | A | R | R | 14 | 107 |
| 130 | K | S | P | Q | L | S | V | H | V | 14 | 108 |
| 157 | H | S | K | N | L | T | C | S | V | 14 | 109 |
| 168 | A | C | E | Q | G | T | P | P | I | 14 | 110 |
| 197 | L | I | I | T | P | R | P | Q | D | 14 | 111 |
| 253 | T | R | A | G | V | V | H | G | A | 14 | 112 |
| 347 | G | M | N | P | S | K | D | T | S | 14 | 113 |
| 59 | Y | W | F | R | E | G | A | I | I | 13 | 114 |
| 85 | E | T | Q | G | R | F | R | L | L | 13 | 115 |
| 139 | T | D | L | T | H | R | P | K | I | 13 | 116 |
| 151 | G | T | L | E | P | G | H | S | K | 13 | 117 |
| 153 | L | E | P | G | H | S | K | N | L | 13 | 118 |
| 188 | G | P | R | T | T | H | S | S | V | 13 | 119 |
| 190 | R | T | T | H | S | S | V | L | I | 13 | 120 |
| 196 | V | L | I | I | T | P | R | P | Q | 13 | 121 |
| 215 | K | F | A | G | A | G | V | T | T | 13 | 122 |
| 216 | F | A | G | A | G | V | T | T | E | 13 | 123 |
| 228 | Q | L | N | V | T | Y | V | P | Q | 13 | 124 |
| 234 | V | P | Q | N | P | T | T | G | I | 13 | 125 |
| 254 | R | A | G | V | V | H | G | A | I | 13 | 126 |
| 291 | R | T | A | V | G | R | N | D | T | 13 | 127 |
| 298 | D | T | H | P | T | T | G | S | A | 13 | 128 |
| 327 | G | A | A | P | T | V | E | M | D | 13 | 129 |
| 10 | L | W | A | G | A | L | A | M | D | 12 | 130 |
| 16 | A | M | D | P | N | F | W | L | Q | 12 | 131 |
| 17 | M | D | P | N | F | W | L | Q | V | 12 | 132 |
| 126 | K | Y | S | Y | K | S | P | Q | L | 12 | 133 |
| 146 | K | I | L | I | P | G | T | L | E | 12 | 134 |
| 181 | S | A | A | P | T | S | L | G | P | 12 | 135 |
| 206 | H | G | T | N | L | T | C | Q | V | 12 | 136 |
| 219 | A | G | V | T | T | E | R | T | I | 12 | 137 |
| 231 | V | T | Y | V | P | Q | N | P | T | 12 | 138 |
| 314 | S | K | L | H | G | P | T | E | T | 12 | 139 |
| 335 | D | E | E | L | H | Y | A | S | L | 12 | 140 |
| 340 | Y | A | S | L | N | F | H | G | M | 12 | 141 |
| 342 | S | L | N | F | H | G | M | N | P | 12 | 142 |
| 39 | V | P | C | T | F | F | H | P | I | 11 | 143 |
| 68 | S | G | D | S | P | V | A | T | N | 11 | 144 |
| 95 | D | P | S | R | N | N | C | S | L | 11 | 145 |
| 104 | S | I | V | D | A | R | R | R | D | 11 | 146 |
| 119 | R | M | E | R | G | S | T | K | Y | 11 | 147 |
| 131 | S | P | Q | L | S | V | H | V | T | 11 | 148 |
| 145 | P | K | I | L | I | P | G | T | L | 11 | 149 |
| 195 | S | V | L | I | I | T | P | R | P | 11 | 150 |
| 198 | I | I | T | P | R | P | Q | D | H | 11 | 151 |
| 202 | R | P | Q | D | H | G | T | N | L | 11 | 152 |
| 218 | G | A | G | V | T | T | E | R | T | 11 | 153 |
| 223 | T | E | R | T | I | Q | L | N | V | 11 | 154 |
| 225 | R | T | I | Q | L | N | V | T | Y | 11 | 155 |
| 266 | G | V | T | A | L | L | A | L | C | 11 | 156 |
| 281 | I | V | K | T | H | R | R | K | A | 11 | 157 |
| 305 | S | A | S | P | K | H | Q | K | K | 11 | 158 |
| 24 | Q | V | Q | E | S | V | T | V | Q | 10 | 159 |
| 48 | P | Y | Y | D | K | N | S | P | V | 10 | 160 |
| 58 | G | Y | W | F | R | E | G | A | I | 10 | 161 |
| 67 | I | S | G | D | S | P | V | A | T | 10 | 162 |
| 78 | L | D | Q | E | V | Q | E | E | T | 10 | 163 |
| 100 | N | C | S | L | S | I | V | D | A | 10 | 164 |
| 144 | R | P | K | I | L | I | P | G | T | 10 | 165 |
| 182 | A | A | P | T | S | L | G | P | R | 10 | 166 |
| 217 | A | G | A | G | V | T | T | E | R | 10 | 167 |
| 250 | K | Q | E | T | R | A | G | V | V | 10 | 168 |
| 264 | G | A | G | V | T | A | L | L | A | 10 | 169 |
| 268 | T | A | L | L | A | L | C | L | C | 10 | 170 |
| 271 | L | A | L | C | L | C | L | I | F | 10 | 171 |
| 286 | R | R | K | A | A | R | T | A | V | 10 | 172 |
| 288 | K | A | A | R | T | A | V | G | R | 10 | 173 |
| 289 | A | A | R | T | A | V | G | R | N | 10 | 174 |
| 295 | G | R | N | D | T | H | P | T | T | 10 | 175 |
| 308 | P | K | H | Q | K | K | S | K | L | 10 | 176 |
| 323 | S | S | C | S | G | A | A | P | T | 10 | 177 |
| 355 | S | T | E | Y | S | E | V | R | T | 10 | 178 |

The following peptides were tested for their ability to bind to HLA-A2.1+ T2 cells and their binding scores under Brefeldin A treatment. Eur. J. Immunol. 2000.30:3411-3421. This experiment was performed to measure the peptide/HLA-A2.1 complex stability using the native or modified CD33 peptide. As the immunogenicity of peptides depends primarily on their capacity to stabilize the HLA-A2.1 molecules, more stable peptide to HLA-A2.1 could generate more effective cytotoxic T cells to leukemia cells.

| | Peptide Sequence | Brefeldin A treatment | | | | | |
|---|---|---|---|---|---|---|---|
| | | None | 0 hr | 2 hr | 4 hr | 6 hr | Overnight |
| T2 alone | | 215 | 226 | 200 | 187 | 157 | 255 |
| SEQ ID NO: 42 | LLALCLCLI | 204 | 304 | 280 | 233 | 213 | 193 |
| SEQ ID NO: 2 | AIISGDSPV | 566 | 647 | 332 | 188 | 142 | 428 |
| SEQ ID NO: 3 | YIISGDSPV | 547 | 641 | 588 | 380 | 216 | 248 |
| SEQ ID NO: 10 | YIGSGDSPV | 515 | 687 | 285 | 167 | 151 | 280 |
| SEQ ID NO: 11 | YIIIGDSPV | 263 | 301 | 257 | 208 | 172 | 325 |
| SEQ ID NO: 12 | YIILGDSPV | 465 | 488 | 315 | 205 | 173 | 323 |
| SEQ ID NO: 6 | YIISGISPV | 591 | 840 | 929 | 839 | 680 | 593 |
| SEQ ID NO: 13 | YIISGDLPV | 619 | 724 | 524 | 307 | 203 | 296 |
| SEQ ID NO: 14 | YIISGDSWV | 209 | 247 | 247 | 208 | 173 | 298 |

-continued

| | | Brefeldin A treatment | | | | | |
| | Peptide Sequence | None | 0 hr | 2 hr | 4 hr | 6 hr | Overnight |
| --- | --- | --- | --- | --- | --- | --- | --- |
| SEQ ID NO: 15 | YIISGDSPL | 428 | 426 | 334 | 217 | 168 | 157 |
| SEQ ID NO: 7 | YLISGDSPV | 701 | 728 | 810 | 745 | 594 | 479 |
| SEQ ID NO: 16 | ALISGDSPV | 603 | 677 | 882 | 692 | 609 | 366 |
| SEQ ID NO: 9 | TIQLNVTYV | 175 | 218 | 173 | 180 | 159 | 404 |

As can be seen from these results, the peptides of SEQ ID NOS: 6, 7 and 16 gave good and prolonged stable binding. Several other peptides provided good initial binding over baseline values.

Example 2

The present example illustrates that that the present peptides are capable of inducing a T-lymphocyte response. In this example, antigen presenting cells were pulsed at 150 micrograms of each peptide per 1 million antigen presenting cells with the following amino acid sequences:

(1) YLALCLCLI (SEQ ID NO: 1);
(2) AIISGDSPV (SEQ ID NO: 2); and
(3) YIISGDSPV (SEQ ID NO: 3).

Other peptides that include the sequences listed above can be similarly tested by the skilled artisan in the course of normal experimentation to determine whether peptides including any of the recited sequences can be effectively used as described herein.

The antigen presenting cells were then contacted with effector cells at a target effector ration of 1:60. The effector cells were then contacted with HLA-A2.1 positive ML-2 cells and the cytotoxicity to the ML-2 cells were measured. ML-2 cells are acute myeloid leukemia cells (AML) cells which are HLA-A2.1 positive. The results are set forth in Table 1.

TABLE 1

| Experiment Number | Antigen Presenting Cells | Donor | CD33 Peptide (SEQ ID NO:) | Number of Stimulations | Cytoxicity to ML-1 Cells by Cytokines (%) | | Cytotoxicity to AML Patient's Bone Marrow (%) |
| --- | --- | --- | --- | --- | --- | --- | --- |
| Control | None | B, F, G | None | 0 | 0, 0, 7 | | |
| 1 | DC | A | 2 | 2 | 37 | | |
| 2 | DC | B | 2 | 2 | 42 | | 43 |
| 3 | DC | C | 2 | 2 | 39 | | 63 |
| 4 | DC | D | 2 | 2 | 29 | | |
| 5 | DC | E | 3 | 2 | 37 | | |
| 6 | T2 | F | 1 | 2 | 3 | 21 | 36 |
| 7 | T2 | G | 1 | 2 | 3 | 34 | 64 |
| 8 | T2 | F | 2 | 2 | 3 | 33 | 56 |
| 9 | T2 | G | 2 | 2 | 3 | 35 | 55 |

Table 2 shows the expression levels of different types of effector cells contacted with antigen presenting cells pulsed with examples of peptides of the present invention. Results are shown in mean fluorescence intensity. Peptides inducing 20% or greater cytotoxicity are generally considered to promote significant cytotoxicity. Testing the cytotoxicity level of an effector cell exposed to a peptide is a major method for measuring the effectiveness for the peptide.

TABLE 2

| Antigen Presenting Cells | Donor | CD33 Peptide (SEQ ID NO:) | Number of Stims | Expression levels of: | | | | | | |
| --- | --- | --- | --- | --- | --- | --- | --- | --- | --- | --- |
| | | | | CD45RO Memory | | CD95 Activation | | CD4 T helper | | CD8 T cytotoxic |
| None | F, G | None | 0 | 420 | | 24 | | 120 | | 2430 |
| DC | C | 2 | 2 | 1851 | | 110 | | 332 | | 2477 |
| DC | D | 2 | 2 | 2593 | | 172 | | 356 | | 2332 |
| T2 | F | 2 | 2  3 | 2146 | 1963 | 77 | 127 | 51 | 49 | 6267  7793 |
| T2 | G | 2 | 2  3 | 1575 | 1591 | 133 | 152 | 31 | 36 | 8070  8187 |
| T2 | F | 1 | 2 | 1262 | | 99 | | 81 | | 3381 |
| T2 | G | 1 | 2 | 1432 | | 102 | | 57 | | 7796 |

Figure 1B:
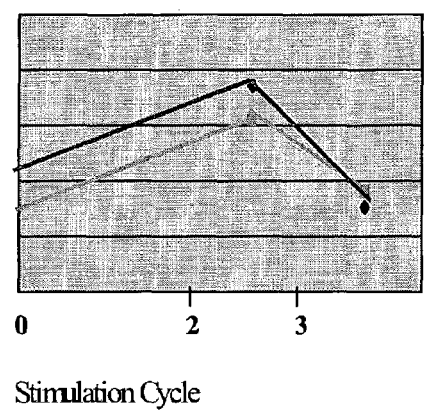
FIG. 1B shows IFN-γ production of CTLs stimulated by T2 cells pulsed with the AIISGDSPV (SEQ ID NO: 2) peptide.

FIG. 1A shows IFN-γ release by cytotoxic T-lymphocytes (CTLs) from two different HLA-A2.1+ (shown as diamond or box) donors stimulated by dendritic cells pulsed three times, once a week with the AIISGDSPV (SEQ ID NO:2) peptide. FIG. 1B shows IFN-γ released by CTLs stimulated by T2 cells pulsed as above with the AIISGDSPV (SEQ ID NO:2) peptide. As can be seen from these FIGS., the highest IFN-γ release was observed when the CTLs were stimulated twice. IFN-γ amount is shown in picogram/milliliter. The scale for FIG. 1B is the same as for FIG. 1A.

The following peptide has also been determined to be immunogenic in similar experiments, ALISGDSPV (SEQ ID NO: 16).

Example 3

The search software SYFPEITHI was used to identify the potential peptide motifs to HLA-A2.1-specific CD33 epitopes. Among the peptides predicted, four peptides were selected and synthesized (>95% pure) for evaluation based on high scores for HLA-A2.1 binding and the presence of primary HLA-A2.1 anchor residues. T2 cells, a transporter antigen processing (TAP) gene-deficient cell line which express only HLA-A2.1 MHC class I molecules (Zweerink et al., 1993), were used to evaluate CD33 peptide specific binding to HLA-A2.1 on the cells. Influenza virus matrix peptide 58-66 (GILGFVFTL SEQ ID NO: 179), which is known to bind very tightly to HLA-A2.1, was used as an HLA-A2.1-specific control peptide.

Peptide Synthesis

Four potential HLA-A2.1-specific CD33 epitopes: LLALCLCLI (residues 270-278, SEQ ID NO: 42), ALLALCLCL (residues 269-277, SEQ ID NO: 8), AIISGDSPV (residues 65-73, SEQ ID NO: 2) and TIQLNVTYV (residues 226-234, SEQ ID NO:9) were synthesized by standard fmoc (9-fluorenylmethyl-oxycarbonyl) chemistries and were purified to >90% using reverse-phase chromatography (Biosynthesis, Lewisville, Tex.). A HLA-A2.1-specific influenza virus protein matrix peptide (GILGFVFTL: residues 58-66, SEQ ID NO: 179) was synthesized and used as a positive control in these studies. The identity of each peptide was validated by mass-spectrometry for molecular weight.

Cell Lines

AML cell lines, EOL-1 (DSMZ, Braunschweig, Germany), Kasumi-1 (DSMZ), HL-60 (ATCC, Manassas, Va.), SR-91 (ATCC), THP-1 (ATCC), ML-2 (gift from Dr. Y. Matsuo, Okayama, Japan) were maintained in liquid culture in RPMI 1640 and 10% fetal calf serum (FCS; Biowhittaker, Walkersville, Md.). In addition, the AML cell lines, UT-2 (alpha-MEM, 20% FCS, 5 ng/ml GM-CSF), OCI-AML5 (alpha-MEM, 20% FCS, 10 ng/ml GM-CSF), and MUTZ-2 (alpha-MEM, 20% FCS, 50 ng/ml SCF) were purchased from DSMZ (Braunschweig, Germany). T2 cells, a human B and T cell hybrid expressing HLA-A2.1, were maintained in RPMI 1640 plus 20% FCS and used as antigen presenting cells in these studies.

Reagents

Monoclonal mouse anti-HLA-A2.1 antibody was purified from the culture supernatant of the hybridoma BB7.2 cell line (ATCC). Recombinant human GM-CSF and CD40 ligand were obtained from Immunex (Seattle, Wash.). Recombinant human IL-2, IL-4, IL-6, IL-7, IFN-α, IFN-γ, TNF-α, and IL-12 were purchased from R&D Systems (Minneapolis, Minn.). Mouse anti-human monoclonal antibodies (CD40, CD69, CD80, CD83, and CD86) conjugated with either FITC or PE were purchased from Immunotech (Hialeigha, Fla.), and either fluorecently labeled or purified antibodies to CD3, CD4, CD8, CD14, CD28, CD33, CD45RA, CD45RO and HLA-DR were purchased from Becton Dickinson Pharmingen (San Diego, Calif.). Purified lipopolysacchride (LPS) prepared from *Escherichia coli* O:113 was obtained from the National Institute of Health (Bethesda, Md.).

MHC Peptide Binding Assay

The assay for peptide binding to HLA-A2.1 was performed (Nijman et al., 1993) using the TAP-deficient T2 hybrid cell line, which is known to up-regulate HLA-A2.1 expression on the cell surface by acquiring only exogenous epitope (Salter et al., 1986; Zweerink et al., 1993). T2 cells were washed and resuspended in serum-free AIM-V™ (Gibco-Life Technologies, Rockville, Md.) at a final concentration of $1 \times 10^6$ cells/ml and transferred into a 24-well tissue culture plate. Cells were pulsed with respective CD33 peptides at different concentrations (5-150 μg/ml) or influenza virus protein matrix peptide (30 μg/ml) plus 3 μg human β2-microglobulin (Sigma), and incubated for overnight at 37° C., 5% $CO_2$ in humidified air. After incubation, cells were washed once with PBS containing 3% FCS, and stained with mouse anti-HLA-A2.1 monoclonal antibody for 15 minutes at 4° C. After washing, the cells were incubated with goat anti-mouse IgG (F(ab')$_2$)-FITC for 15 minutes at 4° C. The cells were washed once, and fluorescence was measured on a FACSort™ flow cytometer (Becton Dickson, San Jose, Calif.). The fluorescence index was calculated as follows: (mean channel fluorescence of sample–mean channel fluorescence of unstained control cells)/mean channel fluorescence of unstained control cells.

Cell Isolation

Peripheral blood mononuclear cells (PBMCs) were isolated from heparinized whole blood of healthy HLA-A2.1+ donors by standard gradient centrifugation with Ficoll-Paque™ Plus (Amersham Pharmacia Biotech AB, Uppsala Sweden). PBMCs were harvested from the interface, washed twice, and resuspended in PBS supplemented with 5 mM EDTA and 0.5% human serum albumin. Informed consent was obtained from all donors and the protocol was approved by the Rush Medical School Institutional Review Board.

Monocytes. CD14+ monocytes were separated from PBMCs using a magnetic sorting technique (Miltenyi Biotec, Auburn, Calif.). PBMCs were incubated with colloidal superparamagnetic microbeads conjugated with anti-human CD14 mAb for 15 minuates at 4° C., and passed over a column in a magnetic field. After washing, positively enriched CD14+ cells were eluted from the magnetic columns. Purity (mean±standard deviation) of CD 14+ monocytes was examined by flow cytometry and was found to be 92+4%.

T cells. CD3+ T cells were isolated from the monocyte depleted cell fractions using the Pan T cell isolation kit from Miltenyi Biotec. The T cell isolation was done by depletion of B cells, NK cells, early erythroid cells, platelets and basophils by indirectly labeling with a cocktail of hapten-conjugated CD11b, CD16, CD19, CD36 and CD56 antibodies, and MACs microbeads coupled to an anti-hapten monoclonal antibody. The effluent (negative fraction cells) was collected from the column as the enriched CD3+ T cell fraction. Purity (mean standard deviation) of CD3+ T cells was examined by flow cytometry and was found to be 94+4%.

Dendritic Cell (DC) Generation

Immature DCs were generated according to modified protocols of Romani et al. (1994) and Bakker et al. (1995). Briefly, fresh or frozen/thawed CD14+ cells were cultured in RPMI 1640 medium (Gibco-Life Technologies) supplemented with 10% FCS, 1,000 U/ml GM-CSF and 1,000 U/ml IL-4. The cell cultures were fed with fresh medium and GM- CSF and IL-4 every other day and cell differentiation was monitored by light microscopy. On day 7, the cultures were supplemented with different combinations of DC maturation factors such as lipopolysaccharide (100 U/ml), TNF-α (10 ng/ml), or IFN-α (1,000 U/ml) plus TNF-α (10 ng/ml). After three days of incubation, mature DCs (mDC) were harvested and evaluated for their phenotypes by flow cytometry. The maturation factor(s) yielding optimal DC maturation was determined and used to generate mDCs for peptide pulsing in upcoming studies.

Induction of Peptide-Specific CTLs

Two different types of antigen-presenting cells (APCs), mDCs and T2 cells, were used to generate CD33 peptide-specific CTLs. APCs were washed three times in serum-free AIM-V™ culture media and pulsed with peptide at 150 μg/ml for overnight in the media. The peptide-loaded APCs were then irradiated at 10 Gy, washed once, and resuspended in RPMI 1640 media supplemented with 10% human AB serum (Biowhittaker, Walkersville, Md.). Peptide-pulsed APCs were used to prime autologous CD3+ T cells at a 1:20 stimulator-to-responder cell ratio in RPMI 1640 media supplemented with 10% human AB serum, 5 ng/ml IL-6, 20 ng/ml IL-7, and 1 ng/ml IL-12. CTL cultures were restimulated weekly for a total of 3 cycles of stimulation. IL-2 (50 U/ml) was added to the culture one day after the second stimulation and the cells were fed three times a week with fresh medium containing the cytokines.

Cytotoxicity Asay

The cytolytic activity of the CD33 peptide-specific CTLs was measured in a standard $^{51}$Cr-release assay. The CTLs (effector cells) were seeded with $^{51}$Cr-labeled $5\times10^3$ AML cells (target cells) per well at various effector:target cell ratios in 96-well U-bottom microtiter plates and incubated for 4 hours at 37° C., 5% $CO_2$. The $^{51}$Cr-release was measured in 100 μl supernatant using a Beckman LS6500 liquid scintillation counter (Beckman Coulter, Brea, Calif.). The percent specific cell lysis was calculated as [(experimental release−spontaneous release)÷(maximum release−spontaneous release)]. Maximum release was determined from detergent-releasable target cell counts and spontaneous release was the target cell counts determined in the absence of CTLs.

Cold Target Inhibition Assays

Antigen-specific lysis was evaluated in a cold target inhibition assay by analyzing the capacity of unlabeled AML cells (ML-2) to block lysis of $^{51}$Cr-labeled AML cells. Effector cells were incubated with an equal number of the unlabeled "cold" target cells (ML-2) for 1 hour at 37° C., 5% $CO_2$ before the addition of $^{51}$Cr-labeled "hot" AML target cells. After a 4-hour incubation, the supernatants (100 ul) were harvested and the specific $^{51}$Cr-release was measured. The inhibition of AML-specific lysis was measured by comparing the percent cytotoxicity of the effector cells incubated with or without the unlabeled "cold" target cells.

IFN-γ Release by CD33 Peptide-Specific CTLs

IFN-γ release by the CTLs was measured using an IFN-γ ELISA kit (PBL-Biomedical Lab., Piscataway, N.J.). Briefly, IFN-γ standards or the supernatant from CD33 peptide-specific CTL cultures were transferred into a 96-well plate pre-coated with anti-human IFN-γ capture monoclonal antibody and incubated for 1 hour in a closed chamber at 24° C. After washing the plate with PBS/0.05% Tween 20, anti-human IFN-γ antibody was added to the wells and incubated for 1 hour at 24° C. Wells were then developed by incubation with horseradish peroxidase conjugate and TMB substrate solution. Stop solution was added to each well and the absorbance was determined at 450 nm with a SpectraMAX Plus plate reader (Stratagene, La Jolla, Calif.). The amount of cytokine present in the CTL culture supernatant was calculated based on the IFN-γ standard curve.

Phenotypic Analysis of CD33 Peptide-Specific CTLs

CTLs were stained with anti-CD8-FITC, -CD45RA-FITC or -CD28-PE, -CD45RO-PE, or -CD69-PE monoclonal antibodies for 15 minutes at 4° C. After incubation, the cells were washed and analyzed by flow cytometry. Live gating of the forward and scatter channels was used to exclude debris and to selectively acquire the lymphocyte population for analysis. Individual fluorescence data were determined using CellQuest™ v2.1 acquisition and analysis software (Becton Dickinson).

Peptide-MHC Tetramer Staining

Streptavidin-PE-labeled HLA-2.1/AIISGDSPV (SEQ ID NO:2) tetramer was produced by Beckman Coulter using the methods described by Altman et al. (1996). Two-color flow cytometry assays were performed by stainings with anti-CD8-FITC and tetramer-PE. Briefly, the CTLs ($2 \times 10^5$ cells) were stained with 300 ng of tetramer and incubated for 30 minutes at 37° C. After a washing, the cells were stained with anti-CD8- FITC mAb for 15 minutes at 4° C. Cells were washed and analyzed by flow cytometry.

Results

Identification of HLA-A2.1-Specific CD33 Epitope

The results, expressed as the Fluorescence Index (HLA-A2.1 mean channel fluorescence T2 cells pulsed with β2 microglobulin and CD33 peptide ÷ HLA-A2.1 mean channel fluorescence T2 cells pulsed with β2 microglobulin) were used to select the best HLA-A2.1 binding CD33-peptide. A Fluorescence Index (FI) of > 1.0 indicates the up- regulation of HLA-A2.1 molecules by peptide binding on the surface of T2 cells. The peptide AIISGDSPV (SEQ ID NO:2) displayed the highest level of HLA-A2.1 binding (FI=2.81) (Table 3). Based on these results, the peptide AIISGDSPV (SEQ ID NO:2) was chosen for evaluation as a potential immunogenic epitope to generate CD33-specific CTLs against AML cells.

TABLE 3

Peptide binding assay for HLA-A2.1-specific CD33 peptides

| Samples | Peptide Sequence | CD33 Protein Domain | Fluorescence Index* |
|---|---|---|---|
| T2 + β2-microglobulin | | | 1.0 |
| T2 + β2-microglobulin, pulsed with Influenza virus matrix protein peptide$_{58-66}$ | GILGFVFTL (SEQ ID NO: 179) | | 3.11 |
| CD33$_{270-278}$ | LLALCLCLI (SEQ ID NO: 42) | Trans-membrane | 1.19 |
| CD33$_{269-277}$ | LLALCLCLI (SEQ ID NO: 42) | Trans-membrane | 1.04 |
| CD33$_{65-73}$ | AIISGDSPV (SEQ ID NO: 42) | Extracellular | 2.81 |
| CD33$_{226-234}$ | TIQLNVTYV (SEQ ID NO: 9) | Extracellular | 0.99 |

*Fluorescence Index = [HLA-A2.1 mean channel fluorescence T2 cells pulsed with CD33 peptide plus β$_2$ microglobulin ÷ HLA-A2.1 mean channel fluorescence T2 cells pulsed with β$_2$ microglobulin only].
Fluorescence Index demonstrates the fold increase/decrease of peptide binding to HLA-A2.1 on the surface of T2 cells and the data represent the results of three separate experiments.

Dendritic and T2 Cells as Antigen Presenting Cells

In this example, immature DCs obtained by the culture of CD14+ monocytes with GM-CSF (1,000 U/ml) and IL-4 (1,000 U/ml) were induced to undergo maturation by incubation with LPS (100 Units/ml), TNF-α 10 ng/ml) or TNF-α (10 ng/ml)+IFN-α 50 ng/ml) during the final three days of the culture period. Flow cytometric analysis of the respective DC cultures showed a phenotypic profile characterized by high expression of CD40, CD80, CD83, CD86 or HLA-DR and no expression of CD3 or CD14 (data not shown). The highest up-regulation of the co-stimulatory (CD80 and CD86) and HLA-A2.1 MHC class I molecules was detected on DCs treated with TNF-α +IFN-A (Table 5). LPS or TNF-α alone also induced the high expression of CD80, CD86 and HLA-A2.1 molecules compared to the GM-CSF+IL-4 (immature DC) control group, however the up-regulation was not as high as seen treated with the TNF-α+IFN-α combination.

The phenotype of the T2 cell line was evaluated to determine its potential for use as an alternative type of antigen presenting cell. The results (Table 4) showed that T2 cells express high levels of co-stimulatory and HLA-A2.1 molecules. The expression levels of CD83 and CD86 molecules on T2 cells were comparable to those observed on mDCs (Table 4). The expression of CD80 was higher on T2 cells compared to mDCs. The phenotypic profiles of both the mDCs and T2 cells make them ideal candidates for use as antigen presenting cells in the generation of CD33 peptide-specific CTLs.

TABLE 4

Phenotypic analysis of mature dendritic (mDC) and T2 antigen-presenting cells.

| | HLA-A2.1 | CD80 | CD86 | CD83 |
|---|---|---|---|---|
| Immature DCs | 94 | 56 | 21 | ND[1] |
| DCs matured by LPS | 316 | 71 | 40 | ND |
| DCs matured by TNF-α | 475 | 107 | 96 | ND |
| DCs matured by IFN-α + TNF-α | 749 | 137 | 149 | 67 |
| T2 cells | 577 | 1214 | 155 | 50 |

ND[1] = not done
Phenotypic analysis of culture derived mDC or T2 antigen-presenting cells. Immature DCs were generated in vitro from CD14 + monocytes of HLA-A2.1 + normal donors by incubation with GM-CSF and IL-4 for 10 days in liquid culture. Immature DCs were induced to undergo the maturation by the addition of LPS, TNF- or TNF- + IFN- during the last three days of culture. Results are expressed as the mean channel fluorescence (MCF) for each antigen tested. Dendritic cells matured with TNF- + IFN- displayed the highest levels of HLA-A2.1, CD80, and CD86 expression compared to LPS or TNF-treated dendritic cell cultures. The T2 cell line had the highest level of CD80 expression and similar levels of HLA-A2.1 and CD86 expression to the TNF- + IFN- dendritic cells.

Cytolytic Activity by CD33 Peptide-Specific CTLs

Figure 2:
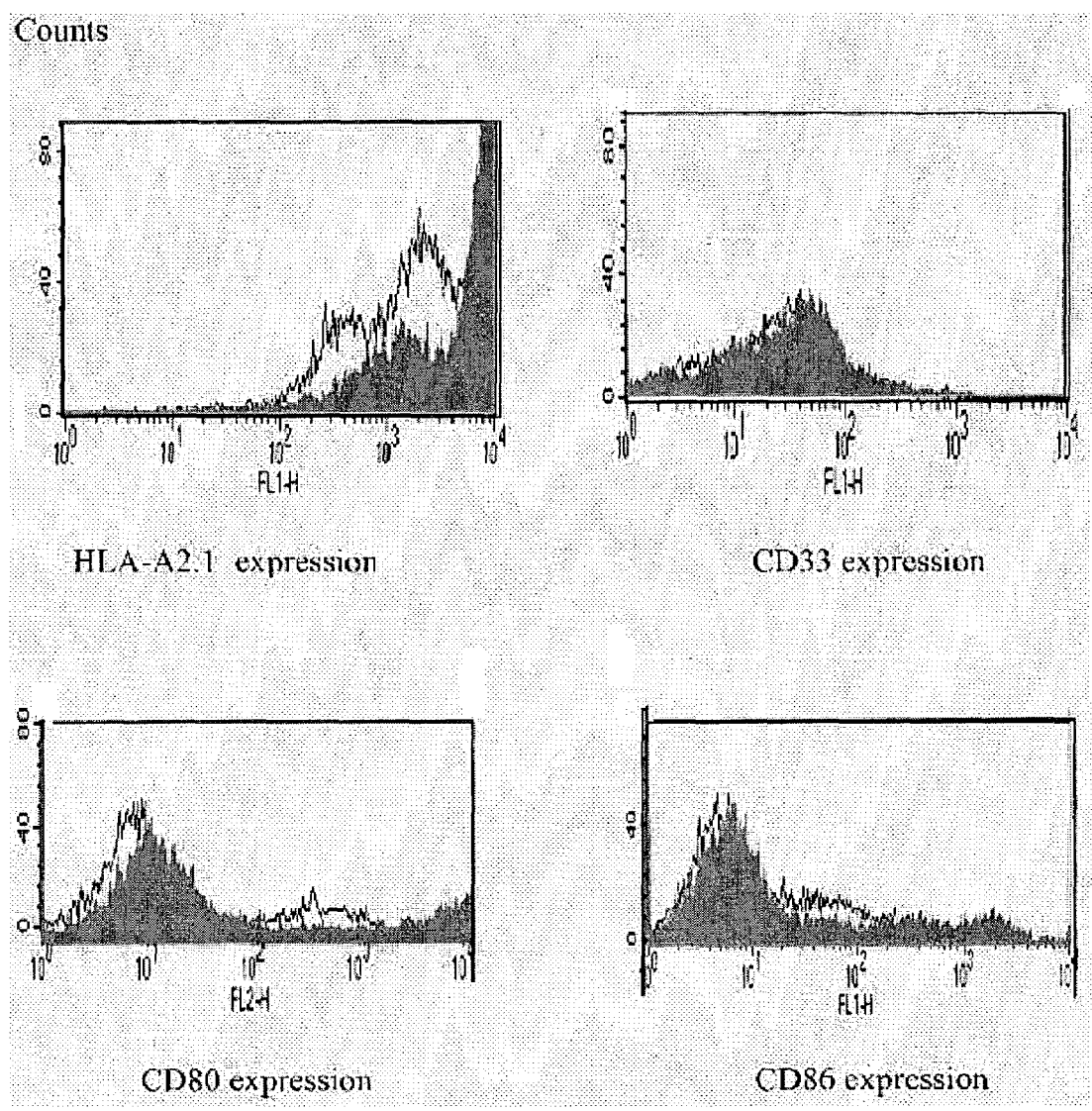
FIG. 2 shows up-regulation of HLA-A2.1, CD80, CD86 expressions on AML cells by cytokines treatment. Phenotype analysis was performed using untreated or cytokines (1,000 U/ml GM-CSF, 100 ng/ml IFN-γ, and 15 ng/ml TNF-a)-treated bone marrow blasts from HLA-A2.1+AML patients. Up-regulation of HLA-A2.1, CD80, and CD86, but not CD33 were observed on AML cells by the treatment of cytokines for two days. The values of mean fluorescence intensity are following (untreated vs. treated); 2198 vs. 6005 for HLA-A2.1, 42 vs. 53 for CD33, 114 vs. 1208 for CD80, and 51 vs. 267 for CD86 expression.
Figure 3:
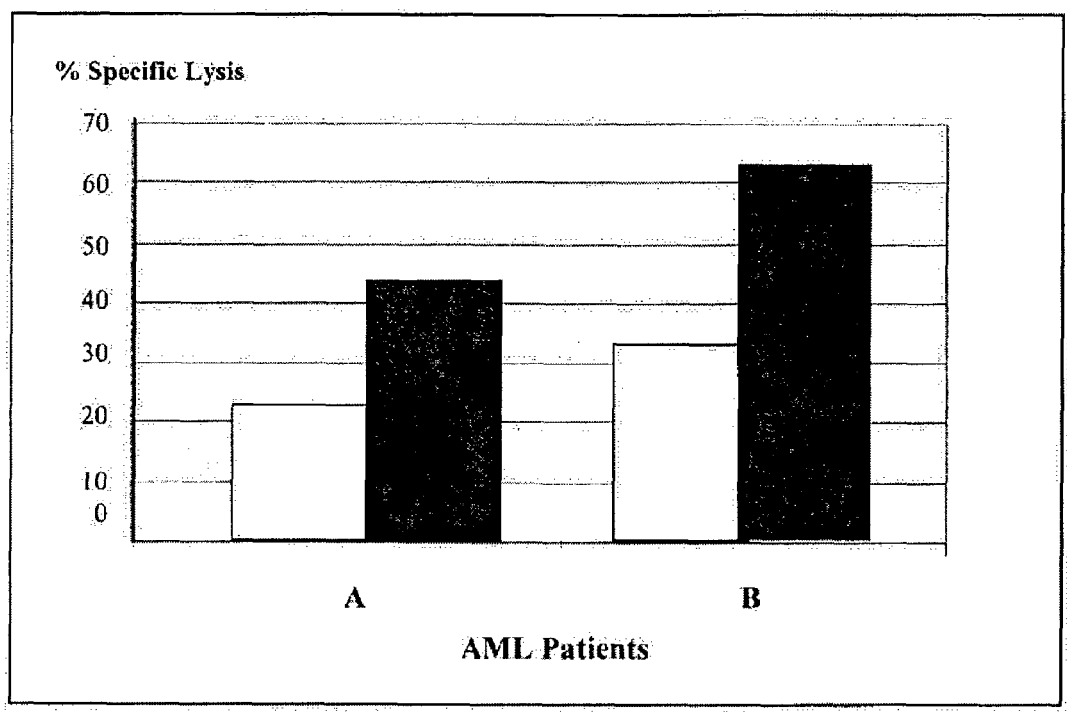
FIG. 3 shows the cytotoxic activity of peptide AIISGDSPV (SEQ ID NO: 2)-specific CTLs against bone marrow blasts from two AML patients (A, B). CTLs were generated by stimulating T lymphocytes obtained from an HLA-A2.1+ donor with autologus mature dendritic cells pulsed with this peptide. Data shows the $^{51}$Cr release assay performed one week after the second stimulation at an Effector: Target cell ratio of 60:1. Results demonstrate antigen-specific cytotoxicity against the untreated (white bars) or GM-CSF/IFN-γ/TNF-α treated (black bars) bone marrow blasts from both AML patients.

CD33 peptide-specific CTLs were generated by repeated stimulation of T-lymphocytes from healthy HLA-A2.1+donors with AIISGDSPV (SEQ ID NO:2)-pulsed autologous mDC. CTLs were harvested one week after the second peptide stimulation and examined for their cytolytic activity against allogeneic HLA-A2.1+AML patient bone marrow mononuclear cells. Differential counts of the AML patient samples demonstrated a high proportion of blast cells in both AML patient 1 (54% blasts) and patient 2 (77% blasts) samples. The CD33-peptide specific CTLs showed 22% and 33% of cytolytic activities against bone marrow mononuclear cells from AML patient 1 and AML patient 2, respectively. Cytokines treatment of the AML bone marrow cells with GM-CSF (1,000 U/ml), IFN-γ (100 ng/ml) and TNF-α (15 ng/ml) for 48 hours induced the up-regulation of co-stimulatory (CD80, CD86) and HLA-A2.1 molecules (FIG. 2), making them more susceptible to killing by CD33-CTLs. Cytotoxicity results (FIG. 3) showed the enhanced cytolytic activities against cytokines treated-AML patients bone marrow mononuclear cells (AML patient 1=43%, AML patient 2=63%) compared to the untreated AML cells (AML patient 1=22%, AML patient 2=33%).

Figure 4:
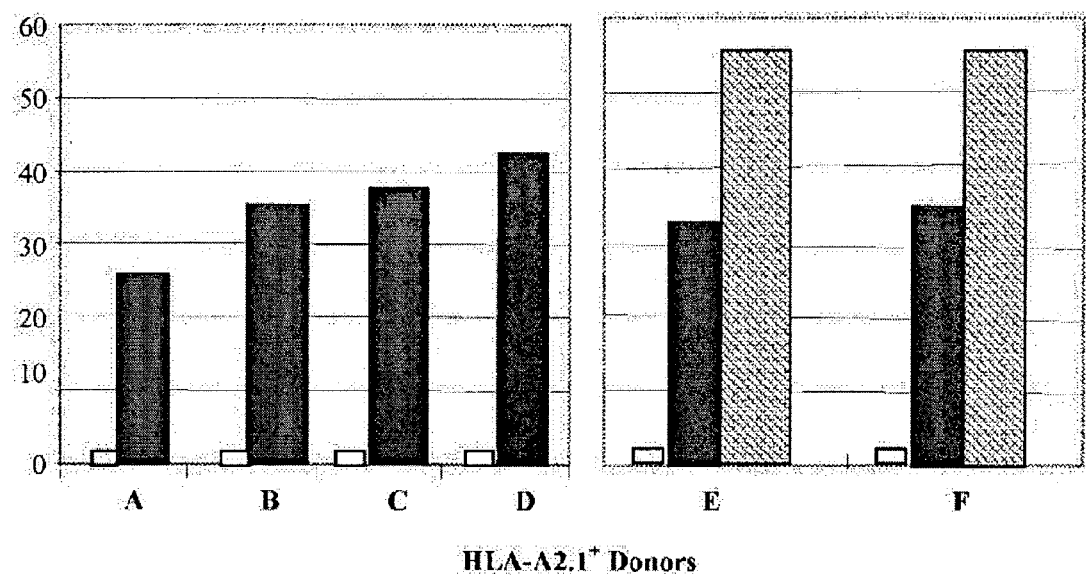
FIG. 4 shows the cytotoxic activity of peptide AIISGDSPV (SEQ ID NO: 2)-specific CTLs against the HLA-A2.1+ML-2 cells (AML cell line). CTLs were generated by stimulating T lymphocytes obtained from six different HLA-A2.1+ donors with either autologus mature DCs (A, B, C, D) or T2 (E, F) cells pulsed with this peptide. Data shows the $^{51}$Cr release assay performed one week after the last stimulation at an Effector:Target cell ratio of 60:1 (white bars—unstimulated, black bars—CTLs stimulated twice, hatched bars—CTLs stimulated three times). Results demonstrate high levels of antigen-specific cytotoxicities against cytokine (GM-CSF/IFN-γ/TNF-α) treated ML-2 cells by CD33-specific CTLs. Increasing number of stimulations of the CTLs enhanced the level of cytotoxicity against the target cells.
Figures 4, 5:
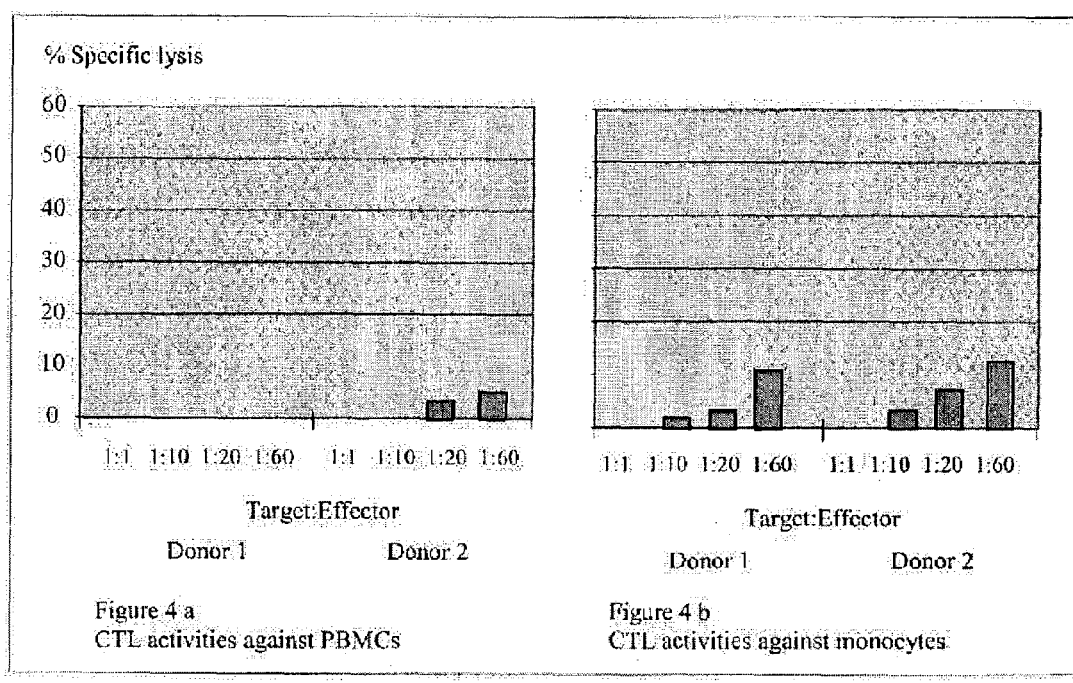
FIG. 5 shows the cytotoxic activity of CD33 peptide-specific CTLs against normal peripheral blood mononuclear cells (PBMCs) or monocytes. CD33 peptide-specific CTLs were generated by stimulating HLA-A2.1+ T lymphocytes with autologus mDCs pulsed with CD33 peptide. Assays were performed one week after the second stimulation to test the cytolytic activities of the CTLs against normal allogeneic HLA-A2.1+ PBMCs or monocytes (donor 1, 2). No significant cytotoxicities were observed by the CTLs at different ratios of Target: Effector.

Autologous mDCs or T2 cells as antigen presenting cells were also evaluated to induce AIISGDSPV (SEQ ID NO:2)-specific CTLs. T-lymphocytes from healthy HLA-A2.1+ donors were stimulated with either autologous mDC or T2 cells pulsed with the HLA-A2.1-specific AIISGDSPV (SEQ ID NO:2). The CTLs were harvested one week after the second or third stimulation and analyzed for their cytotoxic activities against the ML-2 cells (HLA-A2.1+ AML line). CD33 peptide-specific CTLs generated after two cycles of stimulation via either APC showed comparable cytotoxicities (FIG. 4). Unstimulated control T cells did not display any significant cytotoxicity against the target cells. Also, the data demonstrated that the repeated stimulation generated more effective CTLs; stimulation three times enhanced CTLs activities than two times. Based on this observation, generating CTLs with a minimum of three cycles of stimulation with peptide-pulsed mDCs to obtain highly effective CD33 peptide-specific CTLs is preferred. In following experiments, the possibility of the inhibition of normal cells expressing low levels of CD33 antigen by the CD33 peptide-specific CTLs was examined. CTLs were generated as previously described using mDCs and examined a week after second stimulation. The results indicated no induction of significant cytotoxic activities against PBMCs or monocytes (FIG. 5), suggesting that CD33 peptide-specific CTLs might not effect the inhibition of normal cells.

AML-Specific Cell Lysis

Figure 6:
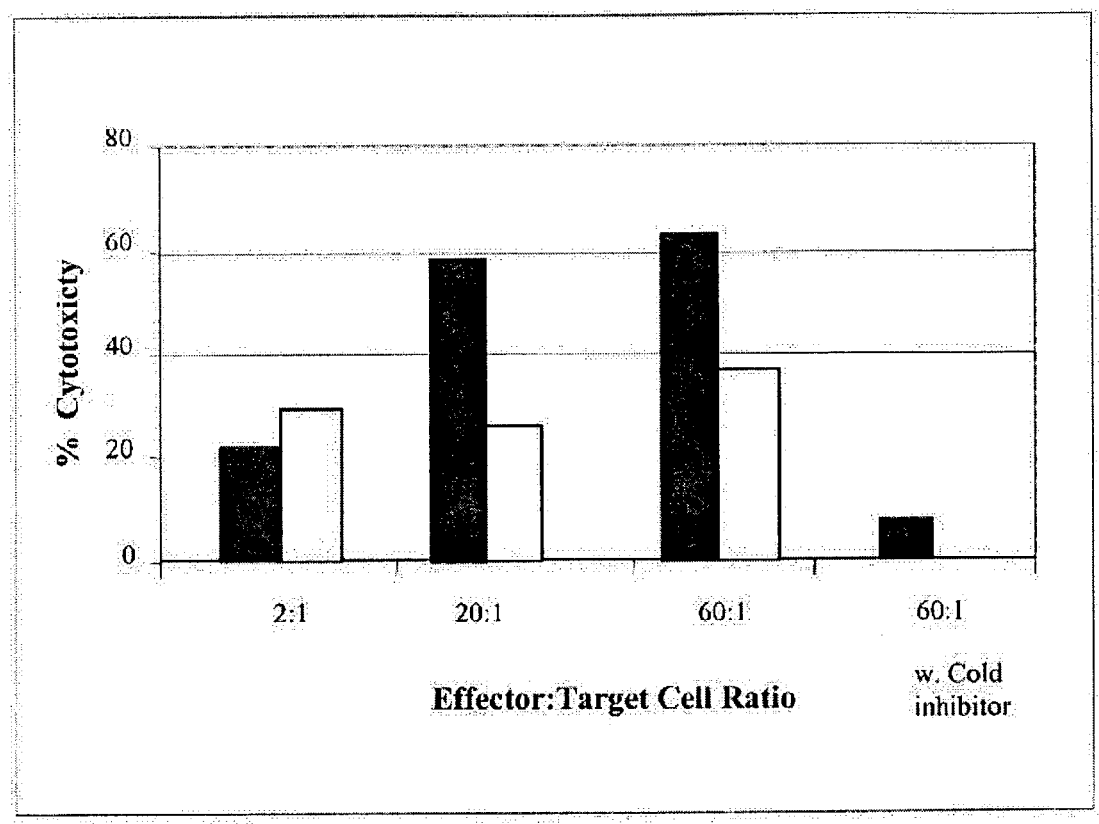
FIG. 6 shows the cytotoxicity of AIISGDSPV (SEQ ID NO: 2) peptide-specific CTLs evaluated in a Cold Target Inhibition assay. CTLs were incubated for 1 hour with "cold" unlabeled ML-2 cells before incubation with $^{51}$Cr labeled AML bone marrow blasts (white bars) or ML-2 cells (black bars). Results demonstrate the inhibition of cytotoxicity by the CD33+ HLA A2.1+"cold inhibitor" ML-2 cells against the CD33+HLA-A2.1+$51^{Cr}$-labeled target cells, and thus the cytotoxicity of the CTLs was AML cell-specific.

AML specific cell lysis by CD33 peptide-specific CTLs was confirmed using a cold target inhibition assay. In this assay, pre-incubation of CD33-CTLs with "cold" ML-2 cells for 1 hour before the addition of $^{51}$Cr-labeled (hot) AML target cells inhibited the cytotoxicity of the CD33-CTLs against the "hot" target cells. The ML-2 "cold" targets exhibit high levels of HLA-A2.1 and costimulatory molecules resulting in the CD33-CTLs reacting against the cold targets, thereby leaving limited activity against the "hot" AML patient cells. The results demonstrate that the cytotoxic activities induced by CD33 peptide-specific CTLs were CD33+ AML cell-specific (FIG. 6).

IFN-γ ELISA

The secretion of cytokines by antigen-specific T cells helps determine their effector cell function. IFN-γ secretion by antigen-specific T cells has been shown to contribute to host defense by initiating a potent local inflammatory response and is an important cytokine against tumor progression by orienting T lymphocytes into Th1-subtype (Ikeda et al., 2002; Beatty et al., 2001). The CD33 peptide-specific CTLs were evaluated for secretion of IFN-γ to analyze their Th1 cell subtype with potential anti-tumor activity. Supernatants from four HLA-A2.1+AIISGDSPV (SEQ ID NO:2)-specific CTL cultures were analyzed for IFN-γ production after repeated stimulation with the peptide. The amount of IFN-γ released was significantly higher in the culture supernatants of CD33-CTLs stimulated with AIISGDSPV (SEQ ID NO:2) pulsed mDCs or T2 cells compared to unstimulated control T-cells (Table 5). The results demonstrate that the CD33 peptide-specific CTLs generated with either mDCs or T2 cells are of a Th-1 subtype and could be potential effectors against CD33+ AML tumor cells.

TABLE 5

Phenotypic analyses of
mature dendritic (mDC) and T2 antigen-presenting cells.

|  | HLA-A2.1 | CD80 | CD86 | CD83 |
|---|---|---|---|---|
| Immature DCs | 94 | 56 | 21 | ND[1] |
| DCs matured by LPS | 316 | 71 | 40 | ND |
| DCs matured by TNF-α | 475 | 107 | 96 | ND |
| DCs matured by IFN-α + TNF-α | 749 | 137 | 149 | 67 |
| T2 cells | 577 | 1214 | 155 | 50 |

ND[1] = not done
Phenotypic analysis of culture derived mDC or T2 antigen-presenting cells. Immature DCs were generated in vitro from CD14+ monocytes of HLA-A2.1+ normal donors by incubation with GM-CSF and IL-4 for 10 days. Immature DCs were treated with LPS, TNF-α, or TNF-α + IFN-α during the last three days of culture to determine the optimal growth factor combination required for mature DC generation. Results are expressed as the mean channel fluorescence (MCF) for each antigen tested. Dendritic cells matured with TNF-α + IFN-α displayed the highest levels of HLA-A2.1, CD80, and CD86 expression compared to LPS or TNF-α cultured DCs. The T2 cell line which can be used as an antigen presenting cell had the highest level of CD80 expression and similar levels of HLA-A2.1 and CD86 expression to the TNF-α + IFN-α- cultured dendritic cells.

Isotypes of CD33 Peptide-Specific CTLs

Phenotypic analysis of the CD33 peptide-specific CTLs was performed for the expression of critical antigenic markers including CD8, CD69, CD45RA, CD45RO, and CD28 on the cell surfaces (Table 6). AIISGDSPV (SEQ ID NO:2) stimulated T cell cultures showed a higher percentage of CD8+ cytotoxic T cells or CD69+ activated cells compared to unstimulated T cells. The percentage of CD8+ cytotoxic T cells was increased by repeated stimulation of the cultures with CD33 peptide-pulsed mDCs (3 cycles=59% vs. 2 cycles=48%). In addition, the percentage of cells expressing the CD69 activation antigen increased from 69% after 2 stimulations to 82% after three stimulations with CD33 peptide-pulsed mDCs. The percentage of memory cells (CD45RO+) increased dramatically up to 90-95% with a subsequent decrease CD45RA+ naïve cells in the CD33-CTL cultures after three stimulations. The percentage of cells expressing CD28 was similar between CD33 peptide-specific CTLs and unstimulated T cells implying that the proliferative capacity of the cells was maintained in the cultures.

TABLE 6

Phenotype of CD33 peptide-specific CTLs following repeated
stimulation of CTLs with mDC-CD33 peptide.

| Antigen | Cell Type/Function | Number of CTL stimulations with mDC-CD33 peptide | | | |
|---|---|---|---|---|---|
| | | 0 | 1 | 2 | 3 |
| CD8 | Cytotoxicity | 22 ± 0.71% | 48 ± 4.24% | 54 ± 7.78% | ND[1] |
| CD69 | Activation | 2 ± 1.41% | 8 ± 1.41% | 39 ± 4.24% | 76 ± 9.19% |
| CD45RA | Naive T | 71 ± 7.07% | 57 ± 1.41% | 8 ± 4.24% | ND |
| CD45RO | Memory T | 52 ± 2.12% | 79 ± 0.71% | 93 ± 3.54% | ND |
| CD28 | Proliferation | 96 ± 2.12% | 81 ± 1.41% | 85 ± 3.54% | 89 ± 2.12% |

ND[1] = not done
The phenotype of CD33 peptide specific CTLs was determined by flow cytometry following repeated stimulation of the CTLs with mDCs pulsed with CD33 peptide. Results are expressed as the mean ± standard deviation (n = 3).

Detection of CD33 Peptide-Recognizing CTLs by Tetramer Staining

Figure 7:
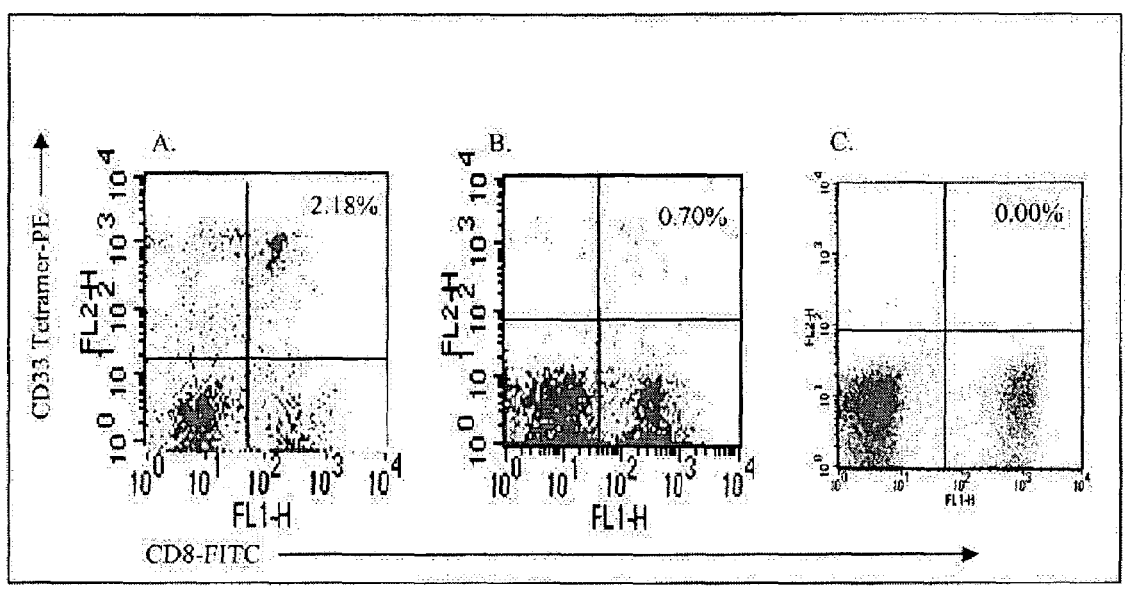
FIG. 7 shows the identification of tetramer-reactive CD8+ T lymphocytes before and after in vitro AIISGDSPV (SEQ ID NO: 2) peptide-specific stimulation. T-lymphocytes from HLA-A2.1+ normal donors after A) CD33 peptide-specific stimulation (3×), B) unstimulated HLA-A2.1+, or C) unstimulated HLA-A2.1− T lymphocytes were stained with anti-CD8-FITC and PE-conjugated CD33-AIISGDSPV-HLA-A2.1 tetrameric complexes. The percentage of tetramer+CD8+ T cells are shown in the upper right quadrant of the dot plots.

The CTL population recognizing AIISGDSPV (SEQ ID NO:2) was characterized using AIISGDSPV (SEQ ID NO:2)-HLA-A2.1-tetramers. Peptide-HLA-A2.1 tetramers are complexes of four HLA-A2.1 molecules associated with a specific peptide and a fluorochrome (Altman et al., 1996). The complexes bind to a distinct set of T cell receptors on a subset of CD8+ T cells recognizing the specific peptide. CTLs recognizing the AIISGDSPV (SEQ ID NO:2) were identified by staining with AIISGDSPV (SEQ ID NO:2)-HLA-A2.1-tetramers-PE and CD8-FITC antibodies. Flow cytometric analysis showed that 2.18% of the cells in the AIISGDSPV (SEQ ID NO:2) stimulated cultures was tetramer+CD8+ versus 0.7% or 0% in unstimulated T cells from HLA-A2.1+or HLA-A2.1-healthy donors, respectively (FIG. 7).

Discussion of Results

In this example, the CD33 epitope was specific to HLA-A2.1, since this is the most dominant HLA class I molecule; representing approximately 50% of North American Caucasians, 34% of African-Americans, and 55% of Asian-Americans (Baur et al., 1980). The identification of the CD33 epitope was performed by the evaluation of the amino acid sequence of CD33 for peptide motifs, which were likely to bind to HLA-A2.1. A synthetic peptide homologue of an identified nonamer motif within CD33 was examined for the contents to bind to HLA-A2.1 and to elicit the peptide-specific CTLs by in vitro immunization.

Dendritic cells (DCs) have been used as an APC because of their unique capacity to activate naïve T cells and initiate primary antigen-specific T-cell responses (Steinmann A M, 1991; Porgador et al., 1995; Zitvogel et al., 1996). Presentation of antigens by DCs may be especially important to inducing heightened immune responses to self-antigens since many immunization protocols targeting self-antigens have often resulted in the induction of low-affinity CTL responses (Brossart et al., 1996; Houbiers et al., 1993). In this example, mature type of dendritic cells was used to present exogeneous peptide sufficiently into T cells to evoke the peptide-specific CTLs, thus optimal maturation factors for DCs were examined. Among a few trials, TNF-α and IFN-α induced the best maturation, by demonstrating the most up-regulation of HLA-A2.1 and costimulatory molecules on their cell surfaces by the treatment of these cytokines. Also, T2 cells, which express significant levels of CD80 and CD86 costimulatory and HLA-A2.1 molecules like DCs, were used as an alternative APCs. The results of this study demonstrated that CD33 peptide-specific CTLs lysed primary allogeneic AML blasts from HLA-A2.1+patients or a HLA-A2.1+AML cell line and implies that the CTLs might be efficiently used as effective cells for immunotherapy in AML patients. Low expression of HLA-A2.1 and costimulatory molecules on AML cells was up-regulated by 48 hours treatment with GM-CSF, IFN-γ and TNF-α. The up-regulation of these molecules was associated with increased recognition of the AML cells by CD33 peptide-specific CTLs and induction of higher cytotoxicity by the CTLs. Thus, the prior treatment of AML patients with these cytokines might improve the recognition of AML cells by the CTLs and enhance the potential immunotherapy outcome. The present example also demonstrated that DCs and T2 cells efficiently work as functional APCs to generate CD33 peptide-specific CTLs having comparable cytolytic activities. Also, significant amounts of IFN-γ were released from the CTLs generated with either DCs or T2 cells-pulsed with CD33 peptide. Thus, these results suggest the usage of T2 cells for future clinical application to overcome the limited numbers of DCs and to save the time/efforts to generate DCs.

AML specific cytotoxicity by CD33 peptide-specific CTLs was confirmed in the cold-target inhibition assay. Complete blocking of the cytolytic activities was obtained by preincubation with unlabeled AML cells before the addition of $^{51}$Cr-labeled bone marrow blasts from AML patients or an AML cell line. The staining of cells with tetramer-PE and anti-CD8 antibody-FITC demonstrated that about 2% of stimulated cells are the CD33 peptide-recognizing cytotoxic T lymphocytes. Further phenotypic analysis showed a higher percentage of CD8 (cytotoxic T), CD45RO (memory), and CD69 (activation) expressing cells following stimulation with CD33 peptide. Expansion of each cell subtype (CD8, CD45RO, CD69) was observed by repeated stimulation. Also, high levels of CD28 expression on CTLs were observed, and it suggests that proliferative capacity of the stimulated cells will be maintained. Therefore, this study demonstrates the potential efficacy of utilizing CD33-specific peptide for immunotherapy in AML patients who relapsed after AlloSCT. T-cell based immunotherapy may be accomplished in vivo by the activation and proliferation of anti-leukemia T cells by the administration of CD33 peptide alone or dendritic cells pulsed with CD33 peptide or by the infusion of HLA-compatible anti-leukemia T cell clones generated in vitro against the peptide.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

All references disclosed herein, including those cited hereafter, are specifically incorporated herein by reference thereto.

While preferred embodiments have been illustrated and described, it should be understood that changes and modifications can be made therein in accordance with ordinary skill in the art without departing from the invention in its broader aspects as defined in the following claims.

The following are full citations of publications cited in the present application:

Altman J. D. et al. Science. 1996;274:94-96.
Andrews R. G. et al. J. Exp. Med. 1989;169:1721-1731.
Andrews R. G. et al. Blood. 1983;62:124-132.
Appelbaum F. R. et al. Hematology. 2001;62-86.
Bakker A. B. et al. Cancer Res. 1995;55:5330-5334.
Baur M. P. et al. Genet. Epidemiol. 1989;6:15-20.
Beatty G. L. et al. Immunol. Res. 2001;24:201-210.
Bross P. F. et al. Clin. Cancer Res. 2001;7:1490-1496.
Brossart P. et al. J. Exp. Med. 1996;183:2449-2458.
Chen Z. et al. Int. J. Cancer. 2001;93:539-548.
Cripe L. D. et al. Curr. Treat. Options. Oncol. 2000;1:9-17.
Dinndorf P. A. et al. Blood. 1986;67:1048-1053.
Faber L. et al. J. Exp. Med. 1992;176:1283-1287.
Falkenburg J. et al. Curr. Opin. Hematol. 1993;1:228-232.
Gao Z. et al. Lancet. 2001;357:932-933.
Griffin J. D. et al. Leuk. Res. 1984;8:521-534.
Horowitz M. C. et al. J. Bone Joint Surg. Am. 1991;73:1157-1168.
Hinkel A. et al. J. Immunother. 2000;23:83-93.
Houbiers J. G. et al. Eur. J. Immunol. 1993;23:2072-2077.
Ikeda H. et al. Cytokine Growth Factor Rev. 2002;13:95-109.
Kolb H. et al. Blood. 1995;86:2041-2050.
Lapointe R. et al. Eur. J. Immunol. 2000;30:3291-3298.
Legrand O. et al. Blood. 2000;96:870-877.
Mackinnon S., et al. Blood. 1995;86: 1261-1265.
Maecker B. et al. Blood. 2000;96:830a (#3589).
Marmont A. M. et al. Blood. 1991;78:2120-2130.
McDonald G. B. Clin. Lymphoma. 2002;Suppl. 1:S35-9.
McGavin J. K., et al. Drugs. 2001;61:1317-1322.
Molldrem J. et al. Nat. Med. 2000; 6:1018-1023.
Morel Y. et al. J. Immunol. 2001;167:2479-2486.
Murashige N. et al. Am. J. Hematol. 2002;71:94-97.
Nabhan C. et al. Clin. Lymphoma. 2002;Suppl. 1:S19-23.
Naito K. et al. Leukemia. 2000;14:1436-1443.
Nijman H. W. et al. Eur. J. Immunol. 1993;23:1215-1219.
Ohminami H. et al. Blood. 2000;95:286-293.
Peiper S. C. et al. Report on the CD33 cluster workshop: biochemical and genetic characterization of gp67. In: Knapp W, Dorken B., Gilks W R, et al., eds. Leucocyte typingIV: White Cell Differentiation Antigens. 1st ed. Oxford, England: Oxford University Press, 1989: 814-816.
Porgador A. et al. J. Exp. Med. 1995; 182:255-260.
Radich J. et al. Oncology. 2000;14:125-131.
Robertson M. et al. Blood. 1992;79:2229-2236.
Romani N. et al. J. Exp. Med. 1994;180:83-89.
Salter R. D. et al. EMBO J. 1986;5:943-949.
Scheimberg I. B. et al. Histopathology. 1995;26:311-321.
Schuurhuis D. H. et al. J. Exp. Med. 2000;192:145-150.
Sievers E. L. et al. J. Clin. Oncol. 2001;19:3244-3254.
Simmon D. et al. J. Immunol. 1988;141:2797-2802.
Steinman A.M. Annu. Rev. Immunol. 1991;9:271-296.
Tchilian E. Z. et al. Blood. 1994;83:3188-3198.
van Rhee F. et al. Blood. 1994;83:3377-3381.
Wagner J. E. et al. J. Clin. Oncol. 1992;10:779-789.
Young J. W. et al. Blood. 1992;79:3380-3387.
Zitvogel L. et al. J. Exp. Med. 1996;183:87-97.
Zweerink H. J. et al. J. Immunol. 1993; 150:1763-1771.

What is claimed is:

1. An isolated leukemic antigen consisting of a fragment of CD33 antigen selected from the group consisting of: YLALCLCLI (SEQ ID NO: 1), AIISGDSPV (SEQ ID NO: 2), YIISGDSPV (SEQ ID NO: 3), YIISGISPV (SEQ ID NO: 6), YLISGDSPV (SEQ ID NO: 7), ALLALCLCL (SEQ ID NO: 8), TIQLNVTYV (SEQ ID NO: 9), YIGSGDSPV (SEQ ID NO: 10), YIIIGDSPV (SEQ ID NO: 11), YIILGDSPV (SEQ ID NO: 12), YIISGDLPV (SEQ ID NO: 13), YIISGDSWV (SEQ ID NO: 14), YIISGDSPL (SEQ ID NO: 15), ALISGDSPV (SEQ ID NO: 16) and LLALCLCLI (SEQ ID NO: 42).

2. A pharmaceutical composition comprising one or more isolated leukemic antigens of claim 1 and a pharmaceutically acceptable carrier.

3. The pharmaceutical composition of claim 2 further comprising one or more co-immunostimulatory molecules.

* * * * *

UNITED STATES PATENT AND TRADEMARK OFFICE
CERTIFICATE OF CORRECTION

| | | |
|---|---|---|
| PATENT NO. | : 7,527,793 B2 | Page 1 of 1 |
| APPLICATION NO. | : 10/428335 | |
| DATED | : May 5, 2009 | |
| INVENTOR(S) | : Bae et al. | |

It is certified that error appears in the above-identified patent and that said Letters Patent is hereby corrected as shown below:

On the Title page,

[*] Notice:     Subject to any disclaimer, the term of this patent is extended or adjusted under 35 USC 154(b) by 594 days Delete the phrase "by 594 days" and insert -- by 930 days --

Signed and Sealed this

Fourth Day of May, 2010

David J. Kappos
*Director of the United States Patent and Trademark Office*